(12) United States Patent
Skaar et al.

(10) Patent No.: US 9,867,879 B2
(45) Date of Patent: Jan. 16, 2018

(54) METHODS FOR USE OF SMALL MOLECULE ACTIVATORS OF HEM-Y / PROTOPORPHYRINOGEN OXIDASE (PPO)

(71) Applicant: Vanderbilt University, Nashville, TN (US)

(72) Inventors: Eric P. Skaar, Brentwood, TN (US); Matthew Surdel, Nashville, TN (US); Gary A. Sulikowski, Brentwood, TN (US); Brendan Dutter, Nashville, TN (US); Paul Reid, Durham, NC (US); Alex Waterson, Murfreesboro, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 15/004,141

(22) Filed: Jan. 22, 2016

(65) Prior Publication Data
US 2016/0213780 A1 Jul. 28, 2016

Related U.S. Application Data

(60) Provisional application No. 62/106,649, filed on Jan. 22, 2015.

(51) Int. Cl.
| | |
|---|---|
| A61K 41/00 | (2006.01) |
| C07D 405/04 | (2006.01) |
| C07D 409/04 | (2006.01) |
| C07D 231/12 | (2006.01) |
| C12Q 1/18 | (2006.01) |
| C12N 9/02 | (2006.01) |
| C12Q 1/68 | (2006.01) |
| A61N 5/06 | (2006.01) |

(52) U.S. Cl.
CPC ........ *A61K 41/0057* (2013.01); *C07D 231/12* (2013.01); *C07D 405/04* (2013.01); *C07D 409/04* (2013.01); *C12N 9/001* (2013.01); *C12Q 1/689* (2013.01); *A61N 5/062* (2013.01); *A61N 5/0624* (2013.01); *C12Q 2600/136* (2013.01); *C12Q 2600/156* (2013.01); *C12Y 103/03004* (2013.01)

(58) Field of Classification Search
None
See application file for complete search history.

(56) References Cited

U.S. PATENT DOCUMENTS

| | | | |
|---|---|---|---|
| 7,255,691 B2 * | 8/2007 | Tolkoff | A61N 5/06 313/483 |
| 8,263,642 B2 * | 9/2012 | Skaar | A61K 31/17 424/404 |

FOREIGN PATENT DOCUMENTS

WO 2014/018925 1/2014

OTHER PUBLICATIONS

DeLeo, F. R., Otto, M., Kreiswirth, B. N., and Chambers, H. F. (2010) Community-associated meticillin-resistant *Staphylococcus aureus*. Lancet 375, 1557-68.
Yamamoto, T., Nishiyama, A., Takano, T., Yabe, S., Higuchi, W., Razvina, O., and Shi, D. (2010) Community-acquired methicillin-resistant *Staphylococcus aureus*: community transmission, pathogenesis, and drug resistance. J. Infect. Chemother. 16, 225-54.
Nathan, C. (2012) Fresh approaches to anti-infective therapies. Sci. Transl. Med. 4, 140sr2.
Somerville, G. A., and Proctor, R. A. (2009) At the crossroads of bacterial metabolism and virulence factor synthesis in *Staphylococci*. Microbiol. Mol. Biol. Rev. 73, 233-48.
Skaar, E. P., Humayun, M., Bae, T., DeBord, K. L., and Schneewind, O. (2004) Iron-source preference of *Staphylococcus aureus* infections. Science 305, 1626-8.
(Continued)

*Primary Examiner* — Kamal Saeed
(74) *Attorney, Agent, or Firm* — Stites & Harbison PLLC; Mandy Wilson Decker

(57) ABSTRACT

A method for treating a microbial infection involves administering an effective amount of a compound of the formula:

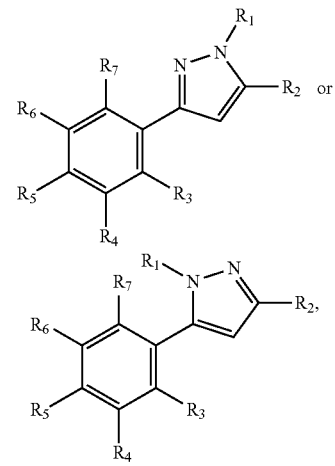

wherein $R_1$ is H, alkyl, aryl, heteroaryl, $R_2$ is H, halogen, alkyl, aryl, heteroaryl, $R_3$ is H, hydroxyl, alkoxy, alkyl, aryl, heteroaryl, amino, amino sulfonyl, acetamide, $R_4$ is H, hydroxyl, alkoxy, alkyl, aryl, heteroaryl, amino, amino sulfonyl, acetamide, $R_5$ is H, hydroxyl, alkoxy, alkyl, aryl, heteroaryl, amino, amino sulfonyl, acetamide, $R_6$ is H, hydroxyl, alkoxy, alkyl, aryl, heteroaryl, amino, amino sulfonyl, acetamide, $R_7$ is H, hydroxyl, alkoxy, alkyl, aryl, heteroaryl, amino, amino sulfonyl, acetamide, $R_8$ is —$CR_3$, O, S, wherein $R_5$ and $R_6$, $R_7$ and $R_6$, $R_5$ and $R_4$, $R_4$ and $R_3$ can cyclize forming a 3-10 member ring comprising C, O, S, and/or N optionally substituted with one or more $R_3$; and administering light therapy, such as a photodynamic therapy (PDT) light source.

9 Claims, 10 Drawing Sheets

(56) References Cited

OTHER PUBLICATIONS

Vlazmanian, S. K., Skaar, E. P., Gaspar, A. H., Humayun, M., Gornicki, P., Jelenska, J., Joachmiak, A., Missiakas, D. M., and Schneewind, O. (2003) Passage of heme-iron across the envelope of *Staphylococcus aureus*. Science 299, 306-9.

Torres, V. J., Pishchany, G., Humayun, M., Schneewind, O., and Skaar, E. P. (2006) *Staphylococcus aureus* IsdB is a hemoglobin receptor required for heme iron utilization. J. Bacteriol. 188, 8421-9.

Pishchany, G., Dickey, S. E., and Skaar, E. P. (2009) Subcellular localization of the *Staphylococcus aureus* heme iron transport components IsdA and IsdB. Infect. Immun. 77, 2624-34.

Anzaldi, L. L., and Skaar, E. P. (2010) Overcoming the heme paradox: heme toxicity and tolerance in bacterial pathogens. Infect. Immun. 78, 4977-89.

Friedman, D. B., Stauff, D. L., Pishchany, G., Whitwell, C. W., Torres, V. J., and Skaar, E. P. (2006) *Staphylococcus aureus* redirects central metabolism to increase iron availability. PLoS Pathog. 2, 0777-0789.

Torres, V. J., Stauff, D. L., Pishchany, G., Bezbradica, J. S., Gordy, L. E., Iturregui, J., Anderson, K. L., Dunman, P. M., Joyce, S., and Skaar, E. P. (2007) A *Staphylococcus aureus* regulatory system that responds to host heme and modulates virulence. Cell Host Microbe 1, 109-19.

Stauff, D. L., Torres, V. J., and Skaar, E. P. (2007) Signaling and DNA-binding activities of the *Staphylococcus aureus* HssR-HssS two-component system required for heme sensing. J. Biol. Chem. 282, 26111-21.

Johansson, P., and Hederstedt, L. (1999) Organization of genes for tetrapyrrole biosynthesis in Gram-positive bacteria. Microbiology 145, 529-538.

Mike, L. A., Dutter, B. F., Stauff, D. L., Moore, J. L., Vitko, N. P., Aranmolate, O., Kehl-Fie, T. E., Sullivan, S., Reid, P. R. DuBois, J. L., Richardson, A. R., Caprioli, R. M., Sulikowski, G. A., and Skaar, E. P. (2013) Activation of heme biosynthesis by a small molecule that is toxic to fermenting *Staphylococcus aureus*. Proc. Natl. Acad. Sci. U. S. A. 110, 8206-11.

Allison, K. R., Brynildsen, M. P., and Collins, J. J. (2011) Metabolite-enabled eradication of bacterial persisters by aminoglycosides. Nature 473, 216-220.

Kohler, C., von Eiff, C., Liebeke, M., McNamara, P. J., Lalk, M., Proctor, R. A., Hecker, M., and Engelmann, S. (2008) A defect in menadione biosynthesis induces global changes in gene expression in *Staphylococcus aureus*. J. Bacterial. 190, 6351-64.

Proctor, R. A., von Eiff, C., Kahl, B. C., Becker, K., McNamara, P., Herrmann, M., and Peters, G. (2006) Small colony variants: a pathogenic form of bacteria that facilitates persistent and recurrent infections. Nat. Rev. Microbial. 4, 295-305.

Fustero, S., Sánchez-Roselló, M., Barrio, P., and Simón-Fuentes, A. (2011) From 2000 to mid-2010: a fruitful decade for the synthesis of pyrazoles. Chem. Rev. 111, 6984-7034.

Richardson, D. R., and Bernhardt, P. V. (1999) Crystal and molecular structure of 2-hydroxy-1-naphthaldehyde isonicotinoyl hydrazone (NIH) and its iron(III) complex: an iron chelator with anti-tumour activity. J. Biol. Inorg. Chem. 4, 266-273.

Schwyn, B., and Neilands, J. B. (1987) Universal chemical assay for the detection and determination of siderophores. Anal. Biochem. 160, 47-56.

Fernadez, et al., (2010) "Two Coregulated Efflux Transporters Modulate Intracellular Heme and Protoporphyrin IX Availability in *Streptococcus agalactiae*," PLOS Pathogens, 6(4).

Heinemann, et al., Antimicrob. Agents Chemother. (2010).

Mike, et al., (2014) "Two-Component System Cross-Regulation Integrates Bacillus anthracis Response to Heme and sell Envelope Stress," PLOS Pathogens, 10(3).

Morimoto, et al, (2014), "Photodynamic Therapy Using Systemic Administration of 5-Aminolevulinic Acid and a 410-nm Wavelength Light-Emitting Diode for Methicillin-Resistant *Staphylococcus aureus*-Infected Ulcers in Mice," PLOS ONE, 9(8).

Nakonieczna, et al., (2010) "Superoxide dismutase is upregulated in *Staphylococcus aureus* following protoporphyrin-mediated photodynamic inactivation and does not directly influence the response to photodynamic treatment," BMC Microbiology, 10:323.

Qi, et al., Structural insight into unique properties of protoporphyrinogen oxidase from Bacillus subtilis, Journal of Structural Biology 170 (2010) 76-82.

Villarreal, et al., (2008) "Enhancement of Recombinant Hemoglobin Production in *Escherichia coli* BL21 (DE3) COntianing the Plesiomonas shigelloides Heme Transport System," Applied and Environmental Microbiology, 74(18): 5854-5856.

Wakeman, et al., (2014) "Differential Activation of *Staphylococcus aureus* Heme Detoxification Machinery by Heme Analogues," J. of Bacteriology, 196(7): 1335-42.

Kallander, L. S., Lu, Q., Chen, W., Tomaszek, T., Yang, G., Tew, D., Meek, T. D., Hofmann, G. A., Schulz-Pritchard, C. K., Smith, W. W., Janson, C. A., Ryan, M. D., Zhang, G.-F., Johanson, K. O., Kirkpatrick, R. B., Ho, T. F., Fisher, P. W., Mattern, M. R., Johnson, R. K., Hansbury, M. J., Winkler, J. D., Ward, K. W., Veber, D. F., and Thompson, S. K. (2005) 4-Aryl-1,2,3-triazole: a novel template for a reversible methionine aminopeptidase 2 inhibitor, optimized to inhibit angiogenesis in vivo. J. Med. Chem. 48, 5644-7.

Reed, C., Ibrahim, A., Edwards, J. E., Walot, I., and Spellberg, B. (2006) Deferasirox, an iron-chelating agent, as salvage therapy for rhinocerebral mucormycosis. Antimicrob. Agents Chemother. 50, 3968-9.

* cited by examiner

A.

B. ROUTE 1

ROUTE 2

Chromoazural S

Deferasirox

METHODS FOR USE OF SMALL MOLECULE ACTIVATORS OF HEM-Y / PROTOPORPHYRINOGEN OXIDASE (PPO)

RELATED APPLICATIONS

This application claims priority from U.S. Provisional Application Ser. No. 62/106,649 filed Jan. 22, 2015, the entire disclosure of which is incorporated herein by this reference.

GOVERNMENT INTEREST

This invention was made with government support under AI069233 and AI073843 awarded by the National Institutes of Health. The government has certain rights in the invention.

TECHNICAL FIELD

The presently-disclosed subject matter relates to treatment of microbial infections. In particular, the presently-disclosed subject matter relates to activators of protoporphyrinogen oxidase (PPO), also known as HemY and the treatment of microbial infections.

INTRODUCTION

Rapidly increasing resistance of pathogenic bacteria to relevant antimicrobials is a tremendous threat to global public health and has galvanized efforts focused on uncovering new targets for therapeutic intervention.

Staphylococcus aureus, for example, is a pathogen of humans primarily causing skin and soft tissue infections, but can also be responsible for more severe diseases including toxic shock syndrome and necrotizing pneumonias.[1] S. aureus has shown a remarkable propensity for developing resistance to antimicrobial therapies and drug resistant strains have increasingly become a significant threat to public health. Strains continue to demonstrate greater virulence and multidrug resistance in both healthcare and community settings, underscoring the need for the discovery of new antimicrobial compounds and pathways to target.[2,3]

S. aureus requires iron for normal cellular functions and evasion of the immune system during infection. In addition, the availability of iron controls the expression of many virulence factors.[4] In the human host, iron is tightly bound to storage and transport proteins and to heme in hemoproteins. While S. aureus can obtain iron from multiple sources, heme is its preferred iron source during infection[5], and the bacterium utilizes systems to scavenge heme from host hemoproteins, pass it through the cell wall and membrane, and either degrade heme to release free iron or store intact heme for incorporation into its own hemoproteins.[6,7,8]

Despite the value of heme as a nutrient iron source, heme is toxic to the bacteria in high concentrations.[9] In order to overcome heme toxicity, S. aureus employs a two component system called the heme sensor system (HssRS) to sense heme and activate a response to alleviate heme toxicity. HssS is a transmembrane histidine kinase that senses toxic levels of heme through an undetermined mechanism. Upon activation, HssS autophosphorylates and transfers the phosphate to an aspartate residue of its cognate response regulator, HssR. HssR is a cytoplasmic protein which, upon phosphorylation by HssS, binds the direct repeat of the promoter for the heme regulated transporter (hrtAB), a gene encoding an efflux pump that alleviates heme toxicity (FIG. 1).[10,11,12]

While heme serves as an iron source during infection, it is also an essential prosthetic group for proteins involved in respiration and detoxification of reactive oxygen species and S. aureus is capable of de novo heme biosynthesis.[13] Thus, activators of the HssRs two component system are of interest.

In the quest to combat increasing resistance of pathogenic bacteria to antimicrobials, the most successful antibiotic development strategies have exploited bacterial systems that are absolutely required for growth in culture. However, these screening strategies have prevented the identification of small molecules that target pathways conditionally required during infection. As with S. aureus, most bacterial pathogens have multiple ways of generating energy through central metabolic pathways that permit these organisms to adapt to alterations in available oxygen and the presence of diverse electron acceptors.

Therefore, flexibility in the regulation of central metabolism is critical to infectivity, based on the diverse environments that pathogens encounter when colonizing the vertebrate host. However, despite the tremendous therapeutic potential, small molecule screening strategies based on growth inhibition have not identified candidate therapeutics that target central metabolism. Novel systems, methods, and compositions for identification of targets and treatment of microbial infections are needed.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently disclosed subject matter includes methods, compounds, kits, and systems for treating microbial infections. The presently-disclosed subject matter also includes methods, compounds, and kits for activating the enzyme protoporphyrinogen oxidase (PPO), also known as HemY. The presently-disclosed subject matter further includes methods, compounds, and kits for producing hemoproteins. The presently-disclosed subject matter further includes methods, kits, and systems for screening for activators of HssRS and their targets. The presently-disclosed subject matter further includes unique compounds, which are useful in the methods disclosed herein.

Compounds that can be used in connection with the subject matter disclosed herein can include compounds of the formula

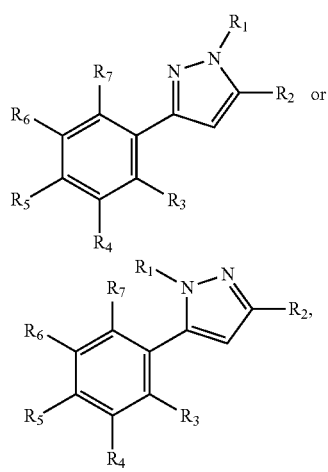

wherein,
R₁ is H, alkyl, aryl, heteroaryl;
R₂ is H, halogen, alkyl, aryl, heteroaryl;
R₃ is H, hydroxyl, alkoxy, alkyl, aryl, heteroaryl, amino, amino sulfonyl, acetamide;
R₄ is H, hydroxyl, alkoxy, alkyl, aryl, heteroaryl, amino, amino sulfonyl, acetamide;
R₅ is H, hydroxyl, alkoxy, alkyl, aryl, heteroaryl, amino, amino sulfonyl, acetamide;
R₆ is H, hydroxyl, alkoxy, alkyl, aryl, heteroaryl, amino, amino sulfonyl, acetamide;
R₇ is H, hydroxyl, alkoxy, alkyl, aryl, heteroaryl, amino, amino sulfonyl, acetamide;
R₈ is —CR₃, O, S; wherein R₅ and R₆, R₇ and R₆, R₅ and R₄, R₄ and R₃ can cyclize forming a 3-10 member ring comprising C, O, S, and/or N optionally substituted with one or more R₃.

In some embodiments of the compound, R₁ is H, alkyl, aryl; R₂ is H, halogen, alkyl, aryl, heteroaryl; R₃ is H, alkyl, hydroxyl, alkoxy, amino, amino sulfonyl, acetamide, aryl, heteroaryl; R₄ is H, alkyl, hydroxyl, alkoxy, amino, amino sulfonyl, acetamide; R₅ is H, alkyl, hydroxyl, alkoxy, amino, amino sulfonyl, acetamide; and R₆ is H, alkyl, aryl.

In some embodiments of the compound, R₁ is H, CH₃, or R₂ is H, CH₃, CH₂CH₃,

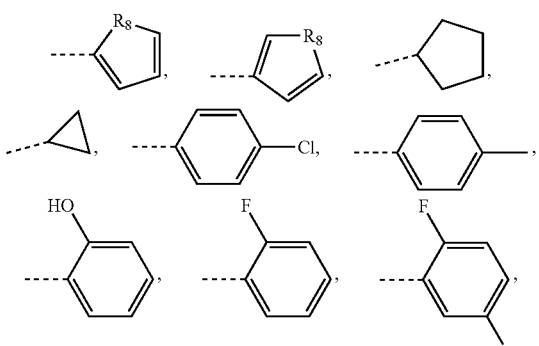

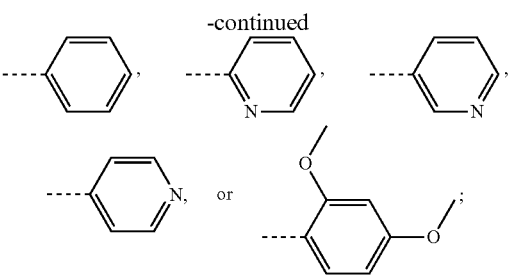

R₃ is H, OH,

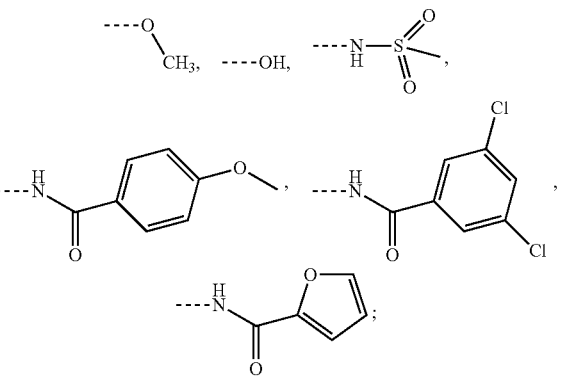

R₄ is H, OH,

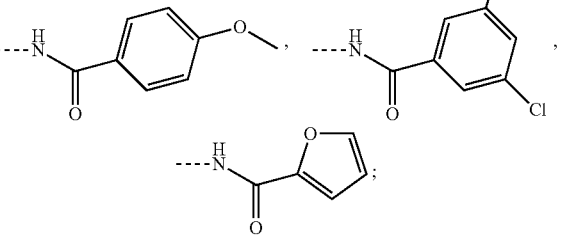

or R₄ and R₅, taken together with the carbon atoms to which they are bonded, can form an aromatic ring containing 6 carbon atoms;
R₅ is H, OH,

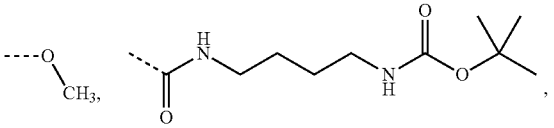

or R₄ and R₅, taken together with the carbon atoms to which they are bonded, can form an aromatic ring containing 6 carbon atoms, or R₅ and R₆, taken together with the carbon atoms to which they are bonded, can form an aromatic ring containing 6 carbon atoms;
R₆ is H, or R₅ and R₆, taken together with the carbon atoms to which they are bonded, can form an aromatic ring containing 6 carbon atoms;
R₇ is H or OH; and
R₈ is O or S.

Also included in the presently-disclosed subject matter are the compounds as set forth in Table 1, hereinbelow.

The presently-disclosed subject matter further includes novel compounds, which are included in Table 1.

The presently-disclosed subject matter further includes pharmaceutical compositions including a compound as described above and a pharmaceutically-acceptable carrier.

The presently-disclosed subject matter further includes kits for use in a method for treating a microbial infection, which can include a compound as disclosed herein, or a pharmaceutical composition including such compound, and further components useful for administrating the compound and administering light therapy. The presently-disclosed subject matter further includes a kit or system that further includes a light source, such as a PDT light source.

The presently-disclosed subject matter further includes methods for activating HemY/PPO in a cell, including contacting the cell with a compound as disclosed herein. In some embodiments the cell is a microbial cell, such as a bacterial cell, an animal cell, such as a human cell.

The presently-disclosed subject matter further includes a method for producing hemoproteins, which involves culturing a cell capable of generating hemoproteins, and contacting the cell with a compound as disclosed herein. While there are known methods for production of hemoproteins, they are often limited by an inability of the producing cell to make enough heme to populate the overexpressed hemoprotein. The compounds as disclosed herein can be used to modify such methods of overexpress hemoproteins of interest, providing sufficient levels of heme to populate the proteins, allowing for enhanced production and purification. The presently-disclosed subject matter further includes a kit for producing hemoproteins, which includes a cell (e.g., cell line, strain) capable of generating hemoproteins; and a compound as disclosed herein. The kit can further include media, reagents, plasmids, constructions, and devices useful for culturing the cell, expressing the protein of interest, application of the chemical, and/or collection and purification of the hemoprotein of interest. Relevant methods for generating hemoproteins, which can be improved by use of the compounds disclosed herein will be apparent to those of ordinary skill in the art upon studying this disclosure, and the following reference includes relevant information: Villarreal, et al., (2008) "Enhancement of Recombinant Hemoglobin Production in *Escherichia coli* BL21 (DE3) Containing the *Plesiomonas shigelloides* Heme Transport System," *Applied and Environmental Microbiology*, 74(18): 5854-5856.

The presently-disclosed subject matter further includes a system for screening for activators of HssRS and their targets. Provided is a unique *S. aureus*-based screening system useful for studying the mechanism of activation of the heme-sensing two-component system (TCS), HssRS. The unique system is useful for identifying compounds capable of activating HssRS, and for identifying the target of such compounds within the heme biosynthesis machinery, for example, small molecule targets of enzymes within the heme biosynthetic pathway. Small molecule activators of HssRS, as well as the targets of the small molecules, can be identified using the unique *S. aureus*-based screening system and methods disclosed herein.

When HssRS is stimulated, it induces expression of hrtAB. In the presently-disclosed system, the hrtAB promotor, Phrt, is placed upstream of the *E. coli* toxin, RelE, which impairs translation through mediating cleavage of mRNA, thus leading to growth arrest. The Phrt-RelE construct is inserted in place of the hrtAB locus. When a candidate small molecule that activates HssRS is contacted with a *S. aureus* phrt-relE cell, expression of RelE is induced, leading to cell death. In this manner, cell death allows a candidate small molecule to be identified as a small molecule activators of HssRS. Further, bacteria that survive the otherwise toxic treatment represent spontaneous resistant mutants. These surviving bacteria can be sequenced to identify genetic mutations. The target(s) of the small molecule activator will be the protein(s) containing the mutation(s) identified in the sequencing.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

DESCRIPTION OF EXEMPLARY EMBODIMENTS

Figure 1:
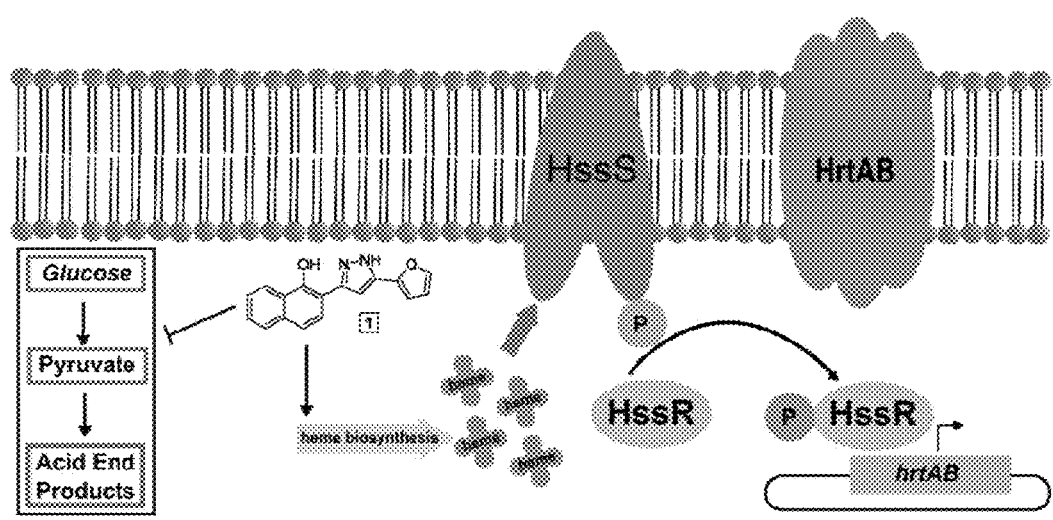
FIG. 1. An exemplary compound of the presently-disclosed subject matter, Compound 1, increases endogenous heme biosynthesis resulting in the accumulation of heme, which activates the heme sensor system (HssRS) through the sensor histidine kinase HssS. HssS autophosphorylates upon activation and transfers the phosphate to its cognate response regulator, HssR. HssR binds to the promoter of hrtAB, a gene encoding the heme regulated transporter (HrtAB) leading to its expression and resulting in alleviation of heme toxicity. 1 also inhibits the growth of bacteria under anaerobic conditions, potentially through inhibition of a process crucial to fermentation.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently disclosed subject matter includes methods, compounds, kits, and systems for treating microbial infections. The presently-disclosed subject matter also includes methods, compounds, and kits for activating the enzyme protoporphyrinogen oxidase (PPO), also known as HemY. The presently-disclosed subject matter further includes methods, compounds, and kits for producing hemoproteins. The presently-disclosed subject matter further includes methods, kits, and systems for screening for activators of HssRS and their targets. The presently-disclosed subject matter further includes unique compounds, which are useful in the methods disclosed herein.

Compounds that can be used in connection with the subject matter disclosed herein can include compounds of the formula

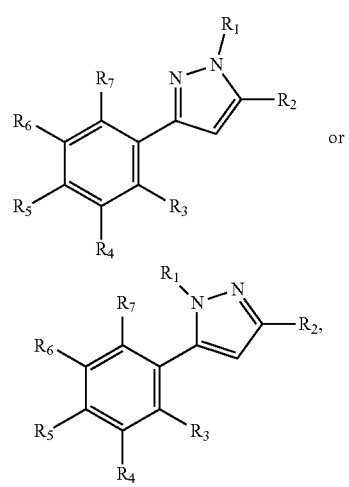

wherein,
$R_1$ is H, alkyl, aryl, heteroaryl;
$R_2$ is H, halogen, alkyl, aryl, heteroaryl;
$R_3$ is H, hydroxyl, alkoxy, alkyl, aryl, heteroaryl, amino, amino sulfonyl, acetamide;
$R_4$ is H, hydroxyl, alkoxy, alkyl, aryl, heteroaryl, amino, amino sulfonyl, acetamide;
$R_5$ is H, hydroxyl, alkoxy, alkyl, aryl, heteroaryl, amino, amino sulfonyl, acetamide;
$R_6$ is H, hydroxyl, alkoxy, alkyl, aryl, heteroaryl, amino, amino sulfonyl, acetamide;
$R_7$ is H, hydroxyl, alkoxy, alkyl, aryl, heteroaryl, amino, amino sulfonyl, acetamide;
$R_8$ is —$CR_3$, O, S; wherein $R_5$ and $R_6$, $R_7$ and $R_6$, $R_5$ and $R_4$, $R_4$ and $R_3$ can cyclize forming a 3-10 member ring comprising C, O, S, and/or N optionally substituted with one or more $R_3$.

In some embodiments of the compound, $R_1$ is H, alkyl, aryl; $R_2$ is H, halogen, alkyl, aryl, heteroaryl; $R_3$ is H, alkyl, hydroxyl, alkoxy, amino, amino sulfonyl, acetamide, aryl, heteroaryl; $R_4$ is H, alkyl, hydroxyl, alkoxy, amino, amino sulfonyl, acetamide; $R_5$ is H, alkyl, hydroxyl, alkoxy, amino, amino sulfonyl, acetamide; and $R_6$ is H, alkyl, aryl.

In some embodiments of the compound, $R_1$ is H, $CH_3$, or

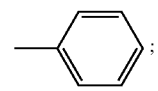

$R_2$ is H, $CH_3$, $CH_2CH_3$,

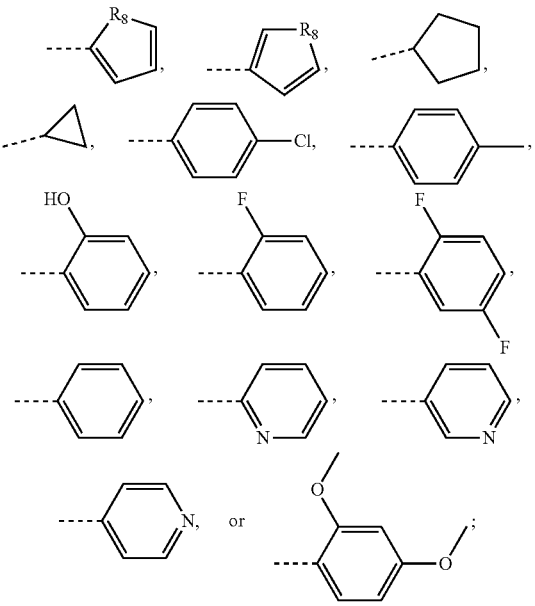

$R_3$ is H, OH,

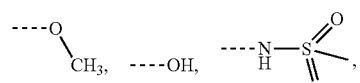

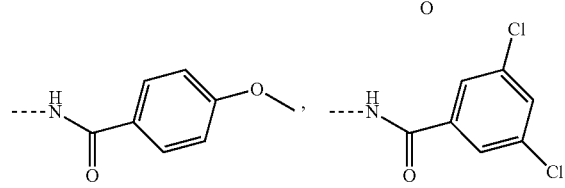

-continued

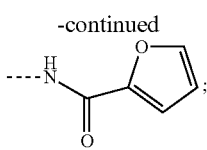

R$_4$ is H, OH,

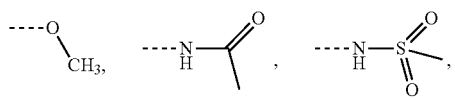

or R$_4$ and R$_5$, taken together with the carbon atoms to which they are bonded, can form an aromatic ring containing 6 carbon atoms;

R$_5$ is H, OH,

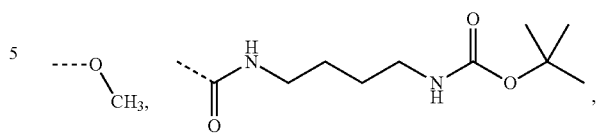

or R$_4$ and R$_5$, taken together with the carbon atoms to which they are bonded, can form an aromatic ring containing 6 carbon atoms, or R$_5$ and R$_6$, taken together with the carbon atoms to which they are bonded, can form an aromatic ring containing 6 carbon atoms;

R$_6$ is H, or R$_5$ and R$_6$, taken together with the carbon atoms to which they are bonded, can form an aromatic ring containing 6 carbon atoms;

R$_7$ is H or OH; and

R$_8$ is O or S.

Also included in the presently-disclosed subject matter are the compounds as set forth in Table 1.

TABLE 1

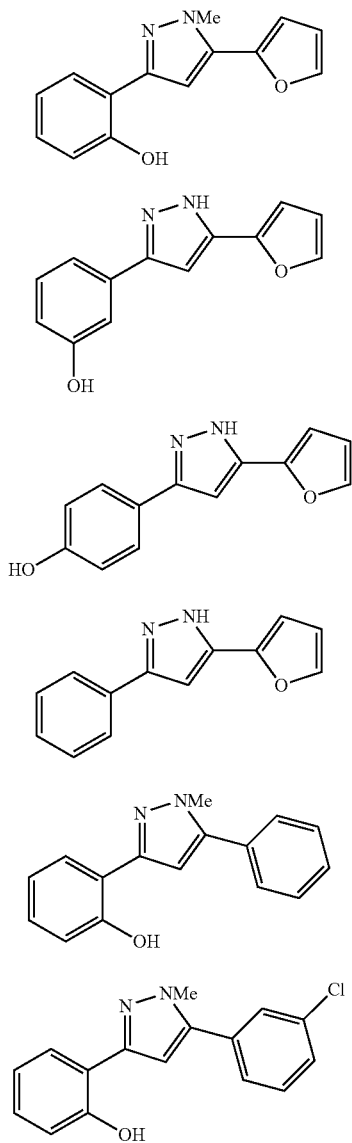

TABLE 1-continued
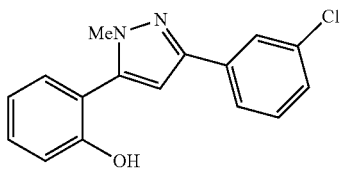 [SMILES: Cn1nc(-c2cccc(Cl)c2)cc1-c1ccccc1O]
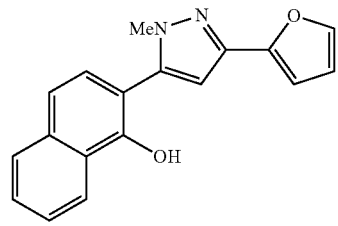 [SMILES: Cn1nc(-c2ccco2)cc1-c1ccc2ccccc2c1O]
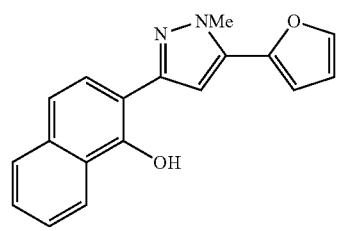 [SMILES: Cn1nc(-c2ccc3ccccc3c2O)cc1-c1ccco1]
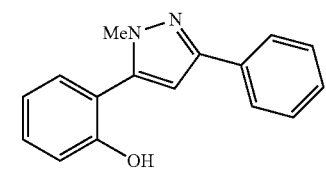 [SMILES: Cn1nc(-c2ccccc2)cc1-c1ccccc1O]
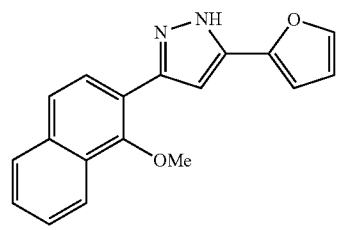 [SMILES: COc1c(-c2cc(-c3ccco3)[nH]n2)ccc2ccccc12]
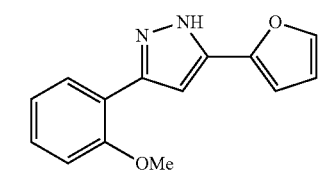 [SMILES: COc1ccccc1-c1cc(-c2ccco2)[nH]n1]
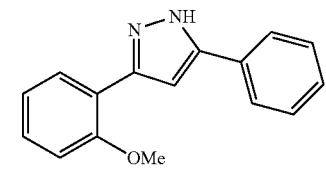 [SMILES: COc1ccccc1-c1cc(-c2ccccc2)[nH]n1]
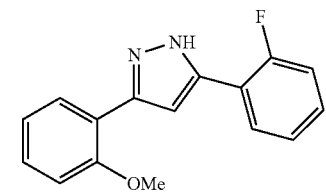 [SMILES: COc1ccccc1-c1cc(-c2ccccc2F)[nH]n1]

TABLE 1-continued
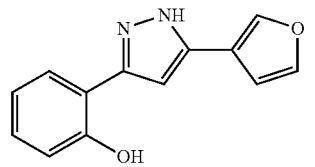 [SMILES: Oc1ccccc1-c1cc(-c2ccoc2)[nH]n1]
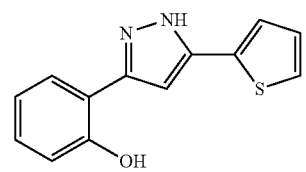 [SMILES: Oc1ccccc1-c1cc(-c2cccs2)[nH]n1]
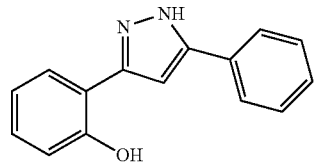 [SMILES: Oc1ccccc1-c1cc(-c2ccccc2)[nH]n1]
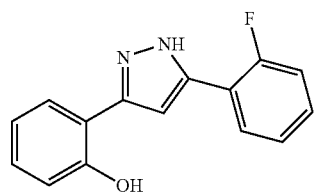 [SMILES: Oc1ccccc1-c1cc(-c2ccccc2F)[nH]n1]
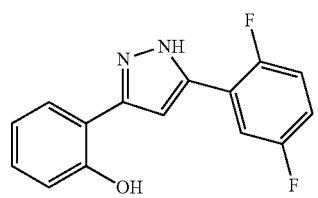 [SMILES: Oc1ccccc1-c1cc(-c2cc(F)ccc2F)[nH]n1]
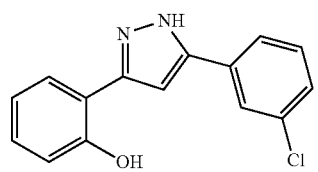 [SMILES: Oc1ccccc1-c1cc(-c2cccc(Cl)c2)[nH]n1]
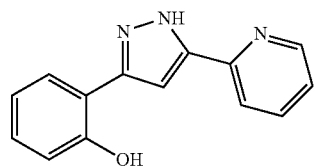 [SMILES: Oc1ccccc1-c1cc(-c2ccccn2)[nH]n1]
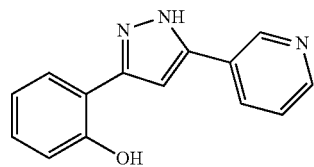 [SMILES: Oc1ccccc1-c1cc(-c2cccnc2)[nH]n1]
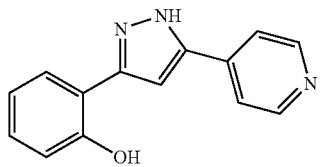 [SMILES: Oc1ccccc1-c1cc(-c2ccncc2)[nH]n1]

TABLE 1-continued
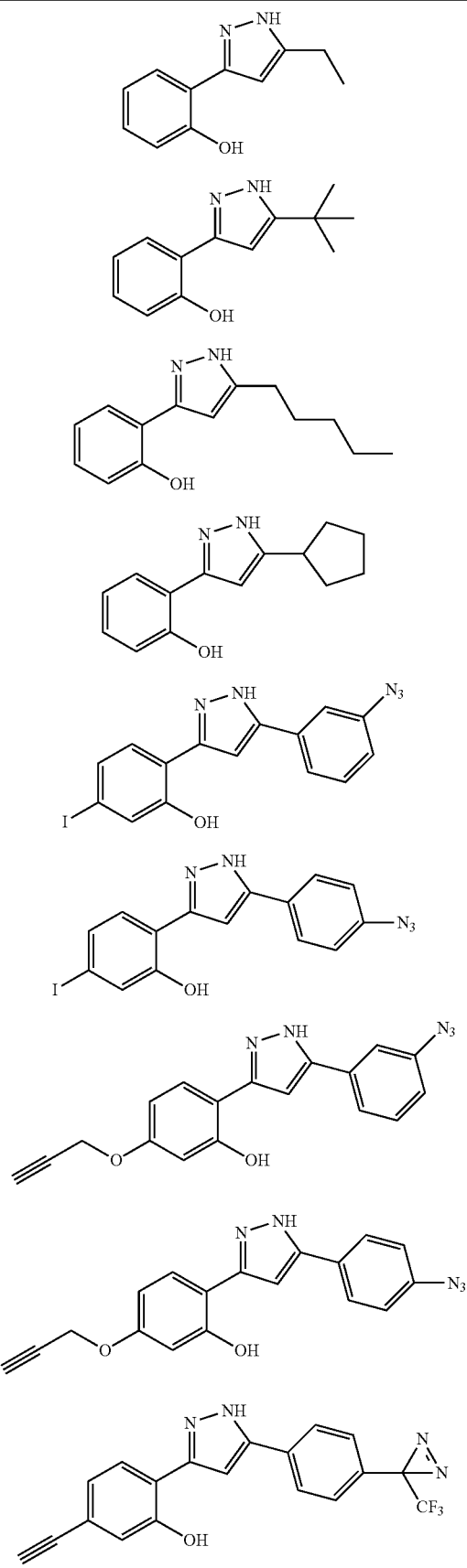

TABLE 1-continued
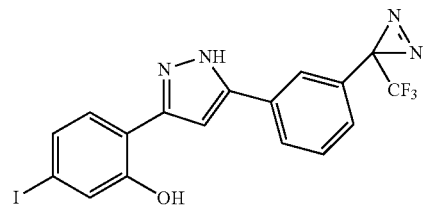 [SMILES: Oc1cc(I)ccc1-c1cc(-c2cccc(C3(C(F)(F)F)N=N3)c2)[nH]n1]
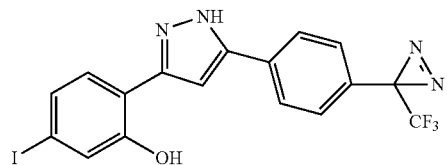 [SMILES: Oc1cc(I)ccc1-c1cc(-c2ccc(C3(C(F)(F)F)N=N3)cc2)[nH]n1]
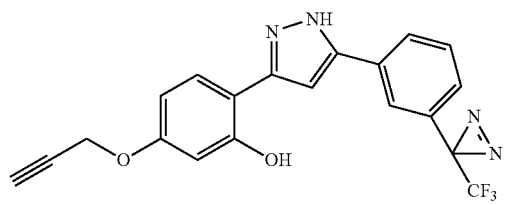 [SMILES: C#CCOc1ccc(-c2cc(-c3cccc(C4(C(F)(F)F)N=N4)c3)[nH]n2)c(O)c1]
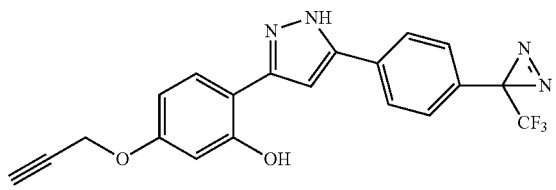 [SMILES: C#CCOc1ccc(-c2cc(-c3ccc(C4(C(F)(F)F)N=N4)cc3)[nH]n2)c(O)c1]
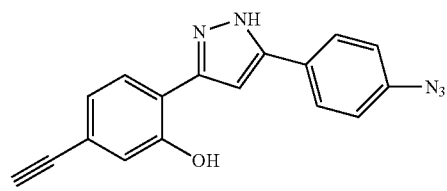 [SMILES: C#Cc1ccc(-c2cc(-c3ccc(N=[N+]=[N-])cc3)[nH]n2)c(O)c1]
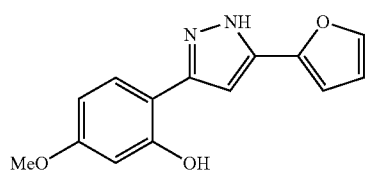 [SMILES: COc1ccc(-c2cc(-c3ccco3)[nH]n2)c(O)c1]
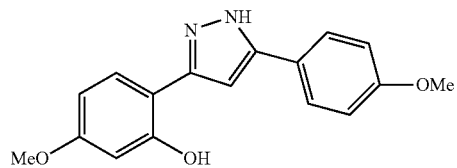 [SMILES: COc1ccc(-c2cc(-c3ccc(OC)cc3O)n[nH]2)cc1]
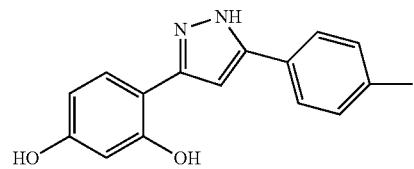 [SMILES: Cc1ccc(-c2cc(-c3ccc(O)cc3O)n[nH]2)cc1]

TABLE 1-continued
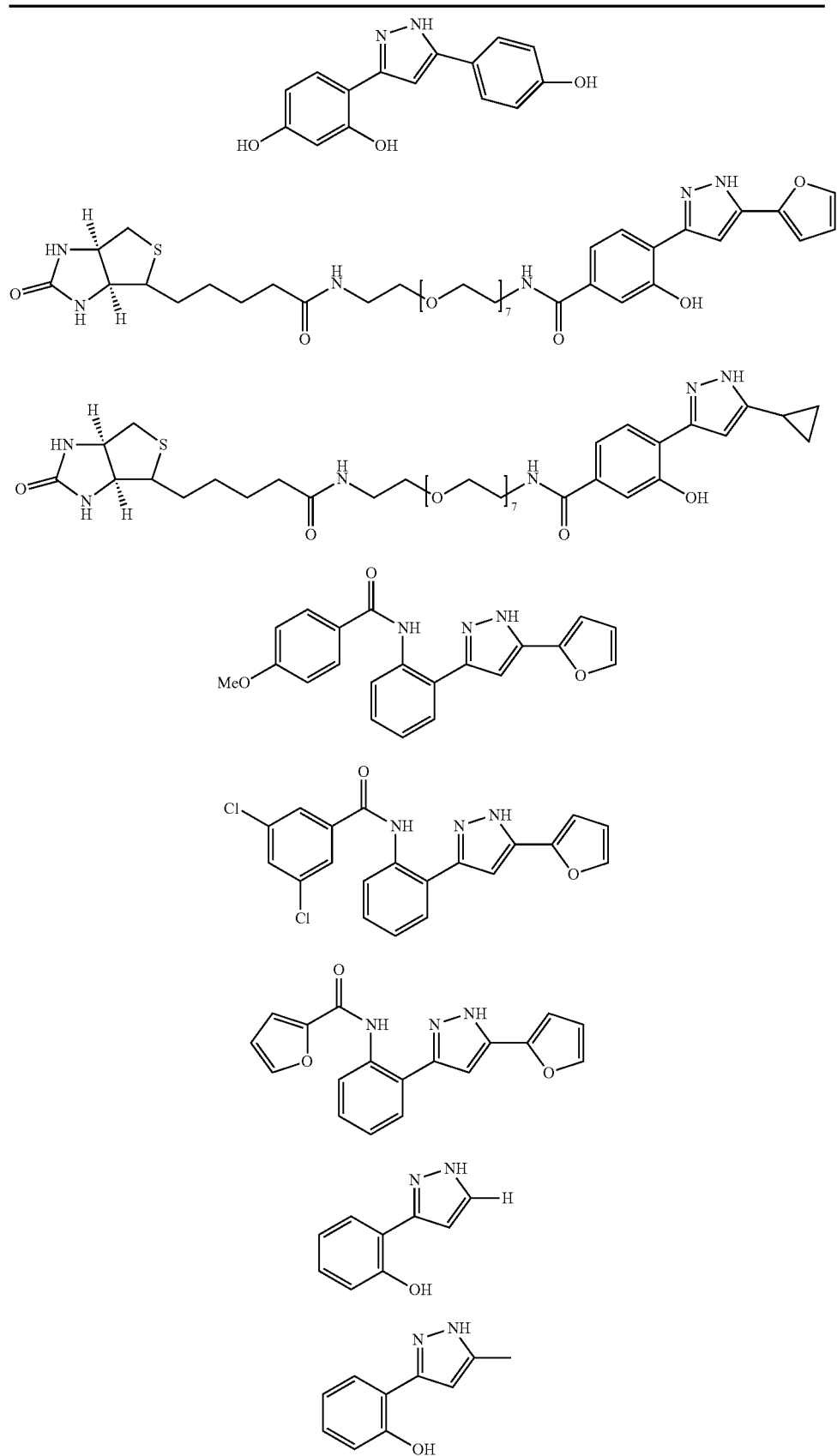

TABLE 1-continued
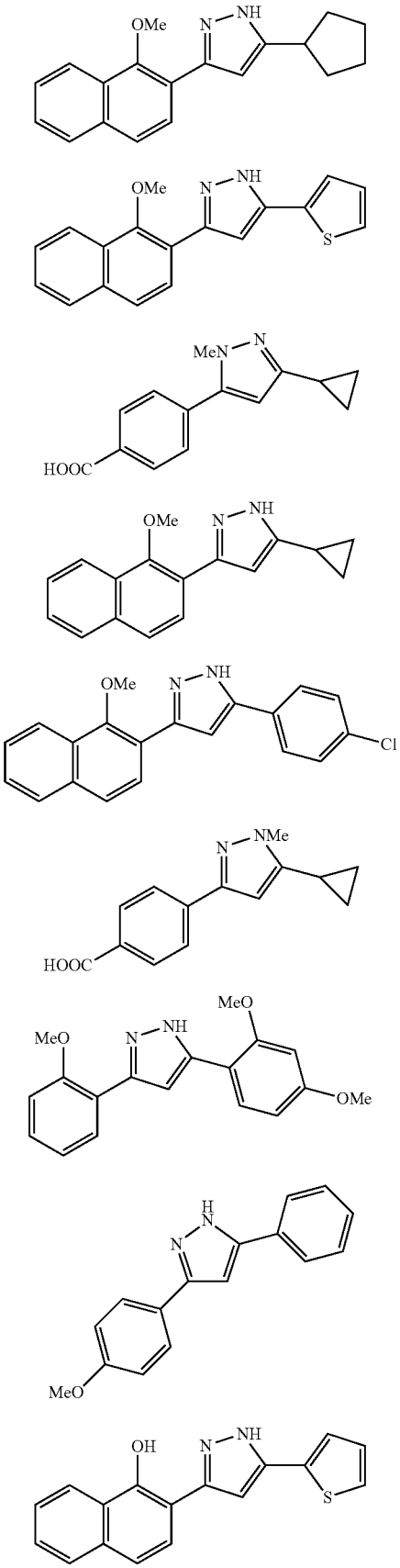

TABLE 1-continued
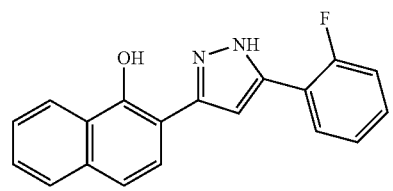 [SMILES: Oc1c(-c2cc(-c3ccccc3F)[nH]n2)ccc2ccccc12]
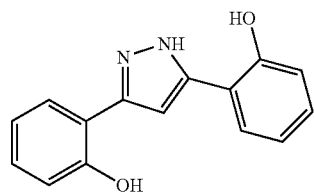 [SMILES: Oc1ccccc1-c1cc(-c2ccccc2O)[nH]n1]
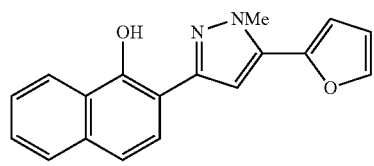 [SMILES: Cn1nc(-c2ccc3ccccc3c2O)cc1-c1ccco1]
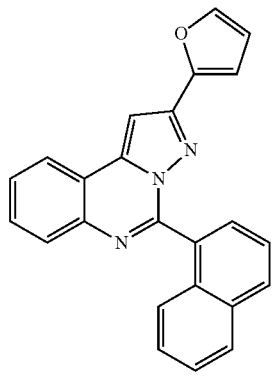 [SMILES: c1coc(-c2cc3c4ccccc4nc(-c4cccc5ccccc45)n3n2)c1]
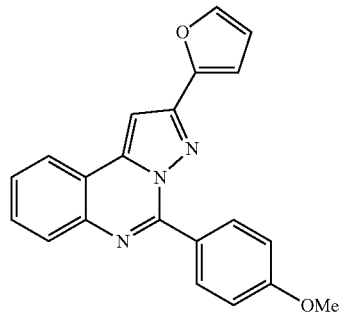 [SMILES: COc1ccc(-c2nc3ccccc3c3cc(-c4ccco4)nn23)cc1]

TABLE 1-continued
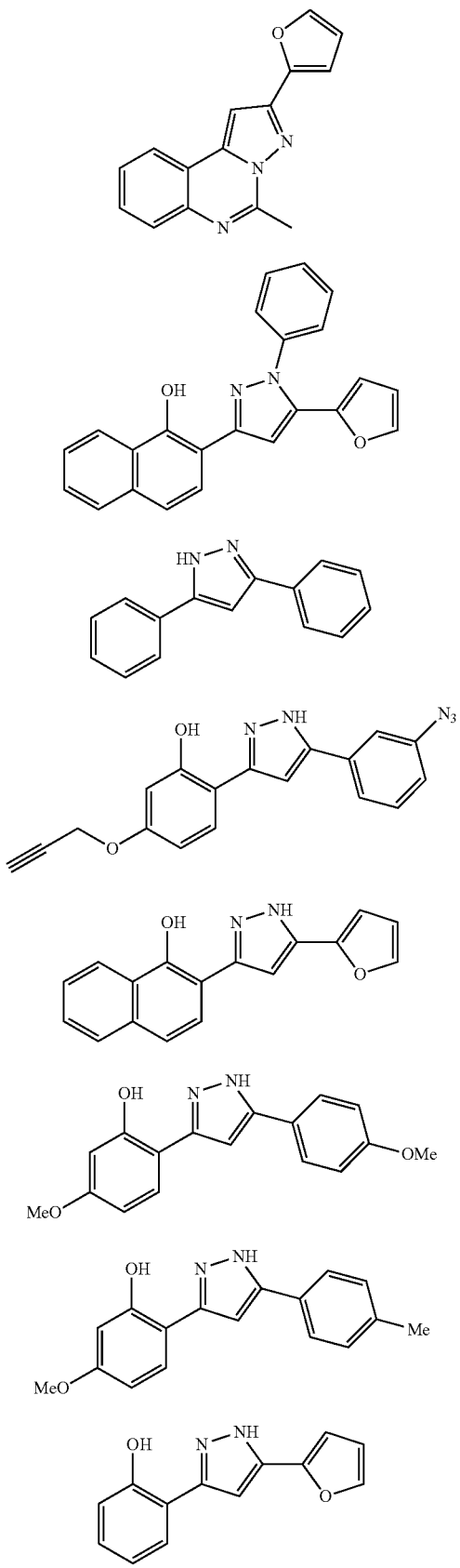

TABLE 1-continued
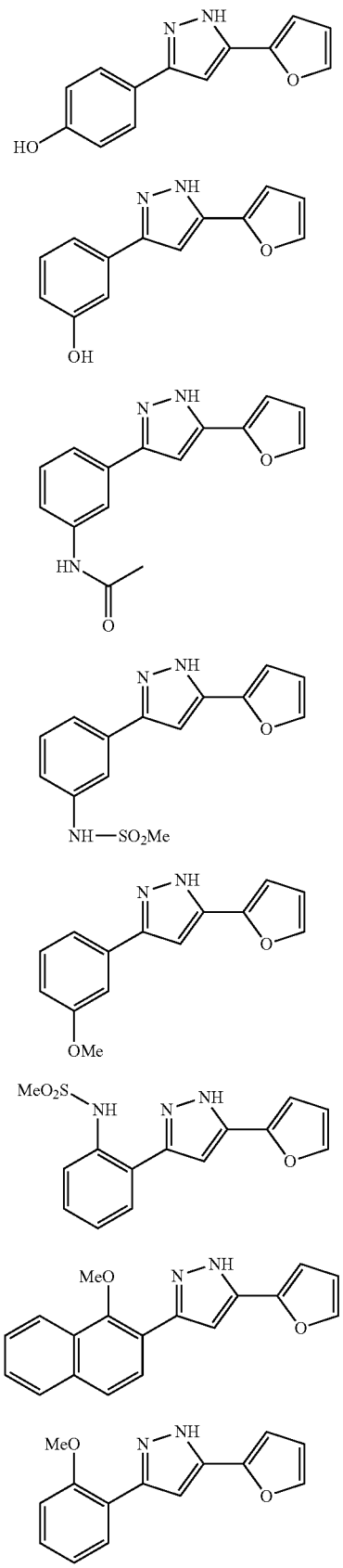

TABLE 1-continued
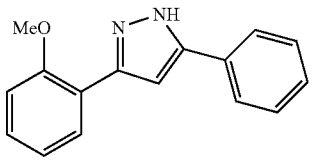 [SMILES: COc1ccccc1-c1cc(-c2ccccc2)[nH]n1]
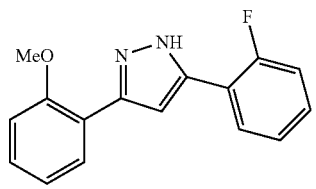 [SMILES: COc1ccccc1-c1cc(-c2ccccc2F)[nH]n1]
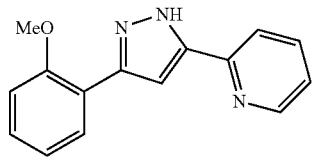 [SMILES: COc1ccccc1-c1cc(-c2ccccn2)[nH]n1]
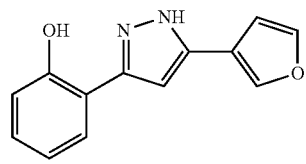 [SMILES: Oc1ccccc1-c1cc(-c2ccoc2)[nH]n1]
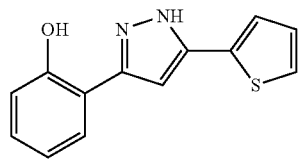 [SMILES: Oc1ccccc1-c1cc(-c2cccs2)[nH]n1]
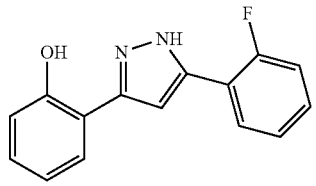 [SMILES: Oc1ccccc1-c1cc(-c2ccccc2F)[nH]n1]
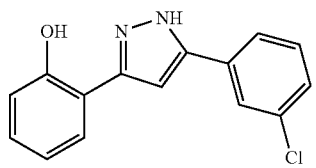 [SMILES: Oc1ccccc1-c1cc(-c2cccc(Cl)c2)[nH]n1]
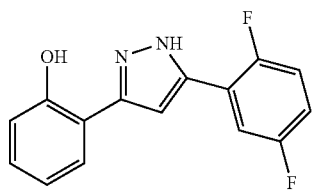 [SMILES: Oc1ccccc1-c1cc(-c2cc(F)ccc2F)[nH]n1]

TABLE 1-continued
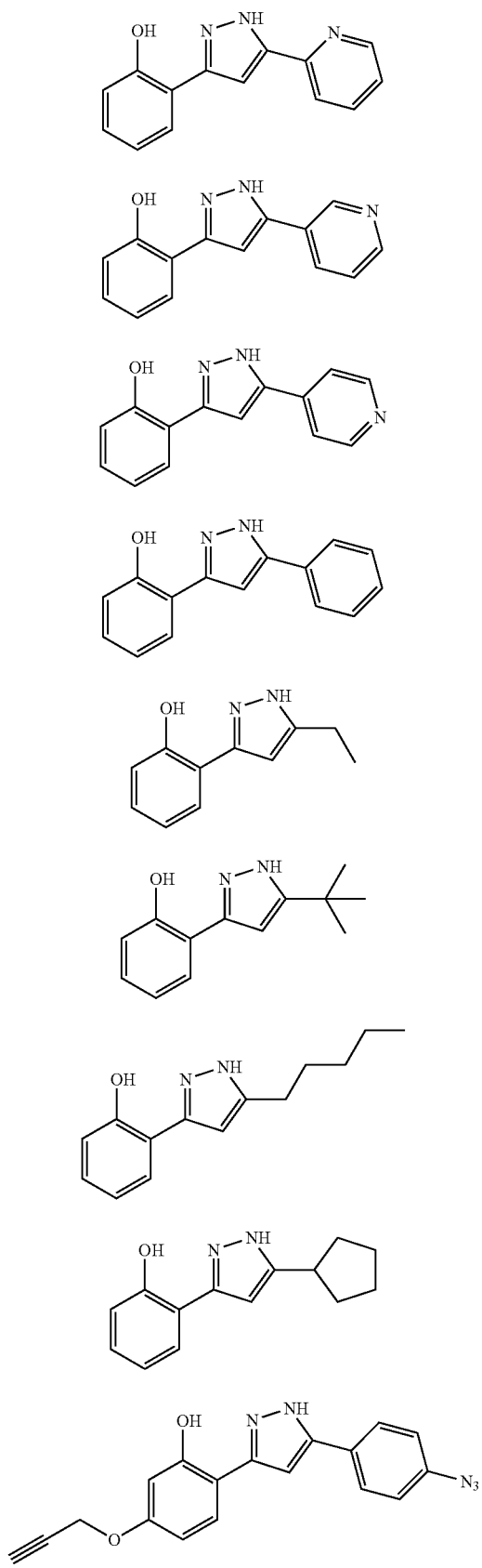

TABLE 1-continued
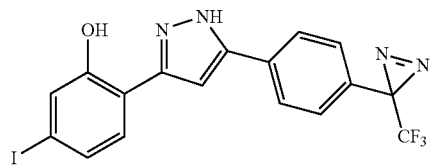 [SMILES: Oc1cc(I)ccc1-c1cc(-c2ccc(C3(C(F)(F)F)N=N3)cc2)[nH]n1]
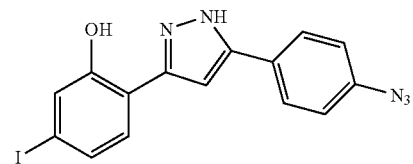 [SMILES: [N-]=[N+]=Nc1ccc(-c2cc(-c3ccc(I)cc3O)n[nH]2)cc1]
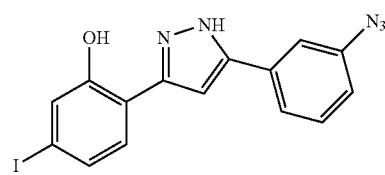 [SMILES: [N-]=[N+]=Nc1cccc(-c2cc(-c3ccc(I)cc3O)n[nH]2)c1]
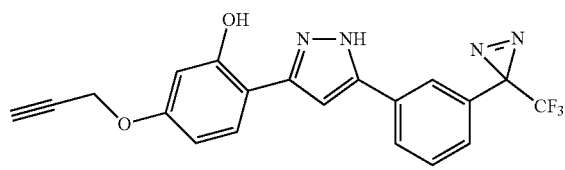 [SMILES: C#CCOc1ccc(-c2cc(-c3cccc(C4(C(F)(F)F)N=N4)c3)[nH]n2)c(O)c1]
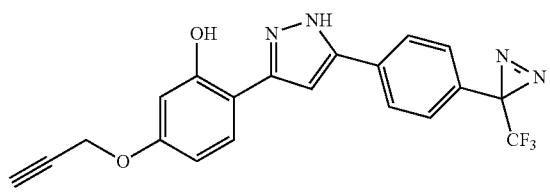 [SMILES: C#CCOc1ccc(-c2cc(-c3ccc(C4(C(F)(F)F)N=N4)cc3)[nH]n2)c(O)c1]
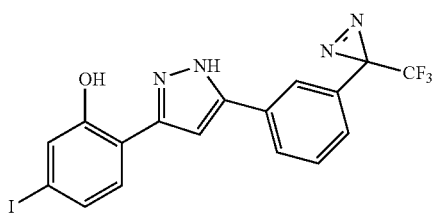 [SMILES: Oc1cc(I)ccc1-c1cc(-c2cccc(C3(C(F)(F)F)N=N3)c2)[nH]n1]
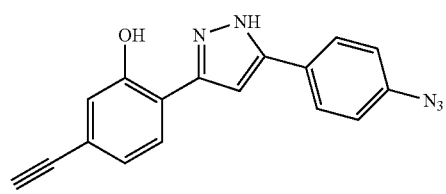 [SMILES: C#Cc1ccc(-c2cc(-c3ccc(N=[N+]=[N-])cc3)[nH]n2)c(O)c1]
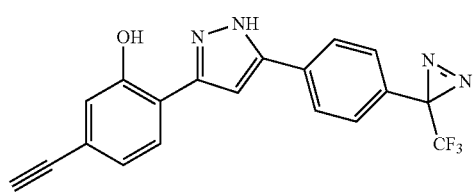 [SMILES: C#Cc1ccc(-c2cc(-c3ccc(C4(C(F)(F)F)N=N4)cc3)[nH]n2)c(O)c1]

TABLE 1-continued
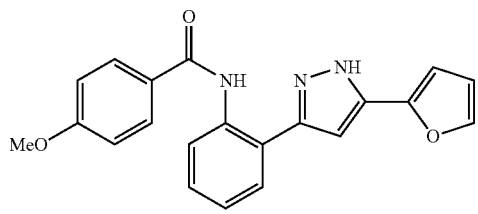 [SMILES: COc1ccc(C(=O)Nc2ccccc2-c2cc(-c3ccco3)[nH]n2)cc1]
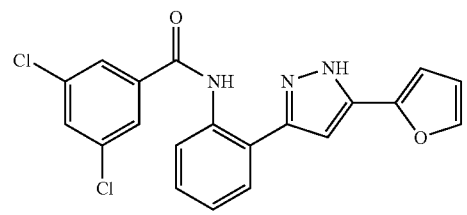 [SMILES: O=C(Nc1ccccc1-c1cc(-c2ccco2)[nH]n1)c1cc(Cl)cc(Cl)c1]
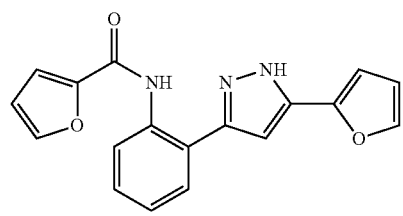 [SMILES: O=C(Nc1ccccc1-c1cc(-c2ccco2)[nH]n1)c1ccco1]
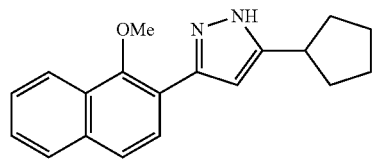 [SMILES: COc1c(-c2cc(C3CCCC3)[nH]n2)ccc2ccccc12]
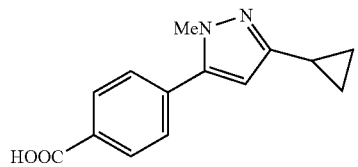 [SMILES: Cn1nc(C2CC2)cc1-c1ccc(C(=O)O)cc1]

TABLE 1-continued
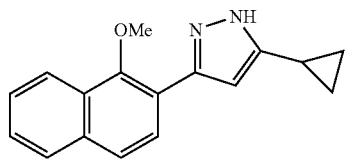 [SMILES: COc1c(-c2cc(C3CC3)[nH]n2)ccc2ccccc12]
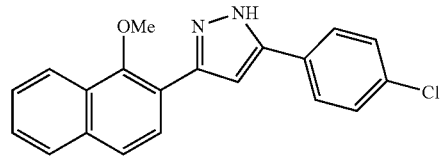 [SMILES: COc1c(-c2cc(-c3ccc(Cl)cc3)[nH]n2)ccc2ccccc12]
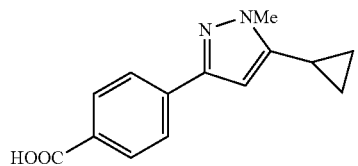 [SMILES: Cn1nc(-c2ccc(C(=O)O)cc2)cc1C1CC1]
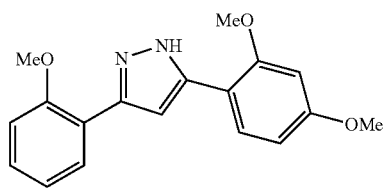 [SMILES: COc1ccc(-c2cc(-c3ccccc3OC)n[nH]2)c(OC)c1]
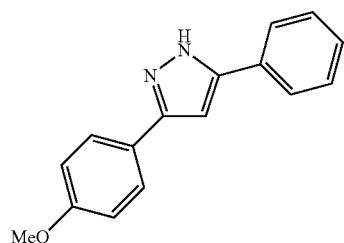 [SMILES: COc1ccc(-c2cc(-c3ccccc3)[nH]n2)cc1]
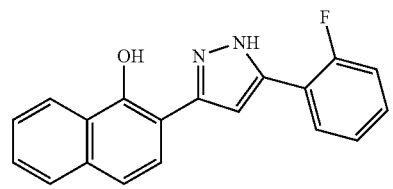 [SMILES: Oc1c(-c2cc(-c3ccccc3F)[nH]n2)ccc2ccccc12]
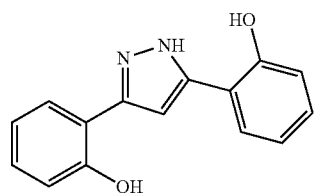 [SMILES: Oc1ccccc1-c1cc(-c2ccccc2O)[nH]n1]

TABLE 1-continued
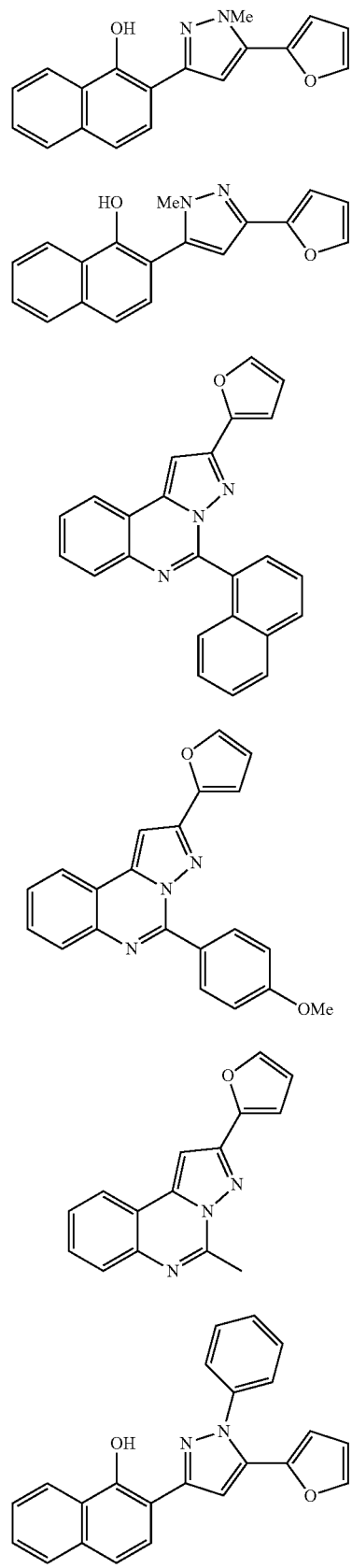

TABLE 1-continued
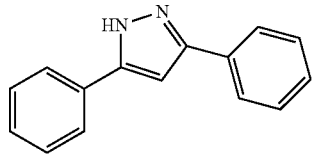 [SMILES: c1ccc(-c2cc(-c3ccccc3)[nH]n2)cc1]
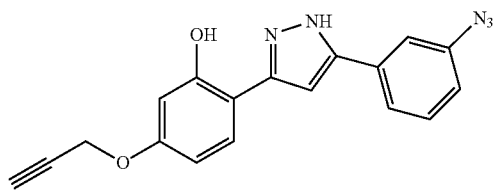 [SMILES: C#CCOc1ccc(-c2cc(-c3cccc(N=[N+]=[N-])c3)[nH]n2)c(O)c1]
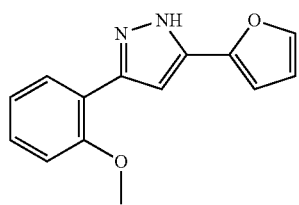 [SMILES: COc1ccccc1-c1cc(-c2ccco2)[nH]n1]
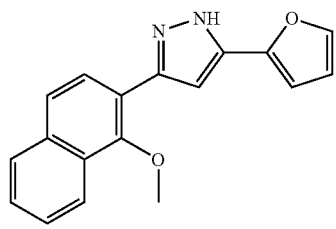 [SMILES: COc1c(-c2cc(-c3ccco3)[nH]n2)ccc2ccccc12]
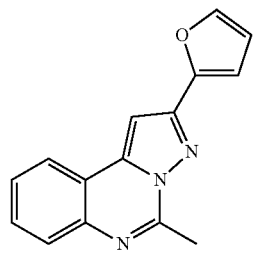 [SMILES: Cc1nc2ccccc2c2cc(-c3ccco3)nn12]
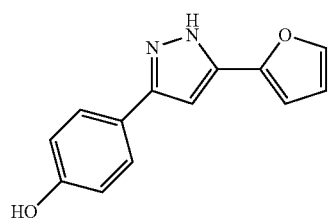 [SMILES: Oc1ccc(-c2cc(-c3ccco3)[nH]n2)cc1]
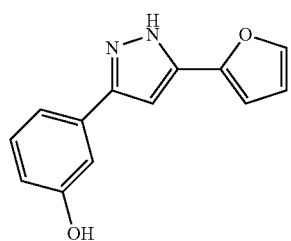 [SMILES: Oc1cccc(-c2cc(-c3ccco3)[nH]n2)c1]

TABLE 1-continued
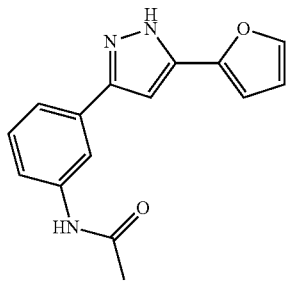 [SMILES: CC(=O)Nc1cccc(-c2cc(-c3ccco3)[nH]n2)c1]
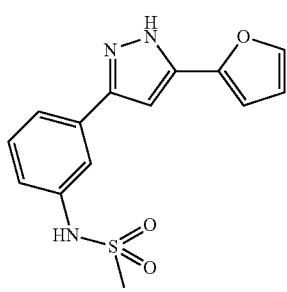 [SMILES: CS(=O)(=O)Nc1cccc(-c2cc(-c3ccco3)[nH]n2)c1]
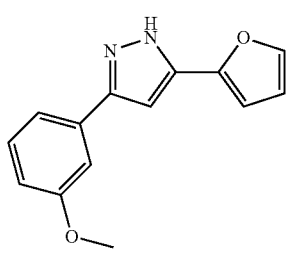 [SMILES: COc1cccc(-c2cc(-c3ccco3)[nH]n2)c1]
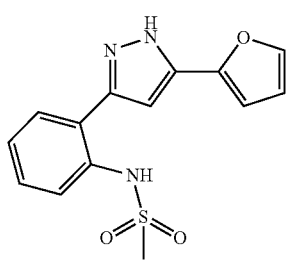 [SMILES: CS(=O)(=O)Nc1ccccc1-c1cc(-c2ccco2)[nH]n1]
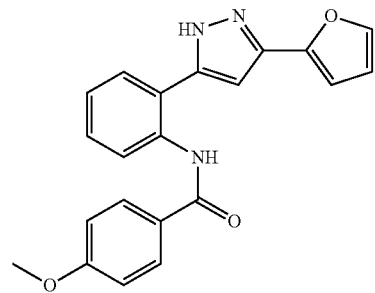 [SMILES: COc1ccc(C(=O)Nc2ccccc2-c2cc(-c3ccco3)n[nH]2)cc1]

TABLE 1-continued
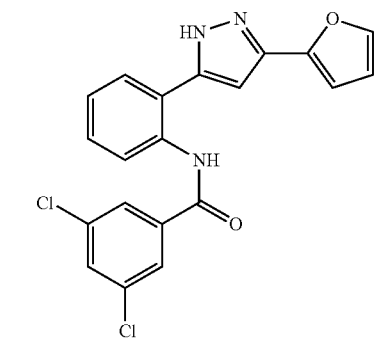 [SMILES: O=C(Nc1ccccc1-c1cc(-c2ccco2)n[nH]1)c1cc(Cl)cc(Cl)c1]
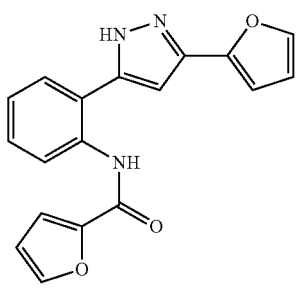 [SMILES: O=C(Nc1ccccc1-c1cc(-c2ccco2)n[nH]1)c1ccco1]
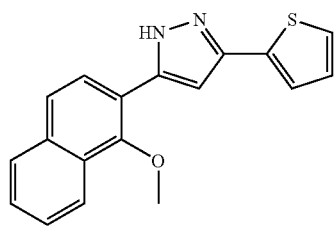 [SMILES: COc1c(-c2cc(-c3cccs3)n[nH]2)ccc2ccccc12]
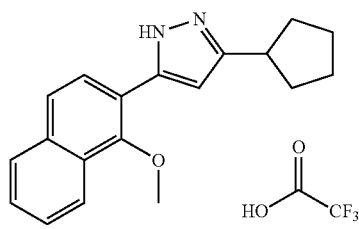
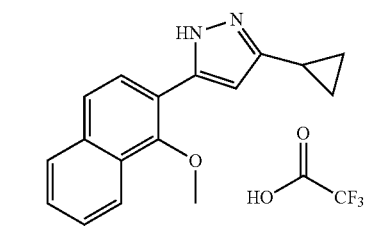
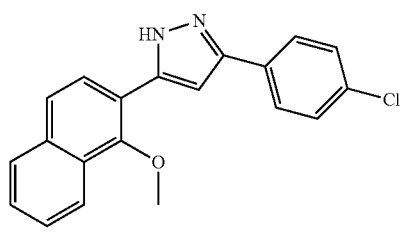 [SMILES: COc1c(-c2cc(-c3ccc(Cl)cc3)n[nH]2)ccc2ccccc12]

TABLE 1-continued
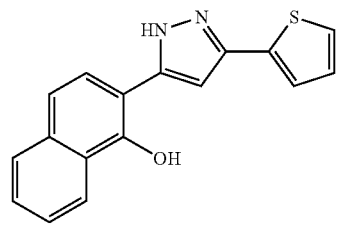 [SMILES: Oc1c(-c2cc(-c3cccs3)n[nH]2)ccc2ccccc12]
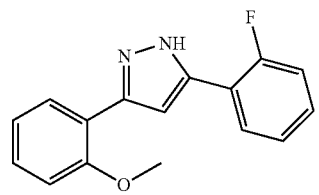 [SMILES: COc1ccccc1-c1cc(-c2ccccc2F)[nH]n1]
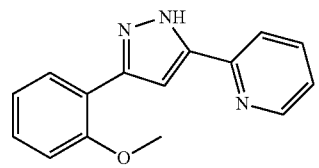 [SMILES: COc1ccccc1-c1cc(-c2ccccn2)[nH]n1]
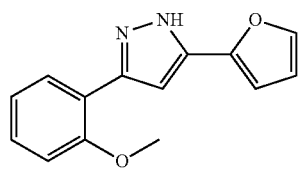 [SMILES: COc1ccccc1-c1cc(-c2ccco2)[nH]n1]
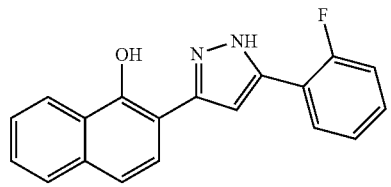 [SMILES: Oc1c(-c2cc(-c3ccccc3F)[nH]n2)ccc2ccccc12]
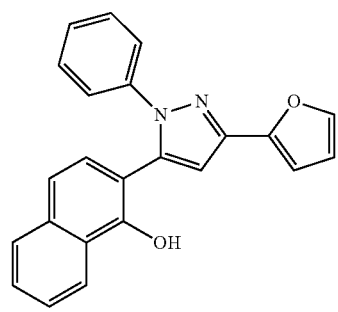 [SMILES: Oc1c(-c2cc(-c3ccco3)nn2-c2ccccc2)ccc2ccccc12]

TABLE 1-continued

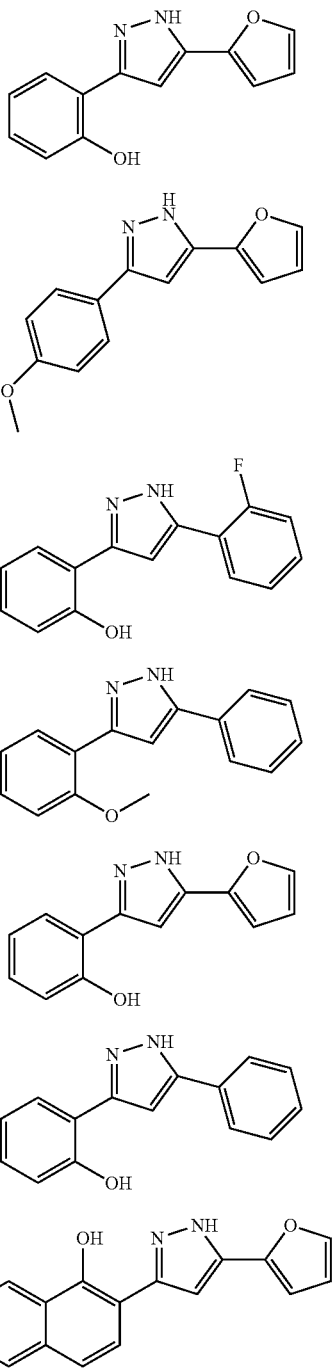

The presently-disclosed subject matter further includes novel compounds, which are included in Table 1.

The presently-disclosed subject matter further includes pharmaceutical compositions including a compound as described above and a pharmaceutically-acceptable carrier.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

The term "ring" includes ring systems. For example, "ring" includes phenyl and napthyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

The terms "alkoxy" and "alkoxyl" as used herein to refer to an alkyl or cycloalkyl group bonded through an ether linkage; that is, an "alkoxy" group can be defined as —OA$^1$ where A$^1$ is alkyl or cycloalkyl as defined above. "Alkoxy" also includes polymers of alkoxy groups as just described; that is, an alkoxy can be a polyether such as —OA$^1$-OA$^2$ or —OA$^1$-(OA$^2$)$_a$-OA$^3$, where "a" is an integer of from 1 to 200 and A$^1$, A$^2$, and A$^3$ are alkyl and/or cycloalkyl groups.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The terms "amine" or "amino" as used herein are represented by a formula NA$^1$A$^2$A$^3$, where A$^1$, A$^2$, and A$^3$ can be, independently, hydrogen or optionally substituted alkyl, cycloalkyl, alkenyl, cycloalkenyl, alkynyl, cycloalkynyl, aryl, or heteroaryl group as described herein.

The term "acetamide" as used herein is represented by a formula A$^1$-NH—CO-A$^1$, or A$^1$-NH—CO-A$^1$-NH—CO-A$^1$, where A$^1$ is hydrogen or optionally substituted alkyl, cycloalkyl, alkenyl, cycloalkenyl, alkynyl, cycloalkynyl, aryl, or heteroaryl group as described herein.

The term "amino sulfonyl" as used herein is represented by a formula A$^1$-NH—SO$_2$-A$^1$, where A$^1$ is hydrogen or optionally substituted alkyl, cycloalkyl, alkenyl, cycloalkenyl, alkynyl, cycloalkynyl, aryl, or heteroaryl group as described herein.

The subject matter disclosed herein is based in part on the present inventors' surprising discovery of compounds that are activators of the enzyme hemY, also known as protoporphyrinogen oxidase (PPO), which catalyzes the production of PPIX (protoporphyrin IX) from PPG IX in one of the final steps in the heme biosynthetic pathway.

The compounds identified herein are contemplated to have further utility in the laboratory setting. Only a limited number (about 10-12) small molecule activators of enzymes have been previously identified, and there is currently no small molecule known that activate the enzyme HemY/PPO, making the identification a small molecule activator of HemY/PPO a notable discovery. Therefore the compounds disclosed herein also hold great promise in the laboratory and research settings.

The presently-disclosed subject matter includes methods for treating a microbial infection in a subject, including administering an effective amount of a compound or composition as disclosed herein, and administering light therapy. Compounds and compositions disclosed herein have antimicrobial activity. As used herein, the term "antimicrobial activity" refers to activity of a compound or composition that inhibits growth of a microbe. The term "microbe" refers to a non-viral pathogen, including all bacterial pathogens.

As used herein, the term "bacterial pathogen" refers to a bacteria capable of causing infection in a subject. In some embodiments, a bacterial pathogen is capable of causing an abscessed tissue. Examples of bacterial pathogens include, but are not limited to, gram positive bacterial pathogens including, *Bacillus anthracis, Enterococcus faecalis, Staphylococcus aureus*, and *Streptococcus pneumonia*; gram negative bacterial pathogens including, *Pseudomonas aeruginosa, Escherichia coli, Salmonella typhimurium*, and *Acinetobacter baumannii*.

The term bacteria or bacterial pathogen further refers to antibiotic-resistant strains of bacterial pathogens, including SCVs. As used herein when referring to a bacterial pathogen, the term "antibiotic-resistant strain" refers to a bacterial pathogen that is capable of withstanding an effect of an antibiotic used in the art to treat the bacterial pathogen (i.e., a non-resistant strain of the bacterial pathogen). For example, *Staphylococcus aureus* can be treated using methicillin; however, an antibiotic-resistant strain of *Staphylococcus aureus* is methicillin-resistant *Staphylococcus aureus* (MRSA).

As used herein, the terms "treatment" or "treating" relate to any treatment of a microbial infection including therapeutic, (i.e., post-infection), and prophylactic treatment, (i.e., pre-infection). As such, the terms treatment or treating include, but are not limited to: preventing a microbial infection or the development of a microbial infection; inhibiting the progression of a microbial infection; arresting or preventing the development of a microbial infection; reducing the severity of a microbial infection; ameliorating or relieving symptoms associated with a microbial infection; causing a regression of a microbial infection or an abscess or one or more of the symptoms associated with a microbial infection; and/or reducing the viability, infectivity and/or virulence of the bacteria. In some cases, in addition to making use of the methods described herein, it can be desirable to make use of traditional and other known treatment protocols. Although such traditional and other known treatment protocols will not be described in any detail herein, they will be known and understood by those skilled in the art, and it is contemplated that such traditional and other known treatment protocols can be used in combination with the methods and compositions described herein, if desired.

As used herein, the term "subject" refers to humans, and other animals. Thus, veterinary treatment is provided in accordance with the presently-disclosed subject matter. As such, the presently-disclosed subject matter provides for the treatment of mammals such as humans, as well as those mammals of importance due to being endangered, such as Siberian tigers; of economic importance, such as animals raised on farms; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Thus, also provided is the treatment of livestock, including, but not limited to, domesticated swine, ruminants, ungulates, horses (including race horses), poultry, and the like.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, the terms "light therapy" and "photo therapy" are used interchangibly to refer to treatment that involves use of light. Various systems, devices, and techniques are known to those of ordinary skill in the art and appropriate selections will be apparent to those of ordinary skill in the art upon study of the present disclosure. Exemplary descriptions relevant to light therapy as contemplated in connection with the presently-disclosed subject matter include, but are not limited to: Fernadez, et al., (2010) "Two Coregulated Efflux Transporters Modulate Intracellular Heme and Protoporphyrin IX Availability in *Streptococcus agalactiae,*" *PLOS Pathogens,* 6(4); Nakonieczna, et al., (2010) "Superoxide dismutase is upregulated in *Staphylo-*

*coccus aureus* following protoporphyrin-mediated photodynamic inactivation and does not directly influence the response to photodynamic treatment," *BMC Microbiology*, 10:323; Morimoto, et al, (2014), "Photodynamic Therapy Using Systemic Administration of 5-Aminolevulinic Acid and a 410-nm Wavelength Light-Emitting Diode for Methicillin-Resistant *Staphylococcus aureus*-Infected Ulcers in Mice," *PLOS ONE*, 9(8). Various photodynamic therapy (PDT) light sources can be used. Examples of PDT light sources are described in U.S. Pat. Nos. 8,175,687, 6,835, 202, 6,645,230; and Patent Application Publication Nos. US2007/0233209 and WO2014/146029, each of which is incorporated herein by this reference. Exemplary light sources for PDT will also be known to those of ordinary skill in the art and include, for example the LEVULAN KARA-STICK® (DUSA Pharmaceuticals, Inc.). Some exemplary light sources will emit violet or blue light. Some exemplary light sources will emit light having wavelengths of about at least about 380, 390, 395, 400, 405, 410, 415, 420, 425, 430, 435, 440, 445, 450, 455, 460, 465, 470, 475, 480, 485, 490, or 495 nm, and up to about 500. Some exemplary light sources will emit light having wavelengths of about less than about 410, 415, 420, 425, 430, 435, 440, 445, 450, 455, 460, 465, 470, 475, 480, 485, 490, 495 nm, or 500 nm, and down to about 380, 390, 395, 400, or 405 nm (inclusive of, for example, 405-410 nm).

The presently-disclosed subject matter further includes kits for use in a method for treating a microbial infection, which can include a compound as disclosed herein, or a pharmaceutical composition including such compound, and further components useful for administrating the compound and administering light therapy. The presently-disclosed subject matter further includes a kit or system that further includes a light source, such as a PDT light source.

The presently-disclosed subject matter further includes methods for activating HemY/PPO in a cell, including contacting the cell with a compound as disclosed herein. In some embodiments the cell is a microbial cell, such as a bacterial cell, an animal cell, such as a human cell.

The presently-disclosed subject matter further includes a method for producing hemoproteins, which involves culturing a cell capable of generating hemoproteins, and contacting the cell with a compound as disclosed herein. While there are known methods for production of hemoproteins, they are often limited by an inability of the producing cell to make enough heme to populate the overexpressed hemoprotein. The compounds as disclosed herein can be used to modify such methods of overexpress hemoproteins of interest, providing sufficient levels of heme to populate the proteins, allowing for enhanced production and purification. The presently-disclosed subject matter further includes a kit for producing hemoproteins, which includes a cell (e.g., cell line, strain) capable of generating hemoproteins; and a compound as disclosed herein. The kit can further include media, reagents, plasmids, constructions, and devices useful for culturing the cell, expressing the protein of interestion, application of the chemical, and/or collection and purification of the hemoprotein of interest. Relevant methods for generating hemoproteins, which can be improved by use of the compounds disclosed herein will be apparent to those of ordinary skill in the art upon studying this disclosure, and the following reference includes relevant information: Villarreal, et al., (2008) "Enhancement of Recombinant Hemoglobin Production in *Escherichia coli* BL21 (DE3) Contianing the *Plesiomonas shigelloides* Heme Transport System," *Applied and Environmental Microbiology*, 74(18): 5854-5856.

The presently-disclosed subject matter further includes a system for screening for activators of HssRS and their targets. Provided is a unique *S. aureus*-based screening system useful for studying the mechanism of activation of the heme-sensing two-component system (TCS), HssRS. The unique system is useful for identifying compounds capable of activating HssRS, and for identifying the target of such compounds within the heme biosynthesis machinery, for example, small molecule targets of enzymes within the heme biosynthetic pathway. Small molecule activators of HssRS, as well as the targets of the small molecules, can be identified using the unique *S. aureus*-based screening system and methods disclosed herein.

When HssRS is stimulated, it induces expression of hrtAB. In the presently-disclosed system, the hrtAB promotor, Phrt, is placed upstream of the *E. coli* toxin, RelE, which impairs translation through mediating cleavage of mRNA, thus leading to growth arrest. The Phrt-RelE construct is inserted in place of the hrtAB locus. When a candidate small molecule that activates HssRS is contacted with a *S. aureus* phrt-relE cell, expression of RelE is induced, leading to cell death. In this manner, cell death allows a candidate small molecule to be identified as a small molecule activators of HssRS. Further, bacteria that survive the otherwise toxic treatment represent spontaneous resistant mutants. These surviving bacteria can be sequenced to identify genetic mutations. The target(s) of the small molecule activator will be the protein(s) containing the mutation(s) identified in the sequencing.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter is further illustrated by the following specific but non-limiting examples. The following examples may include compilations of data that are representative of data gathered at various times during the course of development and experimentation related to the present invention.

EXAMPLES

Example 1: Decoupling Activation of Heme Biosynthesis from Anaerobic Toxicity in Exemplary Compound Active in *S. aureus*

The present inventors developed a high throughput screen for activators of the HssRS two component system. The most active hit compound, 1, was determined to activate HssRS by increasing endogenous heme biosynthesis leading to intracellular accumulation of heme sufficient to activate HssRS but not affect overall growth.[14]

In the course of studying the mechanism of action of 1, it was observed to be toxic to *S. aureus* growing anaerobically, potentially through the inhibition of a process essential during fermentation. *S. aureus* is a facultative anaerobe capable of generating energy through respiration or fermentation depending on the availability of terminal electron acceptors. Fermentative growth of *S. aureus* is significantly inhibited by 1 compared to an untreated control or *S. aureus* treated with 1 under aerobic conditions.[14]

There are no other known reports of molecules with either of these activities. Activators of heme biosynthesis are potentially useful chemical tools to study the regulation of heme biosynthesis in bacteria as little is known regarding the regulation of heme import and biosynthesis. Small molecules toxic to fermenting bacteria may serve as the basis for a new class of therapeutics. During certain types of infections, *S. aureus* relies heavily on fermentation to generate energy. In addition, phenotypic variants of *S. aureus* known as small colony variants (SCVs) are often obligate fermenters and are generally more resistant to current antimicrobial therapies.[15,16,17]

It was initially concluded that these two activities were linked through a single target, given the promiscuous nature of molecules identified through high throughput screens; however, it is possible that these phenotypes are the result of interactions of the same molecule with distinct targets in the bacterium. There is a need for probes with high target specificity as well as activity in chemical biology.[18]

A library of compounds was synthesized around the scaffold of 1 and screened for HssRS activation and anaerobic toxicity to determine how chemical modifications affect the two activities. Using this approach, the two activities of 1 have been effectively decoupled and it has been established that it likely has two or more targets. Furthermore, the structural features of 1 that promote one activity over the other have been identified and present derivatives that maintain each activity while introducing higher specificity have been identified.

Methods

Chemical Synthesis.

1. General Procedure:

All non-aqueous reactions were performed in flame-dried flasks under an atmosphere of argon. Stainless steel syringes were used to transfer air- and moisture-sensitive liquids. Reaction temperatures were controlled using a thermocouple thermometer and analog hotplate stirrer. Reactions were conducted at room temperature (rt, approximately 23° C.) unless otherwise noted. Flash column chromatography was conducted using silica gel 230-400 mesh. Analytical thin-layer chromatography (TLC) was performed on E. Merck silica gel 60 F254 plates and visualized using UV and iodine stain.

2. Materials:

All solvents and chemicals were purchased from Sigma-Aldrich unless otherwise noted. Dry dichloromethane was collected from an MBraun MB-SPS solvent system. N,N-dimethylformamide (DMF), tetrahydrofuran (THF), and acetonitrile (MeCN) were used as received in a bottle with a Sure/Seal. Triethylamine was distilled from calcium hydride and stored over KOH. Deuterated solvents were purchased from Cambridge Isotope Laboratories.

3. Instrumentation:

$^1$H NMR spectra were recorded on Bruker 400, 500, or 600 MHz spectrometers and are reported relative to deuterated solvent signals. Data for $^1$H NMR spectra are reported as follows: chemical shift (δ ppm), multiplicity (s=singlet, d=doublet, t=triplet, q=quartet, p=pentet, m=multiplet, br=broad, app=apparent), coupling constants (Hz), and integration. $^{13}$C NMR spectra were recorded on Bruker 100, 125, or 150 MHz spectrometers and are reported relative to deuterated solvent signals. Low resolution mass spectrometry (LRMS) was conducted and recorded on an Agilent Technologies 6130 Quadrupole instrument.

4. Synthetic Procedures and Compound Characterization Data:

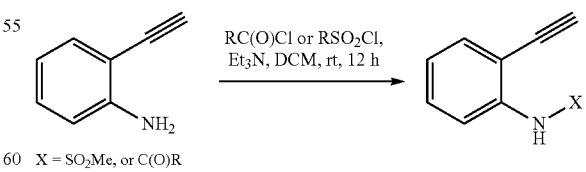

X = SO$_2$Me, or C(O)R 2-ethynyl-N-acylbenzamides

To a stirred solution of 2-ethynylaniline (1 eq) dissolved in dichloromethane (0.3 M) at room temperature was added acyl or sulfonyl chloride (1.0 eq). Triethylamine was slowly added to the reaction and once addition was complete, the reaction was stirred at room temperature overnight. Solvents were removed in vacuo and the residue was partitioned between ethyl acetate and saturated NaHCO₃ (aq), the organic layer dried (MgSO₄), and concentrated in vacuo. The crude product was purified by flash chromatography.

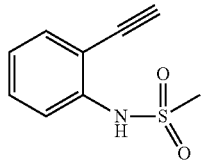

N-(2-ethynylphenyl)methanesulfonamide (S1)

Light brown solid; $^1$H-NMR (400 MHz, CDCl₃) δ 7.61 (d, J=8.20 Hz, 1H) 7.50 (dd, J=7.72 Hz, J=1.40 Hz, 1H), 7.39 (br t, J=7.90 Hz, 1H), 7.13 (t, J=7.67 Hz, 1H), 7.02 (br, 1H), 3.49 (s, 1H), 3.02 (s, 3H); $^{13}$C-NMR (100 MHz, CDCl₃) δ 139.6, 133.0, 130.7, 124.8, 119.6, 113.0, 84.9, 78.8, 39.8; LRMS calculated for C₉H₉NO₂S (M+H)⁺ m/z: 196.0, measured 196.1.

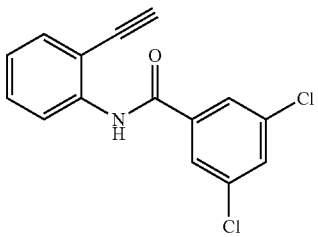 [SMILES: C#Cc1ccccc1NC(=O)c1cc(Cl)cc(Cl)c1]

N-(2-ethynylphenyl)-4-methoxybenzamide (S2)

Off-white solid; $^1$H-NMR (400 MHz, CDCl₃) δ 8.64 (br, 1H), 8.51 (d, J=8.28 Hz, 1H), 7.77 (d, J=1.84 Hz, 2H), 7.57 (t, J=1.86 Hz, 1H), 7.44 (t, J=7.95 Hz, 1H), 7.12 (td, J=7.57 Hz, 1.05 Hz, 1H), 3.64 (s, 1H); $^{13}$C-NMR (100 MHz, CDCl₃) δ 162.7, 139.2, 137.8, 136.0, 132.4, 132.1, 130.6, 125.9, 124.3, 119.6, 111.5, 85.3, 79.4; LRMS calculated for C₁₅H₉Cl₂NO (M+H)⁺ m/z: 290.0, measured 290.0.

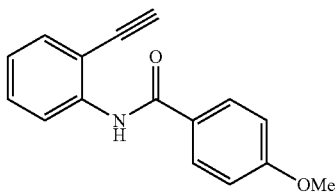 [SMILES: C#Cc1ccccc1NC(=O)c1ccc(OC)cc1]

3,5-dichloro-N-(2-ethynylphenyl)benzamide (S3)

White solid; $^1$H-NMR (400 MHz, CDCl₃) δ 8.72 (br, 1H), 8.59 (d, J=8.20 Hz, 1H), 7.89 (d, J=6.78 Hz, 2H), 7.50 (dd, J=7.68 Hz, 1.48 Hz, 1H), 7.42 (t, J=7.95 Hz, 1H), 7.06 (td, J=7.54 Hz, 1.08 Hz, 1H), 7.00 (d, J=8.84 Hz, 2H), 3.88 (s, 3H), 3.59 (s, 1H); $^{13}$C-NMR (100 MHz, CDCl₃) δ 164.9, 162.8, 140.2, 132.3, 130.5, 129.1, 127.2, 123.3, 119.3, 114.3, 110.9, 84.7, 79.7, 55.6; LRMS calculated for C₁₆H₁₃NO₂ (M+H)⁺ m/z: 252.1, measured 252.1.

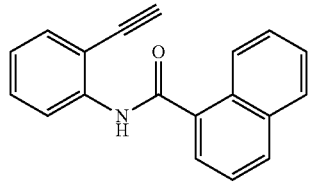 [SMILES: C#Cc1ccccc1NC(=O)c1cccc2ccccc12]

N-(2-ethynylphenyl)-1-naphthamide (S4)

White solid; $^1$H-NMR (400 MHz, CDCl₃) δ 8.71 (d, J=8.20 Hz, 1H), 8.57 (br s, 1H), 8.50 (d, J=8.24 Hz, 1H), 8.00 (d, J=8.00 Hz, 1H), 7.92 (d, J=7.64 Hz, 1H), 7.83 (d, J=7.04 Hz, 1H), 7.63-7.45 (m, 5H), 7.12 (t, J=7.52 Hz, 1H), 3.42 (s, 1H); $^{13}$C-NMR (100 MHz, CDCl₃) δ 167.5, 140.1, 134.3, 134.0, 132.4, 131.6, 130.5, 130.3, 128.6, 127.6, 126.8, 125.6, 125.5, 124.9, 123.8, 119.7, 111.3, 84.9, 79.3; LRMS calculated for C₁₉H₁₃NO (M+H)⁺ m/z: 272.1, measured 272.1.

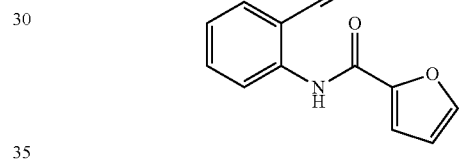

N-(2-ethynylphenyl)furan-2-carboxamide (S5)

Brown solid; $^1$H-NMR (400 MHz, CDCl₃) δ 8.99 (br, 1H), 8.55 (d, J=8.24 Hz, 1H), 7.53 (s, 1H), 7.49 (dd, J=7.68 Hz, 1.48 Hz, 1H), 7.40 (t, J=7.94 Hz, 1H), 7.25 (d, J=3.54 Hz, 1H), 7.06 (t, J=7.71 Hz, 1H), 6.56 (dd, J=3.50 Hz, 1.72 Hz, 1H), 3.60 (s, 1H); $^{13}$C-NMR (100 MHz, CDCl₃) δ 156.1, 148.0, 144.7, 139.4, 132.3, 130.4, 123.6, 119.4, 115.6, 112.7, 111.1, 84.8, 79.1; LRMS calculated for C₁₃H₉NO₂ (M+H)⁺ m/z: 212.1, measured 212.1.

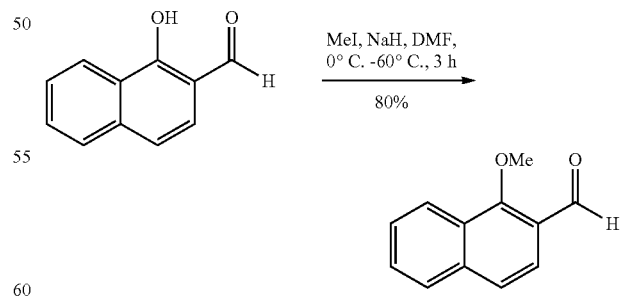

1-methoxy-2-naphthaldehyde (S6)

To a stirred solution of 193 mg (1.12 mmol, 1.0 eq) 1-hydroxy-2-naphthaldehyde (TCI America) dissolved in 5 mL N,N-dimethylformamide at 0° C. was added 49.0 mg (1.23 mmol, 1.2 eq) sodium hydride. The mixture was stirred at 0° C. for 5 min and 140 μL (2.24 mmol, 2.0 eq) methyl iodide was added. The reaction was heated to 60° C. and stirred for 3 h. The reaction was partitioned between ethyl acetate and water, the organic layer washed with water (1×), brine (2×), and dried (MgSO$_4$). The organic layer was concentrated and the residue purified by flash chromatography with a 0-20% ethyl acetate in hexane gradient to provide 165 mg (80%) of product as a light brown solid. $^1$H-NMR (400 MHz, CDCl$_3$) δ 10.59 (d, J=0.76 Hz, 1H), 8.23 (d, J=8.16 Hz, 1H), 7.86-7.82 (m, 2H), 7.64-7.54 (m, 3H), 4.12 (s, 3H); $^{13}$C-NMR (100 MHz) δ 189.6, 162.6, 138.1, 129.4, 128.4, 127.9, 126.9, 124.9, 124.7, 123.2, 122.7, 65.7; LRMS calculated for C$_{12}$H$_{10}$O$_2$ (M+H)$^+$ m/z: 1187.1, measured 187.1.

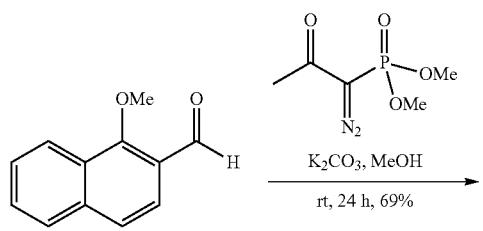

2-ethynyl-1-methoxynaphthalene (S7)

To a stirred solution of 106 mg (0.570 mmol, 1.0 eq) 1-methoxy-2-naphthaldehyde in 5 mL methanol was added 158 mg (1.14 mmol, 2.0 eq) potassium carbonate followed by 131 mg (0.682 mmol, 1.2 eq) dimethyl (1-diazo-2-oxopropyl)phosphonate. The suspension was stirred for 24 h. The reaction was partitioned between ethyl acetate and water, the aqueous layer extracted with ethyl acetate (2×), the organics combined and washed with brine (1×), dried (MgSO$_4$), and flash filtered through silica with 5:1 hexane/ethyl acetate to provide 72 mg (69%) 2-ethynyl-1-methoxynaphthaldehyde. $^1$H-NMR (400 MHz, CDCl$_3$) δ 8.01-7.97 (m, 1H), 7.62-7.58 (m, 1H), 7.35-7.27 (m, 4H), 3.97 (s, 3H), 3.22 (s, 1H); $^{13}$C-NMR (100 MHz, CDCl$_3$) δ 159.3, 144.2, 134.9, 129.8, 127.9, 127.4, 126.5, 123.5, 122.5, 110.3, 82.5, 80.8, 61.9; LRMS calculated for C$_{13}$H$_{10}$O (M+H)$^+$ m/z: 183.1, measured 183.1.

The alkyne precursor for 3a and 3b was prepared from o-anisole as previously described.[1]

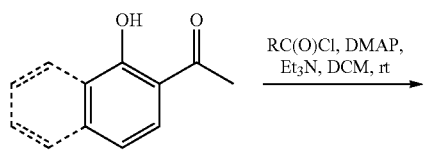

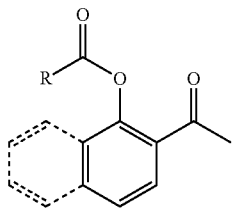

2'-acyloxyacetophenone Synthesis

To a stirred solution of 2'-hydroxyacetophenone in dichloromethane (0.2 M) was added triethylamine (1.1 eq) and 4-dimethylaminopyridine (0.05 eq). The solution was cooled to 0° C. in an ice bath and acid chloride (1.1 eq) was added. The reaction was allowed to warm to room temperature and monitored by TLC and LCMS. When starting material was completely consumed and product observed by LC-MS, the reaction was partitioned between dichloromethane and saturated NaHCO$_3$ (aq). The organic layer was washed with brine and dried (MgSO$_4$), filtered, and concentrated. The products generally did not require further purification but may be crystallized from hexane/ethyl acetate or purified by flash chromatography as needed. Products were generally carried on uncharacterized.

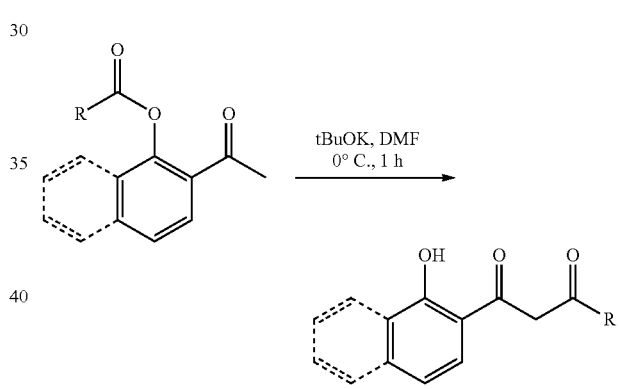

1,3-diketone Synthesis

A suspension of potassium tert-butoxide (2.0 eq) in dimethylformamide (0.2 M) was cooled to 0° C. under Ar. A solution of 2'-acyloxyacetophenone (1.0 eq) in DMF was added dropwise to the tBuOK suspension and stirred at 0° C. until consumption of starting material was observed by TLC (~1 h). The reaction was quenched with 1 N HCl and the resulting suspension extracted with diethyl ether (3×), washed with H$_2$O, brine, dried (MgSO$_4$) and solvents removed in vacuo. Products were carried on crude and uncharacterized.

General Procedure for Demethylation of Aryl Ethers

To a solution of reactant in dichloromethane (0.20 M) was added 6.0 eq BBr$_3$ (1.0 M in dichloromethane) in a microwave vial. The vial was sealed and maintained at 90° C. under microwave irradiation for 20 min. The reaction was quenched with saturated NaHCO$_3$ and extracted with dichloromethane. The organic layer was washed with brine, dried (MgSO$_4$), and concentrated. Products were purified by flash chromatography or HPLC.

1 and 2e were previously reported.[2]

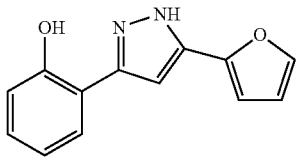 [SMILES: Oc1ccccc1-c1cc(-c2ccco2)[nH]n1]

2-(5-(furan-2-yl)-1H-pyrazol-3-yl)phenol (1a)

$^1$H-NMR (400 MHz, acetone-d6) δ 7.76 (d, J=7.78 Hz, 1H), 7.72 (s, 1H), 7.22 (t, J=7.73 Hz, 1H), 7.12 (s, 1H), 6.96-6.90 (m, 3H), 6.63 (dd, J=3.39 Hz, 1.86 Hz, 1H); $^{13}$C-NMR (150 MHz, acetone-d6) δ 158.3, 154.6, 144.1, 130.0, 127.6, 120.1, 117.6, 117.5, 112.7, 108.5, 99.2; LRMS calculated for C$_{13}$H$_{11}$N$_2$O$_2$(M+H)$^+$ m/z: 227.1, measure, 227.1.

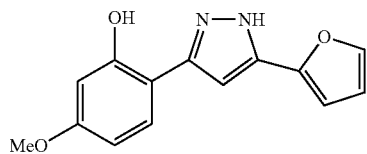 [SMILES: COc1ccc(-c2cc(-c3ccco3)[nH]n2)c(O)c1]

2-(5-(furan-2-yl)-1H-pyrazol-3-yl)-5-methoxyphenol (1b)

$^1$H-NMR (400 MHz, acetone-d6) δ 12.75 (br, 1H), 10.95 (br; 1H), 7.70 (s, 1H), 7.65 (d, J=8.44 Hz, 1H), 7.00 (s, 1H), 6.91 (s, 1H), 6.62 (br, 1H), 6.54-6.48 (m, 2H), 3.80 (s, 3H); $^{13}$C-NMR (100 MHz, acetone-d6) δ 161.9, 158.4, 144.0, 128.5, 112.6, 110.7, 108.3, 106.8, 102.4, 98.5, 55.4; LRMS calculated for C$_{14}$H$_{12}$N$_2$O$_3$ (M+H)$^+$ m/z: 257.1, measured 257.1.

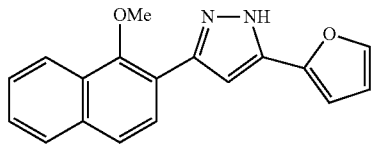 [SMILES: COc1c(-c2cc(-c3ccco3)[nH]n2)ccc2ccccc12]

5-(furan-2-yl)-3-(1-methoxynaphthalen-2-yl)-1H-pyrazole (1c)

$^1$H-NMR (600 MHz, H$_2$O+D$_2$O) δ 8.24 (d, J=8.00 Hz, 1H), 7.97-7.72 (m, 3H), 7.65-7.52 (m, 3H), 7.12 (s, 1H), 6.82 (d, J=2.4 Hz, 1H), 6.58 (s, 1H), 3.87 (s, 3H); $^{13}$C-NMR (150 MHz, CD$_3$OD) δ 154.1, 153.2, 153.1, 142.0, 135.0, 134.9, 128.1, 127.7, 126.4, 126.0, 124.9, 124.0, 122.0, 111.0, 105.7, 103.3, 101.6, 60.5; LRMS calculated for C$_{18}$H$_{14}$N$_2$O$_2$ (M+H)$^+$ m/z: 291.1, measured 291.2.

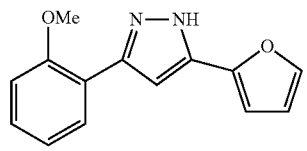 [SMILES: COc1ccccc1-c1cc(-c2ccco2)[nH]n1]

5-(furan-2-yl)-3-(2-methoxyphenyl)-1H-pyrazole (1d)

$^1$H-NMR (400 MHz, CD$_3$OD) δ 7.73 (d, J=7.20 Hz, 1H), 7.57 (s, 1H), 7.38 (t, J=6.8 Hz, 1H), 7.17 (d, J=8.4 Hz, 1H), 7.06 (t, J=7.60 Hz, 1H), 6.94 (s, 1H), 6.76 (d, J=3.20 Hz, 1H), 6.54 (m, 1H), 3.99 (s, 3H); $^{13}$C-NMR (100 MHz, acetone-d6) δ 157.1, 150.3, 142.7, 142.5, 130.2, 128.7, 121.8, 119.3, 112.6, 112.1, 105.9, 101.5, 56.0; LRMS calculated for C$_{14}$H$_{12}$N$_2$O$_2$ (M+H)$^+$ m/z: 241.1, measured 241.1.

3-(5-(furan-2-yl)-1H-pyrazol-3-yl)phenol (1e)

$^1$H-NMR (400 MHz, acetone-d6) δ 7.62 (s, 1H), 7.36-7.31 (m, 2H), 7.26 (t, J=7.77 Hz, 1H), 6.89 (s, 1H), 6.83 (d, J=8.18 Hz, 1H), 6.77 (d, J=3.19 Hz, 1H), 6.56 (dd, J=3.35 Hz, 1.41 Hz, 1H); $^{13}$C-NMR (100 MHz, acetone-d6) δ 158.7, 143.0, 130.7, 117.6, 115.9, 113.2, 112.3, 106.6, 99.9; LRMS calculated for C$_{13}$H$_{10}$N$_2$O$_2$ (M+H)$^+$ m/z: 227.1, measured 227.2.

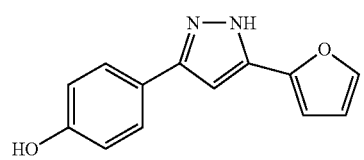 [SMILES: Oc1ccc(-c2cc(-c3ccco3)[nH]n2)cc1]

3-(5-(furan-2-yl)-1H-pyrazol-3-yl)phenol (1f)

$^1$H-NMR (400 MHz, acetone-d6) δ 7.70 (d, J=8.57 Hz, 2H), 7.61 (d, J=1.24 Hz, 1H), 6.92 (d, J=8.57 Hz, 2H), 6.81 (s, 1H), 6.75 (d, J=3.24 Hz, 1H), 6.54 (dd, J=3.24 Hz, 1.24 Hz, 1H); $^{13}$C-NMR (150 MHz, acetone-d6) δ 158.4, 157.3, 149.1, 148.0, 142.8, 127.7, 123.8, 116.5, 112.2, 106.2, 99.0; LRMS calculated for C$_{13}$H$_{10}$N$_2$O$_2$ (M+H)$^+$ m/z: 227.1, measured 227.1.

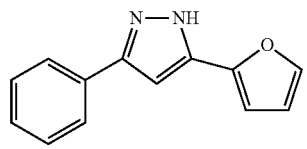 [SMILES: c1ccc(-c2cc(-c3ccco3)[nH]n2)cc1]

5-(furan-2-yl)-3-phenyl-1H-pyrazole (1g)

¹H-NMR (400 MHz, acetone-d6) δ 7.77 (d, J=7.57 Hz, 2H), 7.57 (s, 1H), 7.44 (t, J=7.32 Hz, 2H), 7.35 (t, J=7.28 Hz, 1H), 6.87 (s, 1H), 8.77 (d, J=3.28 Hz, 1H), 6.54 (dd, J=3.28 Hz, 1.48 Hz, 1H); ¹³C-NMR (150 MHz, acetone-d6) δ 143.1, 129.7, 128.8, 126.2, 112.3, 106.7, 9.8; LRMS calculated for $C_{13}H_{10}N_2O$ (M+H)⁺ m/z: 211.1, measured 211.1.

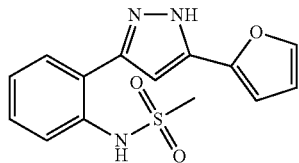 [SMILES: CS(=O)(=O)Nc1ccccc1-c1cc(-c2ccco2)[nH]n1]

N-(2-(5-(furan-2-yl)-1H-pyrazol-3-yl)phenyl)methanesulfonamide (1h)

¹H-NMR (400 MHz, acetone-d6) δ 7.91 (d, J=7.94 Hz, 1H), 7.74 (s, 1H), 7.71 (d, J=7.72 Hz, 1H), 7.22 (t, J=7.60 Hz, 1H), 7.16 (s, 1H), 6.95 (d, J=3.40 Hz, 1H), 6.64 (dd, J=3.40 Hz, 1.80 Hz, 1H), 2.97-2.95 (m, 3H); ¹³C-NMR (100 MHz, acetone-d6) δ 152.6, 145.4, 144.2, 137.0, 136.5, 129.6, 129.1, 124.5, 121.5, 120.3, 112.7, 108.5, 100.7, 39.6; LRMS calculated for $C_{14}H_{13}N_3O_3S$ (M+H)⁺ m/z: 304.1, measured 304.0.

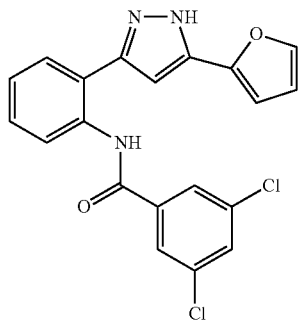 [SMILES: O=C(Nc1ccccc1-c1cc(-c2ccco2)[nH]n1)c1cc(Cl)cc(Cl)c1]

3,5-dichloro-N-(2-(5-(furan-2-yl)-1H-pyrazol-3-yl)phenyl)benzamide (1i)

¹H-NMR (400 MHz, acetone-d6) δ 8.82 (d, J=8.20 Hz, 1H), 8.01 (d, J=1.92 Hz, 2H), 7.93 (dd, J=7.82 Hz, 1.46 Hz, 1H), 7.72 (br s, 2H), 7.39 (br t, J=7.84 Hz, 1H), 7.23 (br t, J=7.58 Hz, 1H), 7.19 (s, 1H), 6.94 (d, J=3.28 Hz, 1H), 6.63 (dd, J=3.40 Hz, 1.84 Hz, 1H); ¹³C-NMR (125 MHz, acetone-d6) 163.2, 145.4, 144.2, 140.0, 137.4, 136.2, 132.0, 129.4, 128.9, 127.0, 124.7, 121.4, 121.3, 112.7, 108.7, 101.2; LRMS calculated for $C_{20}H_{13}Cl_2N_3O_2$ (M+H)⁺ m/z: 398.1, measured 398.0.

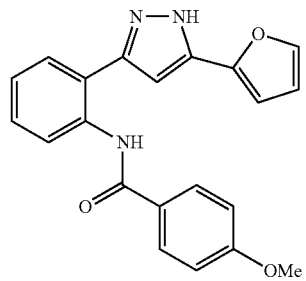 [SMILES: COc1ccc(C(=O)Nc2ccccc2-c2cc(-c3ccco3)[nH]n2)cc1]

N-(2-(5-(furan-2-yl)-1H-pyrazol-3-yl)phenyl)-4-methoxybenzamide (1j)

¹H-NMR (400 MHz, acetone-d6) δ 8.95 (d, J=7.84 Hz, 1H), 8.16 (d, J=8.88 Hz, 2H), 7.90 (d, J=7.84 Hz, 1H), 7.71 (s, 1H), 7.36 (t, J=7.89 Hz, 1H), 7.19-7.14 (m, 2H), 7.05 (d, J=8.89 Hz, 2H), 6.94 (d, J=3.36 Hz, 1H), 6.62 (dd, J=3.38 Hz, 1.82 Hz, 1H), 3.88 (s, 3H); ¹³C-NMR (100 MHz, acetone-d6) δ 165.5, 163.4, 144.1, 138.3, 130.2, 129.3, 128.7, 123.6, 121.1, 114.7, 112.7, 108.5, 101.0, 55.9; LRMS calculated for $C_{21}H_{17}N_3O_3$ (M+H)⁺ m/z: 360.1, measured 360.1.

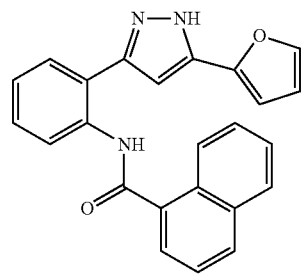 [SMILES: O=C(Nc1ccccc1-c1cc(-c2ccco2)[nH]n1)c1cccc2ccccc12]

N-(2-(5-(furan-2-yl)-1H-pyrazol-3-yl)phenyl)-1-naphthamide (1k)

¹H-NMR (600 MHz, acetone-d6) δ 9.00 (d, J=8.28 Hz, 1H), 8.58-8.53 (m, 1H), 8.10 (d, J=8.24 Hz, 1H), 8.02-7.99 (m, 1H), 7.97 (d, J=7.97 Hz, 1H), 7.92 (dd, J=7.84 Hz, 1.48 Hz, 1H), 7.68 (d, J=1.44 Hz, 1H), 7.64-7.56 (m, 2H), 7.44 (td, J=7.88 Hz, 1.48 Hz, 1H), 7.24 (td, J=7.63 Hz, 0.96 Hz, 1H), 7.14 (s, 1H), 6.90 (d, J=3.36 Hz, 1H), 6.60 (dd, J=3.40 Hz, 1.80 Hz, 1H); ¹³C-NMR (150 MHz, acetone-d6) δ 168.1, 153.0, 145.5, 144.1, 142.3, 138.0, 136.3, 134.9, 131.3, 131.4, 129.3, 129.2, 128.8, 127.7, 127.3, 126.6, 126.4, 126.0, 124.3, 121.3, 112.6, 108.3, 101.1; LRMS calculated for $C_{24}H_{17}N_3O_2$ (M+H)⁺ m/z: 380.1, measured 380.1.

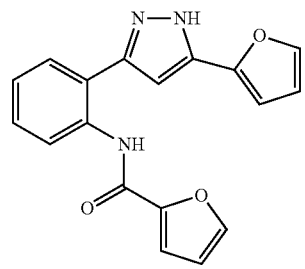 [SMILES: O=C(Nc1ccccc1-c1cc(-c2ccco2)[nH]n1)c1ccco1]

N-(2-(5-furan-2-yl)-1H-pyrazol-3-yl)phenylfuran-2-carboxamide (1l)

¹H-NMR (400 MHz, acetone-d6) δ 8.83 (d, J=4.31 Hz, 1H), 7.89 (dd, J=7.82 Hz, 1.50 Hz, 1H), 7.73 (ddd, J=4.60 Hz, 1.70 Hz, 0.78 Hz, 2H), 7.36 (app t, 1H), 7.26 (dd, J=3.48 Hz, 0.76 Hz, 1H), 7.19 (app t, 1H), 7.15 (s, 1H), 6.95 (dd, J=3.40 Hz, 0.50 Hz, 1H), 6.65 (dd, J=3.48 Hz, 1.76 Hz, 1H), 6.63 (dd, J=3.42 Hz, 1.82 Hz, 1H); ¹³C-NMR (100 MHz, acetone-d6) δ 157.1, 149.8, 145.9, 145.6, 144.0, 137.4, 136.5, 129.2, 128.8, 124.2, 121.3, 121.1, 115.0, 113.0, 112.7, 108.4, 100.9; LRMS calculated for $C_{18}H_{13}N_3O_3$ (M+H)⁺ m/z: 320.1, measured 320.1.

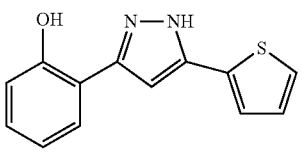 [SMILES: Oc1ccccc1-c1cc(-c2cccs2)[nH]n1]

2-(5-(thiophen-2-yl)-1H-pyrazol-3-yl)phenol (2a)

¹H-NMR (400 MHz, acetone-d6) δ 7.77 (dd, J=7.74 Hz, 1.54 Hz, 1H), 7.56 (br s, 1H), 7.24-7.15 (m, 2H), 7.11 (s, 1H), 6.93 (app q, 2H)¹³C-NMR (150 MHz, acetone-d6) δ 157.3, 153.5, 139.2, 130.0, 128.9, 127.4, 127.0, 119.3, 117.5, 116.8, 99.5; LRMS calculated for $C_{13}H_{10}N_2OS$ (M+H)⁺ m/z: 243.1, measured 243.1.

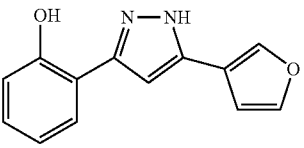 [SMILES: Oc1ccccc1-c1cc(-c2ccoc2)[nH]n1]

2-(5-furan-3-yl)-1H-pyrazol-3-yl)phenol (2b)

¹H-NMR (400 MHz, acetone-d6) δ 8.13 (s, 1H), 7.73-7.69 (m, 2H), 7.20 (app tr, 1H), 7.07 (s, 1H), 6.96-6.87 (m, 3H); ¹³C-NMR (100 MHz, acetone-d6) δ 157.1, 145.2, 141.0, 129.9, 127.5, 120.0, 117.7, 117.5, 109.4, 100.0; LRMS calculated for $C_{13}H_{10}N_2O_2$ (M+H)⁺ m/z: 243.1, measured 243.0.

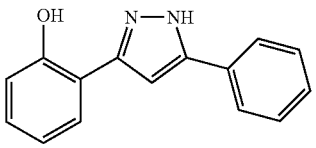 [SMILES: Oc1ccccc1-c1cc(-c2ccccc2)[nH]n1]

2-(5-phenyl-1H-pyrazol-3-yl)phenol (2c)

¹H-NMR (400 MHz, acetone-d6) δ 7.91-7.87 (m, 2H), 7.78 (dd, J=7.74 Hz, 1.62 Hz, 1H), 7.52 (t, J=7.54 Hz, 2H), 7.43 (t, J=7.38 Hz, 1H), 7.27 (s, 1H), 7.21 (app t, 1H), 6.96-6.90 (m, 2H); ¹³C-NMR (150 MHz, acetone-d6) δ 157.2, 153.8, 144.7, 130.0, 129.9, 129.7, 127.6, 126.5, 120.0, 117.7, 117.5, 100.1; LRMS calculated for $C_{15}H_{12}N_2O$ (M+H)⁺ m/z: 237.1, measured 237.1.

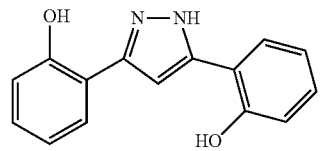 [SMILES: Oc1ccccc1-c1cc(-c2ccccc2O)[nH]n1]

2,2'-(1H-pyrazole-3,5-diyl)diphenol (2d)

¹H-NMR (400 MHz, CD₃OD) δ 7.71 (d, J=7.52 Hz, 2H), 7.19 (t, J=7.58 Hz, 2H), 7.14 (s, 1H), 6.97-6.89 (m, 4H); ¹³C-NMR (100 MHz, CD₃OD) δ 156.4, 130.2, 128.3, 120.7, 117.8, 117.4, 100.4; LRMS calculated for $C_{15}H_{12}N_2O_2$ (M+H)⁺ m/z: 253.1, measured 253.2.

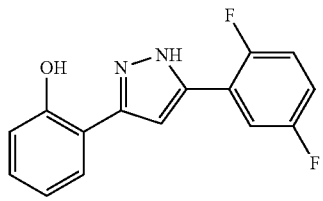 [SMILES: Oc1ccccc1-c1cc(-c2cc(F)ccc2F)[nH]n1]

2-(5-(2,5-difluorophenyl)-1H-pyrazol-3-yl)phenol (2f)

¹H-NMR (600 MHz, acetone-d6) δ 9.12 (br s, 1H), 8.62 (br s, 1H), 8.24 (dd, J=7.89 Hz, 1.88 Hz, 1H), 7.79 (dd, J=7.74 Hz, 1.56 Hz, 1H), 7.51 (dd, J=7.59 Hz, 4.83 Hz, 1H), 7.38 (s, 1H), 7.23 (app t, 1H), 6.97 (d, J=8.10 Hz, 1H), 6.94 (t, J=7.30 Hz, 1H); ¹³C-NMR (150 MHz, acetone-d6) δ 156.9, 150.5, 147.8, 133.5, 130.1, 129.9, 128.1, 127.8, 124.7, 120.2, 118.5, 117.6, 117.5, 100.8; LRMS calculated for $C_{15}H_{10}F_2N_2O$ (M+H)⁺ m/z: 273.1, measured 273.1.

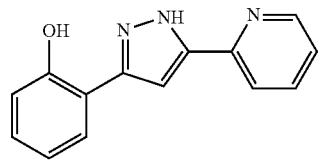 [SMILES: Oc1ccccc1-c1cc(-c2ccccn2)[nH]n1]

2-(5-pyridin-2-yl)-1H-pyrazol-3-yl)phenol (2g)

¹H-NMR (400 MHz, acetone-d6) δ 10.93 (br s, 1H), 8.66 (d, J=4.64 Hz, 1H), 8.00 (m, 2H), 7.78 (dd, J=7.72 Hz, 1.56 Hz, 1H), 7.47 (s, 1H), 7.39 (app t, 1H), 7.22 (app t, 1H), 6.97-6.90 (m, 2H); ¹³C-NMR (150 MHz, acetone-d6) δ 150.5, 138.2, 129.9, 127.5, 124.4, 121.3, 120.0, 117.7, 117.6, 100.8; LRMS calculated for $C_{16}H_{11}N_3O$ (M+H)⁺ m/z: 238.1, measured 238.1.

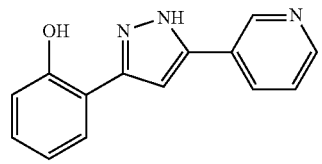 [SMILES: Oc1ccccc1-c1cc(-c2cccnc2)[nH]n1]

2-(5-(pyridin-3-yl)-1H-pyrazol-3-yl)phenol (2h)

¹H-NMR (400 MHz, acetone-d6) δ 9.12 (s, 1H), 8.62 (br s, 1H), 8.24 (dt, J=7.96 Hz, 1.92 Hz, 1H), 7.80 (dd, J=7.76 Hz, 1.60 Hz, 1H), 7.51 (br, 1H), 7.38 (br s, 1H), 7.25-7.20 (m, 1H), 7.01-6.91 (m, 2H); ¹³C-NMR (150 MHz, DMSO-d6) δ 148.3, 146.4, 132.2, 129.2, 127.5, 123.9, 116.3, 101.4; LRMS calculated for $C_{14}H_{11}N_3O$ (M+H)⁺ m/z: 238.1, measured 238.1.

2-(5-pyridin-4-yl)-1H-pyrazol-3-yl)phenol (2i)

¹H-NMR (600 MHz, DMSO-d6) δ 8.62 (d, J=4.80 Hz, 2H), 7.81 (app d, 2H), 7.72 (d, J=7.32 Hz, 1H), 7.39 (br, 1H), 7.20 (app t, 1H), 6.99 (d, J=7.80 Hz, 1H), 6.92 (app t, 1H); ¹³C-NMR (150 MHz, DMSO-d6) δ 154.5, 150.2, 129.3, 127.3, 119.5, 119.4, 116.4, 102.2; LRMS calculated for $C_{14}H_{11}N_3O$ (M+H)⁺ m/z: 238.1, measured 238.1.

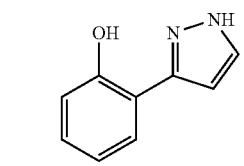 [SMILES: Oc1ccccc1-c1cc[nH]n1]

2-(1H-pyrazol-3-yl)phenol (2j)

¹H-NMR (400 MHz, acetone-d6) δ 11.01 (s, 1H), 7.90 (d, J=2.36 Hz, 1H), 7.72 (d, J=7.64 Hz, 1H), 7.19 (t, J=7.64 Hz, 1H), 6.96-6.85 (m, 3H); ¹³C-NMR (100 MHz, acetone-d6) δ 157.0, 130.7, 129.7, 127.4, 127.2, 119.9, 117.9, 117.5, 102.3; LR7MS calculated for $C_9H_8N_2O$ (M+H)⁺ m/z: 161.1, measured 161.2.

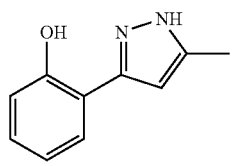

2-(5-methyl-1H-pyrazol-3-yl)phenol (2k)

¹H-NMR (600 MHz, acetone-d6) δ 11.07 (s, 1H), 7.63 (dd, J=7.74 Hz, J=1.50 Hz, 1H), 7.16 (t, J=7.50 Hz, 1H), 6.89 (d, J=8.16 Hz, 1H), 6.86 (t, J=7.50 Hz, 1H), 6.58 (s, 1H), 2.39 (s, 3H); ¹³C-NMR (150 MHz, acetone-d6) δ 157.2, 129.5, 127.3, 119.8, 118.0, 117.4, 101.6, 10.6; LRMS calculated for $C_{10}H_{10}N_2O$ (M+H)⁺ m/z: 175.1, measured 175.2.

2-(5-ethyl-1H-pyrazol-3-yl)phenol (2l)

¹H-NMR (600 MHz, acetone-d6) δ 12.13 (br s, 1H), 11.09 (br s, 1H), 7.56 (J=7.70 Hz, 1.58 Hz, 1H), 7.16 (app tr, 1H), 6.87 (app q, 1H), 6.62 (s, 1H), 2.79 (q, J=7.60 Hz, 2H), 1.32 (t, J=7.60 Hz, 3H); ¹³C-NMR (150 MHz, acetone-d6) δ 157.2, 152.8, 147.4, 129.5, 127.3, 119.8, 118.1, 117.4, 117.3, 100.1, 19.3, 13.7; LRMS calculated for $C_{11}H_{12}N_2O$ (M+H)⁺ m/z: 189.1, measured 189.2.

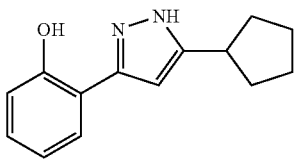 [SMILES: Oc1ccccc1-c1cc(C2CCCC2)[nH]n1]

2-(5-(tert-butyl)-1H-pyrazol-3-yl)phenol (2m)

¹H-NMR (600 MHz, acetone-d6) δ 7.68 (dd, J=7.72 Hz, 1.60 Hz, 1H), 7.16 (app t, 1H), 6.91-6.84 (m, 1H), 6.65 (s, 1H), 1.42 (s, 9H); ¹³C-NMR (150 MHz, acetone-d6) δ 157.2, 155.0, 152.4, 129.4, 127.3, 119.6, 118.1, 117.4, 117.3, 98.6, 31.7, 30.4; LRMS calculated for $C_{13}H_{16}N_2O$ (M+H)⁺ m/z: 217.1, measured 217.1.

2-(5-cyclopentyl-1H-pyrazol-3-yl)phenol (2n)

¹H-NMR (400 MHz, acetone-d6) δ 12.13 (br, 1H), 11.09 (s, 1H), 7.66 (dd, J=7.72 Hz, 1.60 Hz, 1H), 7.16 (app t, 1H), 6.91-6.83 (m, 1H), 6.64 (s, 1H), 3.22 (p, J=7.98 Hz, 1H), 2.19-2.10 (m, 2H), 1.85-1.66 (m, 6H); ¹³C-NMR (150 MHz, acetone-d6) δ 157.4, 152.7, 150.2, 129.5, 127.4, 119.6, 118.2, 117.8, 99.5, 33.8, 26.3, 25.7; LRMS calculated for $C_{14}H_{16}N_2O$ (M+H)⁺ m/z: 229.1, measured 229.2.

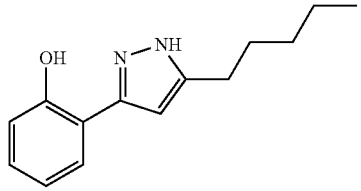 [SMILES: CCCCCc1cc(-c2ccccc2O)n[nH]1]

2-(5-pentyl-1H-pyrazol-3-yl)phenol (2o)

¹H-NMR (400 MHz, acetone-d6) δ 7.65 (dd, J=7.70 Hz, 1.56 Hz, 1H), 7.17 (app t, 1H), 6.91-6.84 (m, 1H), 6.62 (m, 1H), 2.76 (t, J=7.66 Hz, 2H), 1.74 (br p, 2H), 1.40-1.33 (m, 4H), 0.90 (t, J=7.06 Hz, 3H)¹³C-NMR (150 MHz, acetone-d6) δ 157.2, 152.9, 146.0, 129.5, 127.3, 119.8, 118.1, 117.4, 100.6, 41.4, 32.1, 25.9, 23.0, 14.2; LRMS calculated for C₁₄H₁₈N₂O (M+H)⁺ m/z: 231.2, measured 231.2.

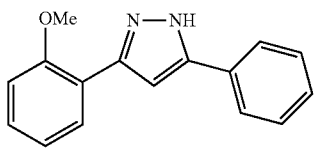 [SMILES: COc1ccccc1-c1cc(-c2ccccc2)[nH]n1]

3-(2-methoxyphenyl)-5-phenyl-1H-pyrazole (3a)

¹H-NMR (400 MHz, acetone-d6) δ 7.92 (app d, 2H), 7.87 (app d, 1H), 7.41 (t, J=7.64 Hz, 2H), 7.38-7.27 (m, 2H), 7.20-7.15 (m, 2H), 7.06 (app t, 1H), 4.04 (s, 3H); ¹³C-NMR (150 MHz, acetone-d6) δ 157.1, 130.1, 129.4, 128.7, 128.2, 126.2, 121.8, 112.6, 101.6, 56.0; LRMS calculated for C₁₆H₁₄N₂O (M+H)⁺ m/z: 251.1, measured 251.2.

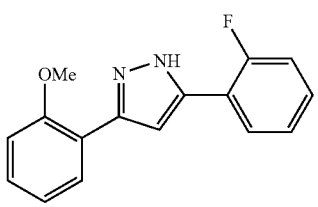 [SMILES: COc1ccccc1-c1cc(-c2ccccc2F)[nH]n1]

5-(2-fluorophenyl)-3-(2-methoxyphenyl)-1H-pyrazole (3b)

¹H-NMR (400 MHz, acetone-d6) δ 8.09 (br, 1H), 7.85 (d, J=6.84 Hz, 1H), 7.39-7.33 (m, 2H), 7.28-7.17 (m, 3H), 7.16 (d, J=3.60 Hz, 1H), 7.07 (t, J=7.47 Hz, 1H), 4.04 (s, 3H); ¹³C-NMR (150 MHz, acetone-d6); δ 157.1, 130.2, 130.0, 129.8, 129.2, 129.1, 128.7, 125.2, 121.9, 116.9, 112.6, 104.7, 56.0; LRMS calculated for C₁₆H₁₃FN₂O (M+H)⁺ m/z: 269.1, measured 269.1.

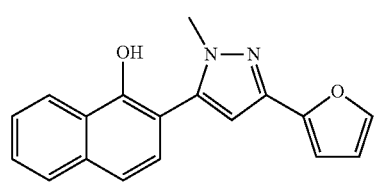 [SMILES: Cn1nc(-c2ccco2)cc1-c1ccc2ccccc2c1O]

2-(3-(furan-2-yl)-1-methyl-1H-pyrazol-5-yl)naphthalen-1-ol (4a)

¹H-NMR (400 MHz, acetone-d6) δ 8.66 (br, 1H), 8.40-8.36 (m, 1H), 7.95-7.90 (m, 1H), 7.62-7.52 (m, 4H), 7.34 (d, J=8.44 Hz, 1H), 6.70 (d, J=3.80 Hz, 1H), 6.58 (s, 1H), 6.54 (dd, J=3.28 Hz, 1.80 Hz, 1H), 3.77 (s, 3H); ¹³C-NMR (150 MHz, acetone-d6) δ 151.6, 150.6, 143.7, 142.5, 141.4, 136.1, 128.8, 128.6, 127.9, 126.5, 126.2, 123.4, 120.6, 112.1, 111.9, 105.6, 104.9, 37.5; LRMS calculated for C₁₈H₁₅N₂O₂ (M+H)⁺ m/z: 291.1, measured 291.2.

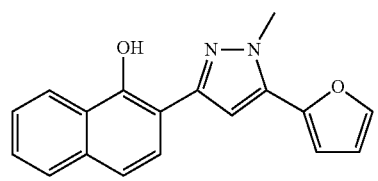 [SMILES: Cn1nc(-c2ccc3ccccc3c2O)cc1-c1ccco1]

2-(5-(furan-2-yl)-1-methyl-1H-pyrazol-3-yl)naphthalen-1-ol (4b)

¹H-NMR (600 MHz, acetone-d6) δ 8.36-8.33 (m, 1H), 7.84-7.80 (m, 2H), 7.50 (dt, J=9.72 Hz, 3.36 Hz, 2H), 7.45 (d, J=8.52 Hz, 1H), 7.17 (s, 1H), 6.98 (d, J=3.78 Hz, 1H), 6.69 (dd, J=3.42 Hz, 1.80 Hz, 1H), 4.21 (s, 3H); ¹³C-NMR (150 MHz, acetone-d6) δ 152.6, 151.4, 145.0, 144.6, 136.2, 135.1, 128.3, 127.4, 126.3, 126.0, 124.9, 123.5, 119.7, 112.7, 110.7, 110.4, 102.1, 39.2; LRMS calculated for C₁₈H₁₅N₂O₂ (M+H)⁺ m/z: 291.1, measured 291.2.

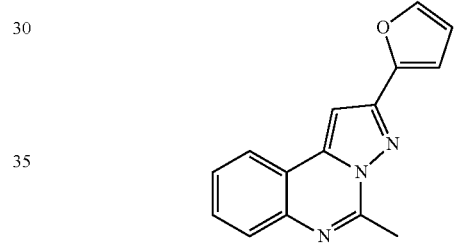

2-(furan-2-yl)-5-methylpyrazolo[1,5-c]quinazoline (5a)

¹H-NMR (400 MHz, acetone-d6) δ 8.24 (app dd, 1H), 7.86 (d, J=7.61 Hz, 1H), 7.65-7.64 (m, 1H), 7.71 (app td, 1H), 7.63 (app t, 1H), 7.49 (s, 1H), 7.06 (d, J=3.42 Hz, 1H), 6.65 (dd, J=3.36 Hz, 1.80 Hz, 1H), 2.94 (s, 3H); ¹³C-NMR (150 MHz, acetone-d6) δ 149.1, 148.9, 147.5, 144.3, 140.9, 140.7, 130.6, 128.7, 127.9, 124.2, 120.0, 112.4, 109.3, 96.1, 95.9; LRMS calculated for C₁₅H₁₁N₃O (M+H)⁺ m/z: 250.1, measured 250.1.

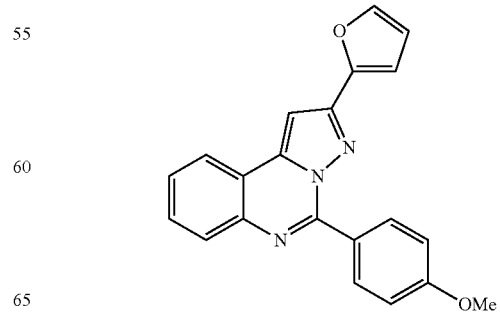

2-(furan-2-yl)-5-(4-methoxyphenyl)pyrazolo[1,5-c]quinazoline (5b)

$^1$H-NMR (400 MHz, acetone-d6) δ 8.69 (d, J=9.04 Hz, 2H), 8.28 (dd, J=7.88 Hz, 1.12 Hz, 1H), 7.96 (d, J=8.16 Hz, 1H), 7.77-7.71 (m, 2H), 7.64 (app t, 1H), 7.56 (s, 1H), 7.15 (d, J=9.04 Hz, 2H), 7.07 (d, J=3.33 Hz, 1H), 6.65 (dd, J=3.36 Hz, 1.80 Hz, 1H), 3.95 (s, 3H); $^{13}$C-NMR (100 MHz, acetone-d6) δ 163.0, 147.5, 142.7, 141.0, 133.5, 130.9, 129.2, 128.3, 124.2, 114.1, 112.7, 109.5, 96.0, 55.9; LRMS calculated for $C_{21}H_{15}N_3O_2$ (M+H)$^+$ m/z: 342.1, measured 342.1.

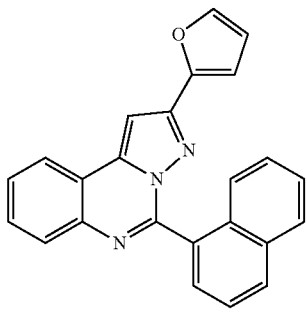 [SMILES: c1coc(-c2cc3c4ccccc4nc(-c4cccc5ccccc45)n3n2)c1]

2-(furan-2-yl)-5-(naphthalen-1-yl)pyrazolo[1,5-c]quinazoline (5c)

$^1$H-NMR (600 MHz, acetone-d6) δ 8.16 (d, J=7.80 Hz, 1H), 8.07 (app dd, 2H), 7.96 (app dd, 2H), 7.75-7.64 (m, 4H), 7.52 (t, J=7.50 Hz, 1H), 7.49 (s, 1H), 7.42 (t, J=7.62 Hz, 1H), 7.35 (s, 1H), 6.79 (d, J=3.18 Hz, 1H), 6.45 (br s, 1H); $^{13}$C-NMR (150 MHz, acetone-d6) δ 148.5, 147.8, 147.7, 143.4, 141.3, 139.6, 133.9, 131.5, 131.2, 130.4, 129.8, 128.7, 128.6, 128.5, 128.4, 127.0, 126.4, 125.4, 125.1, 123.4, 119.6, 111.9, 109.3, 95.9; LRMS calculated for $C_{24}H_{15}N_3O$ (M+H)$^+$ m/z: 362.1, measured 362.1.

Pyrazole Synthesis.

ROUTE 1: To a stirred solution of terminal alkyne (1 eq) in THF (0.2 M) was added triethylamine (3 eq), bistriphenylphosphine palladium dichloride (0.05 eq), copper(I) iodide (0.1 eq), and acid chloride (1.5 eq) at room temperature. The reaction was stirred until conversion of starting material was observed by TLC. The reaction was diluted 1:1 with acetonitrile followed by addition of hydrazine hydrate (4 eq). The reaction was stirred until complete as determined by TLC. The reaction was filtered through celite, concentrated, and purified by preparative scale reverse phase HPLC.

ROUTE 2: To a solution of crude diketone in ethanol (0.25 M) in a microwave vial was added hydrazine hydrate (2 eq). The vial was sealed and heated to 150° C. in a microwave reactor for 5 min. The reaction was concentrated and the product was purified by preparative scale reverse phase HPLC.

XylE Assay.

Previously reported strains were used.[11] Cultures grown overnight in 5 ml TSB with 10 μg mL$^{-1}$ chloramphenicol for 15-18 h were subcultured 1:100 into 0.5 mL TSB with 10 μg mL$^{-1}$ chloramphenicol containing compound and incubated at 37° C., 180 rpm for 6 h. Cells were washed and lysed as previously described. 200 μL of a 200 μM catechol solution in 100 mM potassium phosphate (pH 8.0) was added to 20 μL of lysate and the oxidation of catechol was followed by monitoring absorbance at 375 nm for 10 min. Samples were normalized to protein concentration as determined by BCA assay (Pierce).

HssRS Activation Dose Response Curves and EC$_{50}$ Determination.

The above XylE procedure was followed using different concentrations of compound. The data were then entered into Graphpad Prism 6 and fit to a curve to determine EC$_{50}$ values.

IC50 Determination.

Cultures of wild type *S. aureus* strain Newman and ΔmenB[14] were grown in aeration tubes aerobically at 37° C. with shaking for 15-18 h. Anaerobic cultures were prepared by growing bacteria at 37° C. without shaking in an anaerobic chamber for 15-18 h. Bacteria from each condition were subcultured 1:100 into TSB containing various concentrations of compound in a 96 well plate. Aerobic wild type and ΔmenB plates are incubated aerobically at 37° C. with shaking while anaerobic plates were grown in an anaerobic chamber (Coy) at 37° C. without shaking. The absorbance at 600 nm (OD$_{600}$) was determined after 9 h of growth and the fraction of growth at each compound concentration is determined by dividing the OD$_{600}$ by the vehicle control (DMSO) value. IC$_{50}$s were calculated using Graphpad Prism 6 and errors are reported as 95% confidence intervals.

Heme Adaptation Assays.

Overnight cultures of *S. aureus* were subcultured into 500 μL TSB containing compound in 1.5 mL tubes and incubated at 37° C. with shaking for 15 h. Bacteria from the compound treated cultures were then subcultured 1:100 into 100 μL TSB containing heme and incubated at 37° C. with shaking for 8 h. Growth was monitored by reading the OD$_{600}$ on a Biotek microplate reader at the defined time intervals.

Iron Chelation Assay.

Iron chelation by 1 was characterized using the CAS assay. Solutions were prepared as described.[21] The clinical iron chelator deferasirox (AK Scientific) was used as a control. Samples were incubated in 1 mL cuvettes at room temperature for 30 min after addition of compound. The maximum concentration of compound used was 30 μM which is a 4:1 stoichiometry of 1 to Chromeazural-S. Absorbance at 630 nm was measured on a Varian UV/Vis spectrophotometer.

Results and Discussion

Library Synthesis.

Figure 2A:
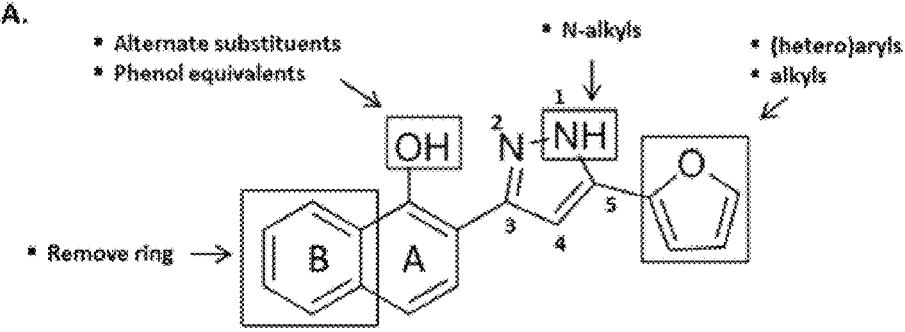
FIG. 2A. Illustration of derivatization strategy to study structure-activity relationships for 1.

The initial efforts towards varying the structure of 1 focused on four regions of the molecule (FIG. 2A); removal of the B ring of the naphthol moiety; modification of the phenol by walking to the m- and p-positions (with B ring removed), O-methylation, and replacement with phenol equivalents (amides and sulfonamide); N-methylation of the pyrazole; and replacement of the furan with aromatic, heteroaromatic, and alkyl groups.

Figure 2B:
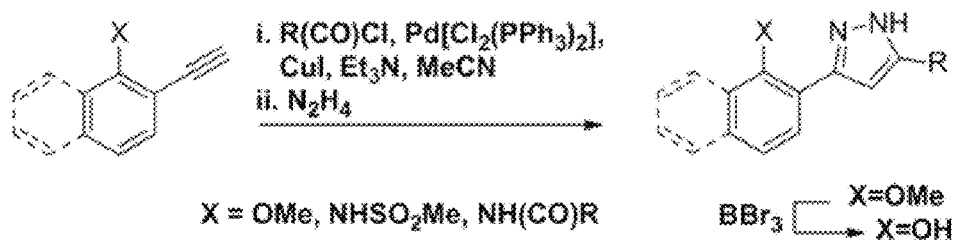
FIG. 2B. Synthetic methods utilized to access derivatives for library generation. Et$_3$N=triethyl amine, MeCN=acetonitrile, Me=methyl, tBuOK=potassium tert-butoxide, DMF=N,N-dimethylformamide, EtOH=ethanol.
Figure 2B:
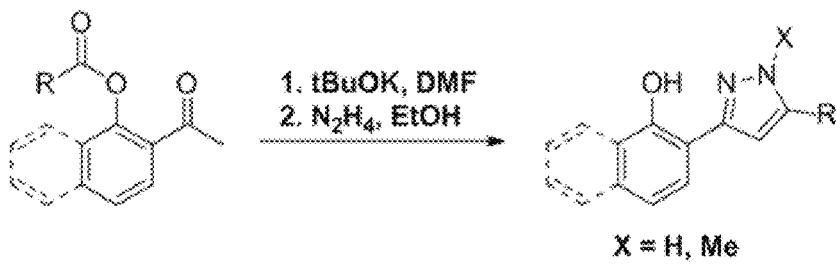
Figure 3:
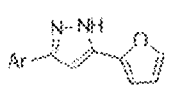
FIG. 3. Analogs of 1 synthesized for studies set forth in the Examples.
Figure 3:
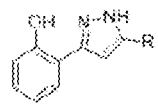

Many routes to 3,5-substituted pyrazoles have been reported.[19] We utilized two routes, 1) cyclocondensation of hydrazine with an alkynone and 2) cyclocondensation of hydrazine with a 1,3-diketone (FIG. 2B). The alkynone can be installed by palladium-mediated coupling with the acid chloride containing the corresponding 5-position substituent. This route requires methyl ether protection of the phenol. As such, synthesis of free phenol containing compounds involves subsequent deprotection with boron tribromide. For this reason, this sequence was primarily utilized to synthesize the amide, sulfonamide, and O-methylated derivatives of 1 (FIG. 3; 1c, 1d, 1h-1l, 3a, and 3b). The amide derivatives were quite labile in the presence of acid, particularly when substituted with small R groups (Me), and underwent further dehydration to generate 2,5-substituted pyrazolo[1,5-c]quinazolines (Supporting information, 5a-5c). These compounds will not be discussed due to their divergence from the optimization plan.

Using route 2, the 5-position was diversified by acylating the 2'-phenol of the corresponding acetophenone to generate the ester substrate for an intramolecular Claisen condensation to provide the 1,3-diketone. Compounds 2a-c, 2e-i, and 2k-o were afforded by cyclocondensation with hydrazine. 2d was prepared by acylating 2'-hydroxyacetophone with 2-methoxybenzoyl chloride, carrying the ester through this reaction sequence, and subsequently removing the methyl group using boron tribromide. 2j was synthesized by reacting hydrazine with the corresponding chromone under the same conditions as the cyclocondensation. Using an analogous reaction sequence but acylating 3'- and 4'-hydroxyacetophenone allowed synthesis of 1e and 1f. Compound 1g was prepared by intermolecular Claisen condensation of the lithium enolate of acetophenone, prepared by reaction with LHMDS in toluene, with furoyl chloride to provide the 1,3-diketone. Methylation of the pyrazole nitrogen was achieved by reaction of the intermediate 1,3-diketone with methylhydrazine followed by HPLC separation of the resulting isomeric pyrazoles 4a and 4b.

Figure 8:
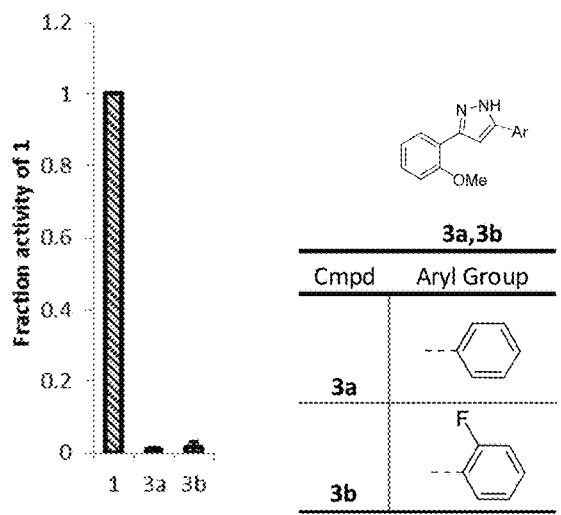
FIG. 8. Activation of HssRS by 3a and 3b at 50 µM. Activity is presented as the fraction of activation by the indicated derivative relative to 1 at 50 µM. Data are the average of three replicates. Error bars represent one standard deviation from the mean.

HssRS activation. The library was screened for activation of the heme stress response as an indicator for activation of heme biosynthesis in *S. aureus*. We began by screening at the single point concentration of 50 μM using a previously described reporter assay (FIG. 4).[11] In this assay, Newman harboring a plasmid with the hrt promoter fused to xylE, a gene encoding a catechol oxidase, is treated with compound for six hours, the bacteria lysed, and the oxidation of catechol by XylE quantified by spectrophotometry. An increase in absorbance due to the oxidation of catechol indicates elevated levels of xylE transcription and hrt promoter activity. Results are expressed as the fraction of activation of HssRS by the compound compared to 1. An arbitrary cut-off of 0.05 was chosen to define active vs. inactive compounds. With reference to FIG. 8, activation of HssRS by 3a and 3b at 50 μM. Activity is presented as the fraction of activation by the indicated derivative relative to 1 at 50 μM.

Replacement of the naphthol substituent with phenol (1a) or 4-methoxyphenol (1b) resulted in a modest loss of activity compared to 1, but still retained significant ability to activate HssRS. O- and N-methylation of 1 (1c, 4a and 4b) resulted in complete loss of activity. These data suggest that disruption of the hydrogen bonding properties of 1 has a significant effect on its ability to activate heme biosynthesis. To test this further, several modifications to the phenol of 1a were made. O-methylation (1d), movement to m- or p-positions (1e and 1f), removal (1g), and replacement with a methyl sulfonamide (1h) or various aryl or heteroaryl amides (1i-1l) resulted in a loss of HssRS activation compared to 1 and 1a. This suggests that the ortho-OH is required for activity.

To explore modification at the 5-position, we chose the o-hydroxyphenyl substituent at the 3-position instead of the o-hydroxynaphthyl of the parent molecule for convenience. Replacement of the furan with hydrogen (2j), alkyl (2k-2o) or pyridyl (2g-2i) substituents eliminates activity compared to 1 and 1a. The furan can be replaced with several aromatic or heteroaromatic groups and retain considerable activity. In particular, replacement of the furan with an unsubstituted phenyl group, 2c, seems to restore activity comparable to 1 without the presence of the naphthol B-ring. However, fluorination of 2c decreases activity though 2e and 2f are comparable to 1a in activity. Substitution with hydroxyl at the ortho position of the phenyl ring of 2c to provide 2d renders the molecule toxic under the single point assay conditions and is therefore not included in FIG. 4. However, 2d activates HssRS at lower concentrations and its activity was explored further.

Figure 9:
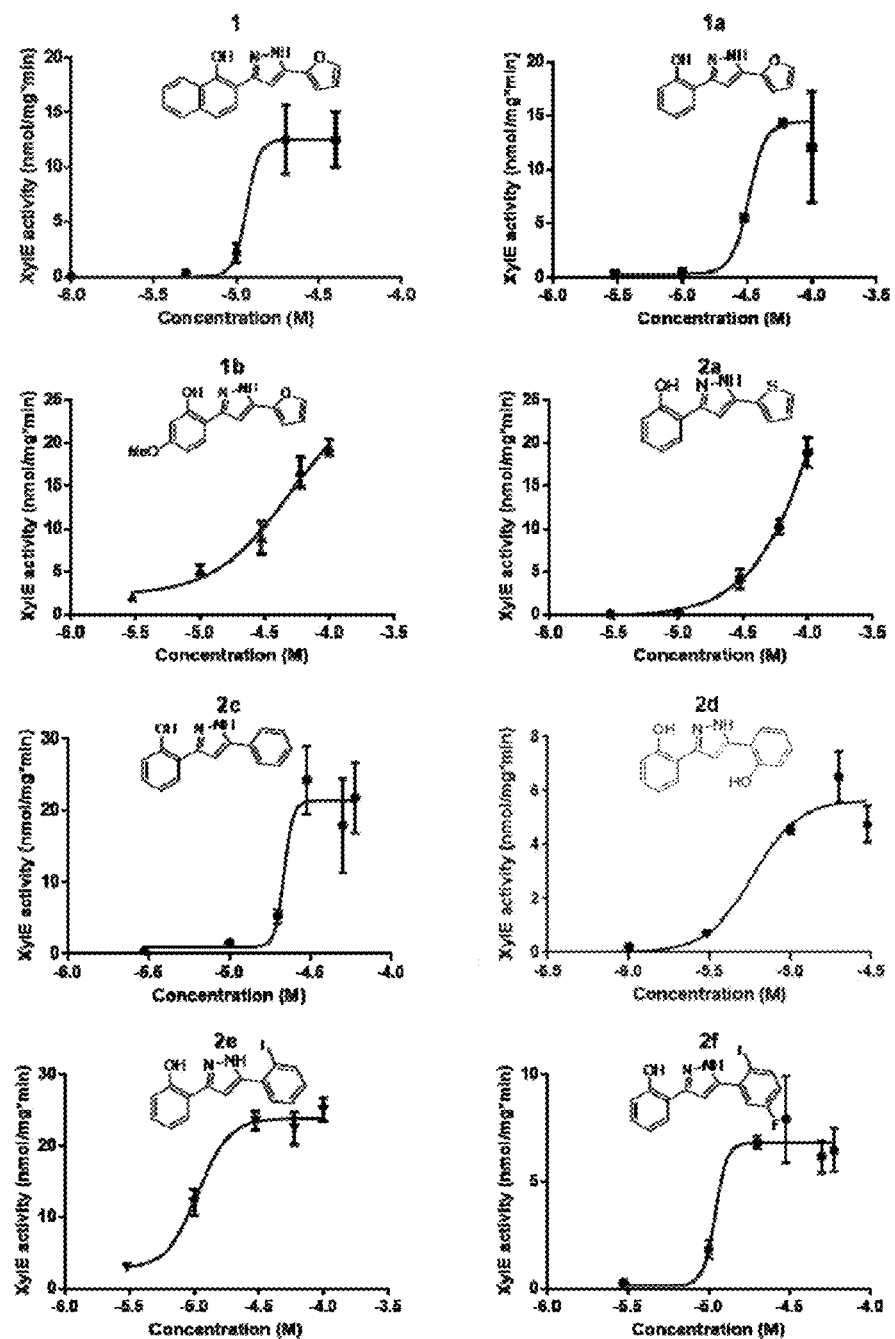
FIG. 9 Concentration response curves for 1 and the six derivatives active in the single point screen; 1a, 1b, 2a, 2c, 2d, and 2e. Data were collected using the XylE assay and are the average of three replicates. Error bars are one standard deviation from the mean.

Concentration response curves for the top six activators from the single point screen (1a, 1b, 2a, 2c, 2e, and 2f) and 2d were generated to determine $EC_{50}$ values as a measure of compound potency. (Table 2, FIG. 9). Compound efficacy is presented as percent activation compared to 1 as displayed in FIG. 4 since most compounds reach their $E_{max}$ at or below 50 μM. Exceptions to this are 2a, which did not reach a plateau below its solubility limit (~80 μM), 1b which plateaus around 100 and 2d which is toxic in the XylE assay at 50 μM. For the most part, compound potency does not significantly deviate from that of 1. In addition, 2e and 2f maintain comparable potency to 1 while exhibiting a ~70% drop in efficacy indicating potency and efficacy do not correlate well. These data suggest that efficacy is a more important quantitative descriptor of compound activity.

TABLE 2

| Cmpd | Structure | EC50 (μM) | pEC50 | Efficacy (%) |
|---|---|---|---|---|
| 1 | 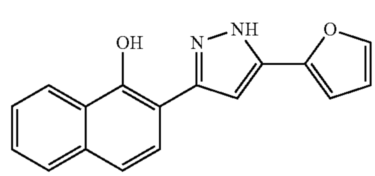 [SMILES: Oc1c(-c2cc(-c3ccco3)[nH]n2)ccc2ccccc12] | 11.6 | 4.90 ± 0.37 | 100 |
| 1a | 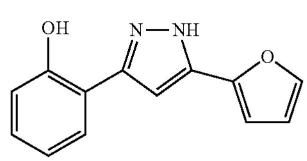 | 30.4 | 4.49 ± 0.083 | 28.2 ± 5.4 |

TABLE 2-continued

| Cmpd | Structure | EC50 (µM) | pEC50 | Efficacy (%) |
|---|---|---|---|---|
| 1b | (2-OH, 4-MeO-phenyl)-pyrazole-furan | 50.2 | 4.30 ± 0.20 | 26.2 ± 6.7 |
| 2a | (2-OH-phenyl)-pyrazole-thiophene | ND | ND | 17.0 ± 2.9 |
| 2c | (2-OH-phenyl)-pyrazole-phenyl | 14.6 | 4.66 ± 0.016 | 87.8 ± 23.7 |
| 2d | (2-OH-phenyl)-pyrazole-(2-OH-phenyl) | 5.81 | 5.24 ± 0.076 | ND |
| 2e | (2-OH-phenyl)-pyrazole-(2-F-phenyl) | 10.7 | 4.97 ± 0.033 | 35.7 ± 10.1 |
| 2f | (2-OH-phenyl)-pyrazole-(2,6-diF-phenyl) | 13.6 | 4.90 ± 1.1 | 30.1 ± 8.0 |

$EC_{50}$, $pEC_{50}$ and efficacy values for 1 and the top six HssRS activators from the single point screen. $EC_{50}$ and $pEC_{50}$ were calculated from concentration response curves after 6 h of growth using the XylE reporter assay. An $EC_{50}$ for 2a could not be determined because the concentration response curve did not plateau below its solubility limit. Efficacy is the percent activation of HssRS compared to 1 at 50 µM (all compounds reach $E_{max}$ at or below 50 µM except 2a). All data were collected in triplicate and error values are one standard deviation from the mean.

Figure 5:
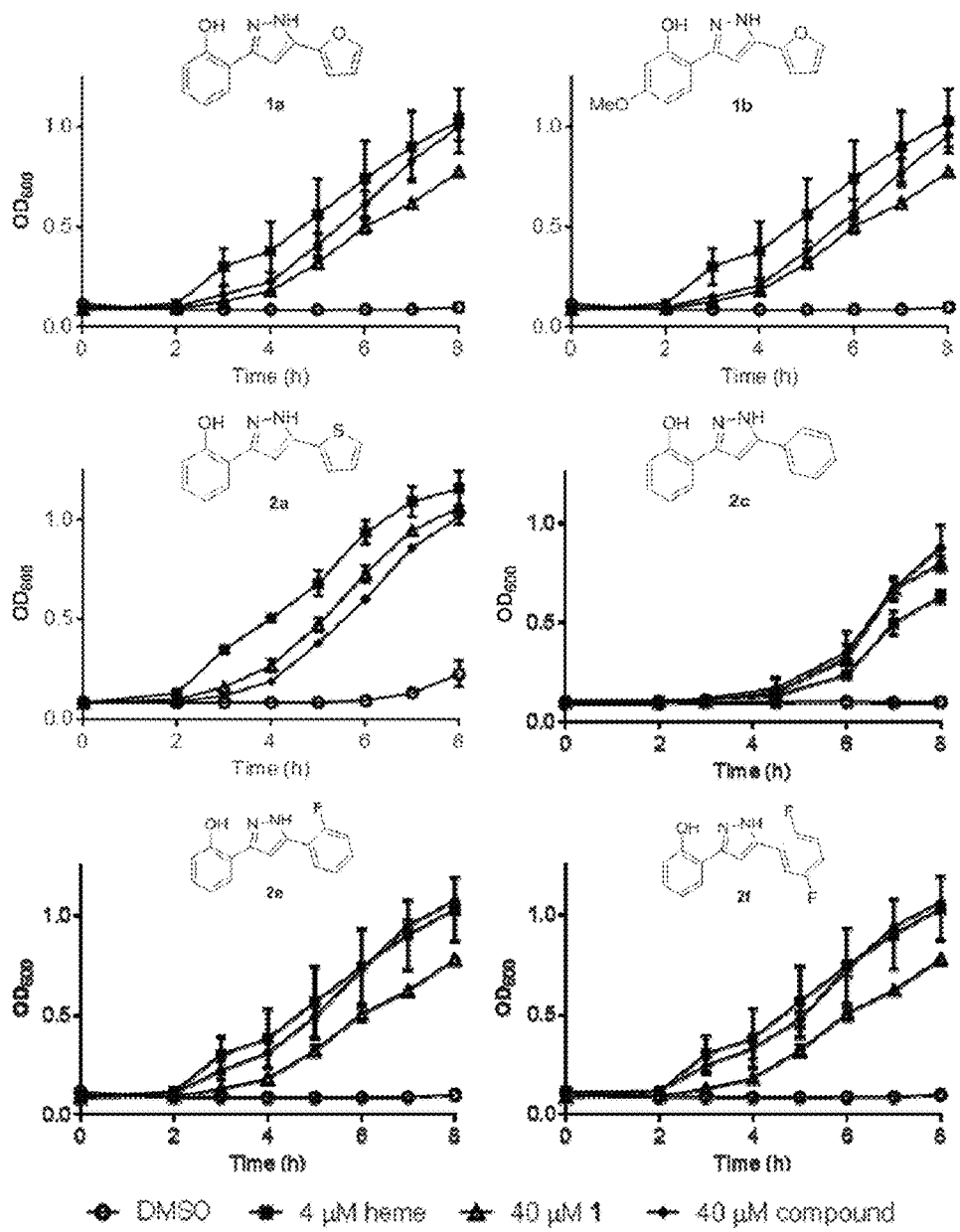
FIG. 5. Adaptation for heme toxicity by the indicated compound compared to vehicle (DMSO), 4 µM heme, and 40 µM 1. Overnight cultures were grown in medium with the indicated additive and then subcultured into medium containing a toxic concentration of heme (20 µM). Growth was monitored by reading OD$_{600}$ at indicated time points. Data are the average of three replicates and error bars represent one standard deviation from the mean.
Figure 6:
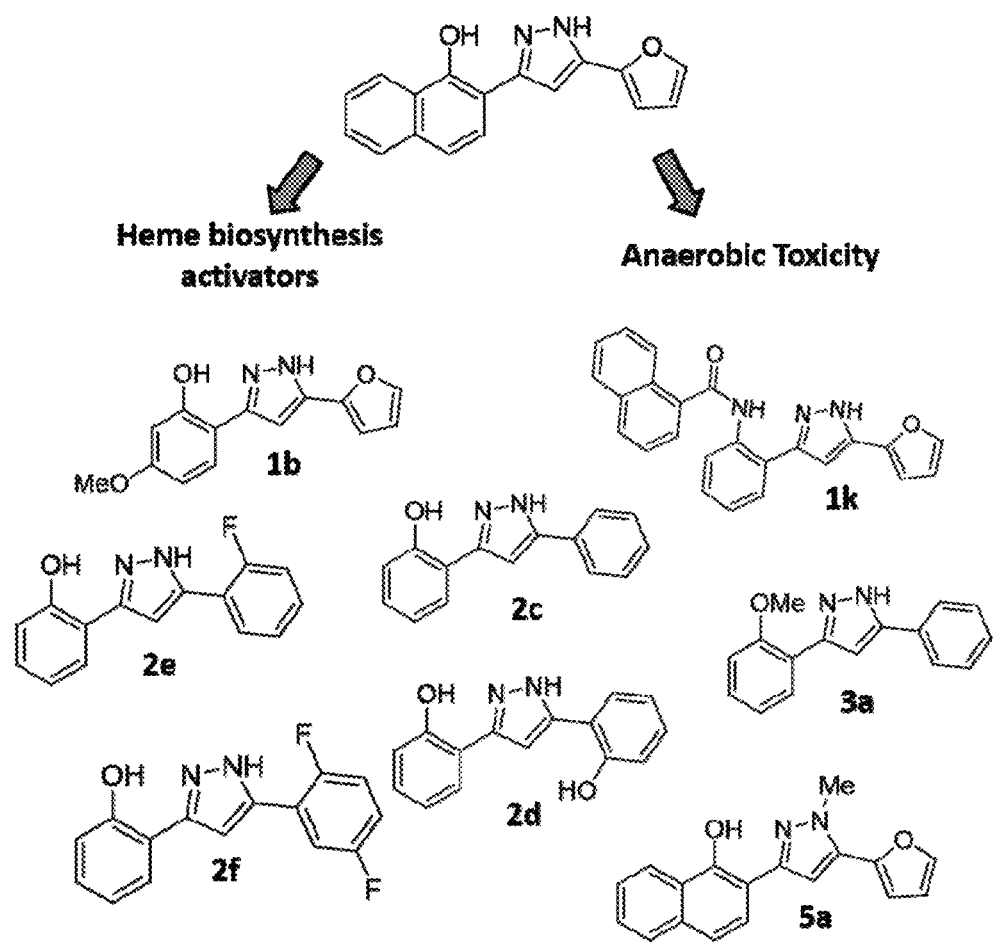
FIG. 6. Molecules produced for studies set forth in the Examples can be divided into three categories: activators of heme biosynthesis, inhibitors of anaerobic growth, and hybrids exhibiting both activities.
Figure 7:
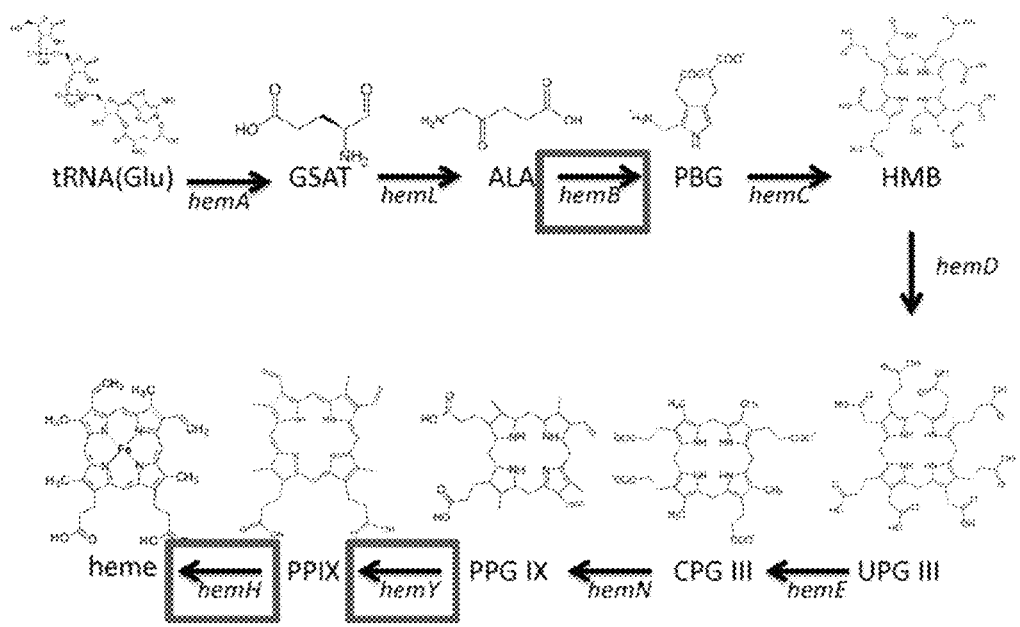
FIG. 7. Heme Biosynthetic Pathway.
Figure 10A:
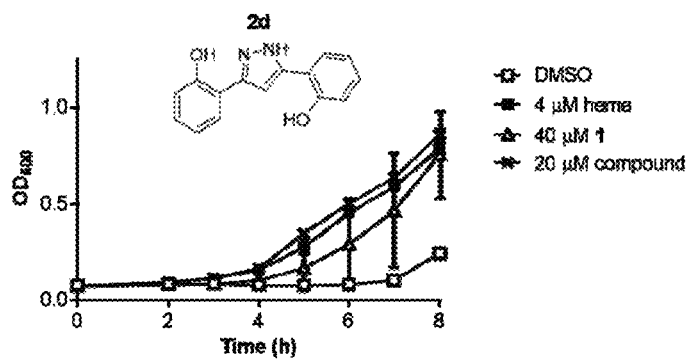
FIG. 10A. Adaptation for heme toxicity by compound 2d at the nontoxic concentration of 20 µM and FIG. 10B. Adaptation for heme toxicity by compounds determined to be inactive based on single point XylE data. Overnight cultures were grown in medium with the indicated additive and then subcultured into medium containing a toxic concentration of heme (20 μM). Growth was monitored by reading $OD_{600}$ at indicated time points. Data are the average of three replicates and error bars represent one standard deviation from the mean.
Figure 10B:
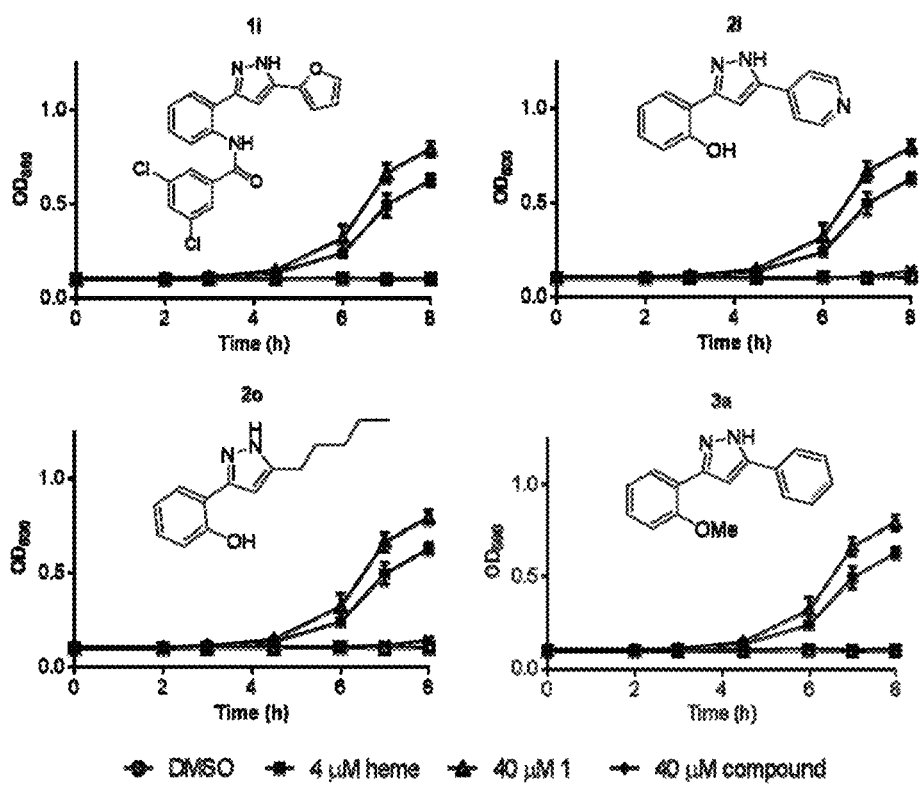

Finally, the top activators were assayed for their ability to preadapt *S. aureus* to heme as an indication that they can activate HssRS outside the context of a reporter assay. Pretreatment of cultures with a compound that induces HrtAB expression through activation of HssRS at subtoxic concentrations allows the bacteria to survive and grow when subcultured into a toxic concentration of heme. Pretreatment with 4 µM heme, 40 µM 1, and vehicle with 40 µM of each of the top activators were compared (excluding 2d because of toxicity). All derivatives were able to preadapt *S. aureus* to a toxic concentration of heme (20 µM) as well as 4 µM heme and 40 µM 1 (FIG. 5). The discrepancy between XylE assay and heme adaptation activity is likely due to the length of treatment with compound (6 h vs. 15 h). Pretreatment with 2d at the nontoxic concentration of 20 µM induced excellent preadaptation to heme toxicity (FIG. 10A). Four inactive derivatives from the single point screen, 1i, 2i, 2o, and 3a, were also assayed for preadaptation to heme toxicity. Growth of bacteria subcultured into 20 µM heme after pretreatment with 40 µM compound was indistinguishable from vehicle confirming that these compounds do not activate HssRS (FIG. 10B).

1 does not Strongly Bind Iron.

Figure 11:
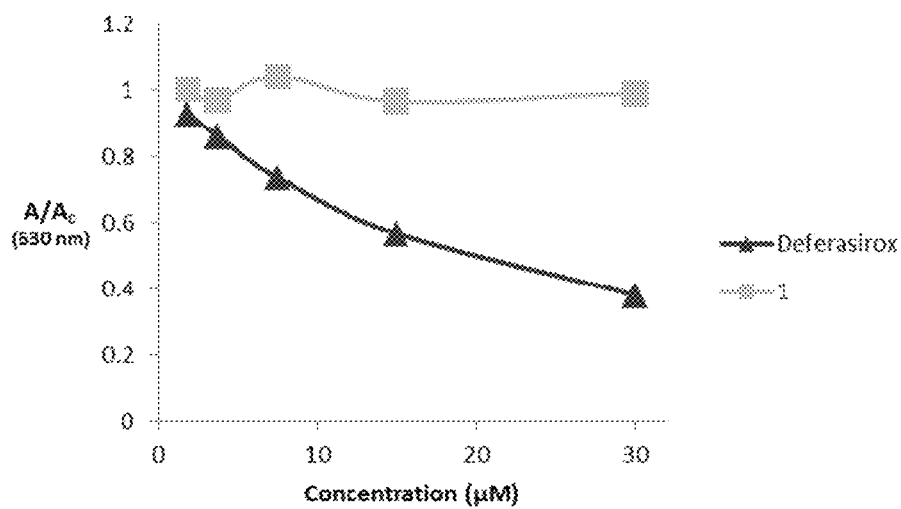
FIG. 11. CAS assay to determine the ability of 1 to bind iron. Deferasirox was used as a positive control.
Figure 11:
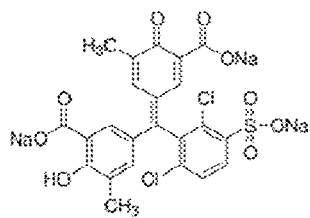
Figure 11:
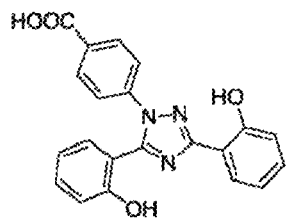

The results of the HssRS activation screen suggest that any disruption to the hydrogen bonding ability of the molecule eliminates this activity. While this may be important for binding to a protein target, it may also interfere with the potential for the molecule to bind to metals of biological significance. The hydrogen bond donor-acceptor orientation is potentially capable of binding iron.[20] Since its primary activity is associated with heme-iron metabolism, the ability of 1 to bind iron was determined using the Chromazural-S (CAS) assay.[21] When compared to the known iron chelator deferasirox, 1 does not strongly bind iron (FIG. 11). Therefore, it is unlikely that iron chelation is involved in the activity of these molecules.

Anaerobic Toxicity.

Next, the compound library was screened for anaerobic toxicity by generating concentration response curves for 9 h of growth and determining $IC_{50}$ values (Table 3). Wild type *S. aureus* strain Newman was grown in an anaerobic chamber in appropriate media to ensure exclusion of terminal electron acceptors sufficient to force the bacteria to ferment. In addition, an isogenic menB mutant was used as a positive control as this strain lacks the electron carrier menaquinone, rendering the bacterium incapable of generating energy through respiration in the presence of any terminal electron acceptor.[16] In parallel, the $IC_{50}$ values were determined in *S. aureus* grown aerobically to identify derivatives that exhibit toxicity independent of respiration. The arbitrary cut off point for toxicity of 60 μM was chosen as many of the compounds were not entirely soluble above this concentration.

TABLE 3

$IC_{50}$ values (μM) for all compounds were derived from concentration response curves of the fraction of growth compared to untreated control after 9 h of growth of the indicated strain and condition. Data were collected in triplicate. Error values are represented as the 95% confidence interval. $IC_{50}$ values greater than 60 μM could not be reliably determined because of solubility problems at high concentrations and compounds with an $IC_{50}$ >60 μM are considered nontoxic. *denotes $IC_{50}$ close to 60 μM but solubility issues prevented accurate determination.

| Cmpd | Newman aerobic | Newman anaerobic | ΔmenB |
| --- | --- | --- | --- |
| 1 | >60 | 13.5 (8.42-21.7) | 1.66 (0.491-5.63) |
| 1a | >60 | >60 | 35.6 (31.0-41.5) |
| 1b | >60 | >60 | >60 |
| 1c | >60 | >60 | >60 |
| 1d | >60 | >60 | >60 |
| 4a | >60 | 26.5 (21.9-32.1) | 15.7 (11.5-21.5) |
| 4b | >60 | 4.27 (3.39-4.65) | 3.3 (1.28-8.55) |
| 1e | >60 | >60 | >60 |
| 1f | >60 | >60 | >60 |
| 1g | >60 | >60 | >60 |
| 1h | >60 | >60 | >60 |
| 1i | >60 | 19.6 (16.9-22.8) | 8.69 (7.65-9.88) |
| 1j | >60 | 11.6 (10.2-13.0) | 6.63 (5.02-8.76) |
| 1k | >60 | 13.4 (12.3-14.7) | 5.89 |
| 1l | >60* | 28.8 (22.0-37.7) | 21.4 (13.9-32.8) |
| 2a | >60 | >60 | >60 |
| 2b | >60 | >60 | >60 |
| 2c | >60 | 24.0 (20.0-28.7) | 25.2 (7.84-81.2) |
| 2d | 42.5 (40.2-44.9) | 15.8 (15.3-16.4) | 9.33 (4.89-20.1) |
| 2e | >60 | >60 | >60 |
| 2f | >60 | >60 | >60 |
| 2g | >60 | >60 | >60 |
| 2h | >60 | >60 | >60 |
| 2i | >60 | >60 | >60 |
| 2j | >60 | >60 | >60 |
| 2k | >60 | >60 | >60 |
| 2l | >60 | >60 | >60 |
| 2m | >60 | >60 | >60 |
| 2n | >60 | 25.3 (23.4-27.2) | 29.7 (24.6-35.9) |
| 2o | 48.6 (37.9-62.3) | 11.6 (10.3-13.1) | 13.2 (10.4-16.6) |
| 3a | >60 | 20.8 (17.9-24.2) | 24.9 (10.2-60.4) |
| 3b | >60 | >60 | >60 |

The majority of compounds were essentially nontoxic to aerobically growing Newman with the exceptions of 2d and 2o with $IC_{50}$'s of 42.2 and 48.6 μM, respectively. These data indicate that the majority of derivatives do not exhibit general toxicity.

Compounds 1a and 1b were relatively nontoxic to fermenting *S. aureus* suggesting that the B-ring of 1 is important for toxicity. O-methylation (1c) also eliminates toxicity. However, N-methylation does not decrease the toxicity of the molecules. In addition, the regiochemistry of N-methylation appears to exert a significant effect on toxicity. 4a is approximately five times less toxic to fermenting wildtype *S. aureus* and ΔmenB than 4b while the toxicity of 1 is intermediate between the two.

Substitution of the o-hydroxyl of 1a with aromatic amides (1i-1l) seems to impart toxicity to fermenting *S. aureus* comparable to 1. However, substitution with a sulfonamide renders the compound nontoxic under fermentative conditions. This may be a consequence of the differing properties of amides and sulfonamides ($pK_a$, hydrogen bonding, etc) or may be related to the added aromatic bulk of the amides while the methyl group of 1h is innocuous. We were unable to test this due to the propensity of amides with smaller R-groups to dehydrate to pyrazolo[1,5-c]quinazolines such as 5a (Supporting information).

Replacement of the furan with most aromatic or heteroaromatic groups resulted in nontoxic molecules under most conditions, the notable exceptions being 2c and 2d, with the furan replaced by phenyl and o-hydroxyphenyl, respectively. These compounds exhibit anaerobic toxicity similar to 1. Substitution of the phenyl ring with fluorine(s) (2e, 2f) eliminates this toxicity. Replacement of the furan with large (>4C) alkyl groups also produced molecules with anaerobic toxicity. 2n and 2o were comparably toxic to 1 while 2j, 2k, 2l, and 2m, with hydrogen or smaller alkyl groups were nontoxic under all conditions.

While O-methylation of 1 eliminates toxicity, O-methylation of 2c (4a), maintains toxicity comparable to the parent molecule. This suggests that O-alkylation is not a major contributor to the toxic character of these molecules.

Figure 4:
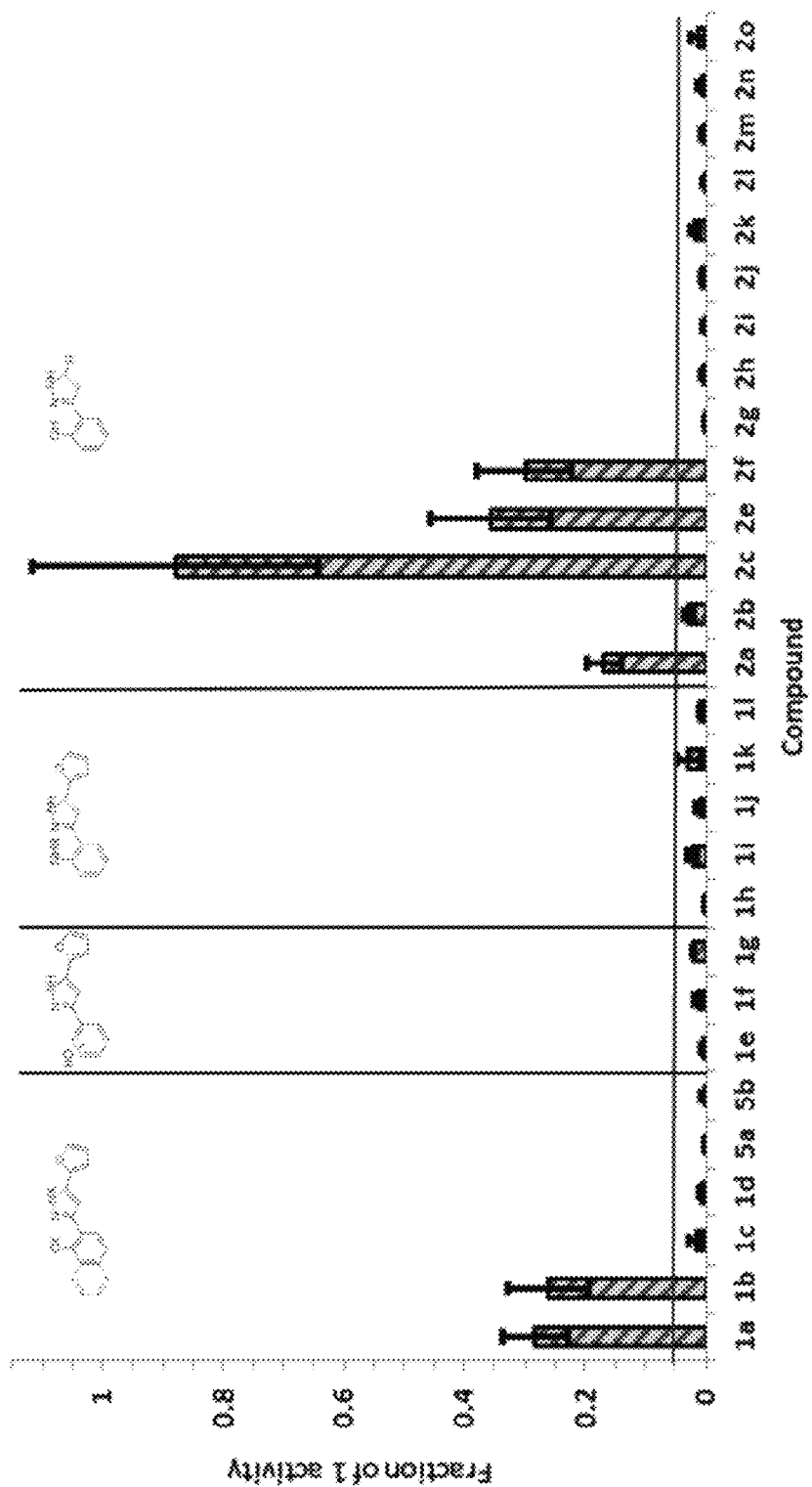
FIG. 4. Identification of HssRS activators by XylE assay. Activation of HssRS is presented as the fraction of activation by the indicated derivative relative to 1 at 50 µM. Data are the average of three replicates. Error bars represent one standard deviation from the mean. The red bar indicates the cut off value for activity (above=active, below=inactive).

Compound 2e was previously reported to exhibit anaerobic toxicity and efficacy in a mouse model of *S. aureus* infection.[14] The difference in these toxicity results is likely due to the method of $IC_{50}$ determination. The previous method relied on a significant back-dilution of overnight cultures prior to compound addition to account for the time needed for the apparatus to become anaerobic. Bacteria grown at this low cell density could experience greater toxicity from the compound than the higher cell density used in this work. Although, 2e is not bacteriostatic under the conditions tested here, the ability of the compound to activate HssRS was corroborated (FIG. 4). This suggests that derivatives that either activate HssRS or inhibit growth under anaerobiosis may both be valid antibacterial approaches. This is supported by previous studies that have reported that HssRS activation affects virulence during infection.[11]

Relationship Between HssRS Activation and Anaerobic Toxicity.

Any disruption to the hydrogen bond donating ability of the molecule through O- or N-methylation or replacement with alternate hydrogen bond donor groups removes its ability to activate heme biosynthesis and is absolutely required for this activity. In contrast, the hydrogen bonding character seems to be less important for toxicity as several O- and N-methylated derivatives maintain toxicity levels comparable to 1. Comparing the methylated derivatives of 1; 1c, 4a, and 4b, O-methylation eliminates toxicity while the regiochemistry of N-methylation has a significant impact on the magnitude of toxicity.

Modification at the 5-position significantly affects which activity is favored. Aromatic or heteroaromatic groups are required to activate heme biosynthesis while large alkyl groups favor toxicity. Despite this, some overlap between HssRS activation and toxicity is evident. Replacement of the furan with a phenyl ring (1a to 2c) restores toxicity comparable to 1 and maintains HssRS activity. O-methylation of this derivative (3a) removes HssRS activity as expected while maintaining toxicity. Fluorination of 2c to 2e maintains HssRS activity, but removes toxicity. In addition, fluorination of 3a to 3b eliminates toxicity. Interestingly, 2d which is highly symmetric, exhibits both activities.

In summary, using a medicinal chemistry approach we have decoupled the two activities of 1 and established two classes of molecules: activators of heme biosynthesis and inhibitors of anaerobic growth (FIG. 6). These molecules will serve as probes for further study of their respective activities and mechanisms of action without concern for the off target effects of the parent molecule. Future directions will focus on optimizing the activity of both classes of molecules in *S. aureus* as well as evaluation of activity in other Gram positive and Gram negative bacteria.

Example 2: System to Screen for Small Molecule Activators of HssRS and their Targets A unique *S. aureus*-based screening system was created by the present inventors to study the mechanism of activation of the heme-sensing two-component system (TCS), HssRS. The unique system is useful for identifying compounds capable of activating HssRS, and for identifying the target of such compounds within the heme biosynthesis machinery, for example, small molecule targets of enzymes within the heme biosynthetic pathway.

Small molecule activators of HssRS can be identified using high-throughput screens, such as the one previously described by present inventors in Mike et al, PNAS 2013, which provides for a luminescent signal to be generated when HssRS is activated. Small molecule activators of HssRS, as well as the targets of the small molecules, can be identified using the unique *S. aureus*-based screening system and methods disclosed herein.

Briefly, when HssRS is stimulated, it induces expression of hrtAB. The hrtAB promotor, Phrt, was placed upstream of the *E. coli* toxin, RelE, which impairs translation through mediating cleavage of mRNA, thus leading to growth arrest. The Phrt-RelE construct was inserted in place of the hrtAB locus using allelic exchange to create a unique *S. aureus* phrt-relE. When a candidate small molecule that activates HssRS is contacted with a *S. aureus* phrt-relE cell, expression of RelE is induced, leading to cell death. In this manner, cell death allows the candidate small molecule to be identified as a small molecule activators of HssRS. Further, Bacteria that survive the otherwise toxic treatment represent spontaneous resistant mutants. These surviving bacteria can be sequenced to identify genetic mutations. The target(s) of the small molecule activator will be the protein(s) containing the mutation(s) identified in the sequencing.

In the present study, PhrtrelE was plated on solid media containing either heme or the "882 compound."

882 Compound

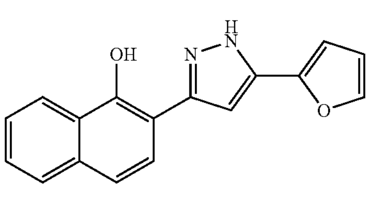

Exposure to either compound resulted in Phrt activation, inducing expression of relE and thus growth arrest.

Bacteria that survived heme or 882 treatment represented spontaneous resistant mutants. This screen identified 56 *S. aureus* PhrtrelE strains unresponsive to heme, and 30 strains unresponsive to 882. The hssRS and Phrt loci from these 86 strains were sequenced enabling the identification of numerous mutations required for HssRS function. Notably, three strains were identified that were unresponsive to 882 and do not contain mutations in HssRS or Phrt. Whole genome sequencing revealed that each of these three strains contains a single mutation in enzyme components of the heme biosynthetic machinery. With reference to the heme biosynthetic pathway set forth in FIG. 7, mutations were found in the enzymes hemB, which catalyzes the production of PBG from ALA, hemY, which catalyzes the production of PPIX (protoporphyrin IX) from PPG IX, and hem H, which catalyzes the production of hem from PPIX.

Because ALA is the first committed precursor molecule in the heme biosynthetic pathway, if ALA is contacted with bacteria, the bacteria will generated enhanced amounts of all of the heme precursor molecules downstream of ALA. However, while treatment with ALA results in accumulation of PBG, treatment with the 882 compound does not (data not shown). As such, the target of 882 must not be hemB. These results are contrasted to other results, which show that 882 does increase PPIX accumulation, suggesting hemY to be the target of the 882 compound (data not shown).

Example 3: Activation of HemY by Small Molecule

Sequencing of the spontaneous resistant mutants referenced in Example 2 identified a T183K mutation in HemY. Subsequent studies revealed that the 882 compound indeed activates wild type *S. aureus* hemY, but not the T183K point mutant of hemY, confirming hemY as the target of the 882 compound. Only a limited number (about 10-12) small molecule activators of enzymes have been previously identified, making the identification of the 882 compound as an activator of hemY a notable discovery.

Indeed, further studies have shown that 882 interacts with HemY from a variety of organisms, activating the enzyme leading to an increase in PPIX and heme synthesis. As shown in FIGS. 7-9, the 882 compound activates hemY/PPO in *Bacillus subtilis* and *Propionibacterium acnes*, as well as mammalian PPO in *Homo sapiens*.

Accordingly, the present inventors have discovered a small molecule activator of hemY/PPO that is active in a variety of organisms, leading to an increase in PPIX and heme synthesis. Accumulation of heme in a microbe is toxic to that microbe. See, e.g., Anzaldi and Skaar, "Overcoming the Heme Paradox: Heme Toxicity and Tolerance in Bacterial Pathogens," *Infection and Immunity,* 78(12):4977-89. In this regard, the presently-disclosed subject matter includes a method for treating a microbial infection, which is discussed in further detail herein.

Example 4: Phototherapy

As noted herein, with reference to FIG. 7, because ALA is the first committed precursor molecule in the heme biosynthetic pathway, if ALA is contacted with bacteria, the bacteria will generate enhanced amounts of all of the heme precursor molecules downstream of ALA. It is also known that if ALA is added to bacteria, the accumulation of all of these downstream heme precursor molecules leads to photosensitization of the bacteria. In this regard, ALA coupled with light therapy is toxic to bacteria.

The present inventors have found that treatment with the small molecule activator of hemY/PPO, which catalyzes the production of PPIX, coupled with light therapy is toxic to bacteria. Briefly, S. aureus was incubated with the 882 compound for 30 minutes at 37° C., treated with light for 45 minutes (500 W halogen), and then a colony-forming unit (CFU) count was conducted. Treatment with the 882 compound leads to staphylococcal photosensitization. Treatment with the 882 compound (50 µM) and light appears to be more toxic to the bacteria than ALA (10 mg/mL) an light.

Example 5: (Prophetic in Part) Production of Hemoproteins

Heme binding proteins (hemoproteins) have many commercial applications but purification of these proteins is often limited by an inability of the producing strain to make enough heme to populate the overexpressed hemoprotein. As noted hereinabove, the present inventors have identified a small molecule activator of the hemY, which catalyzes one of the final steps in the heme biosynthesis pathway. The present inventors contemplate that the identified small molecule activator could be used in connection techniques to overexpress hemoproteins of interest, providing sufficient levels of heme to populate the proteins, allowing for enhanced production and purification.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES (1) DeLeo, F. R., Otto, M., Kreiswirth, B. N., and Chambers, H. F. (2010) Community-associated meticillin-resistant *Staphylococcus aureus*. *Lancet* 375, 1557-68.
(2) Yamamoto, T., Nishiyama, A., Takano, T., Yabe, S., Higuchi, W., Razvina, O., and Shi, D. (2010) Community-acquired methicillin-resistant *Staphylococcus aureus*: community transmission, pathogenesis, and drug resistance. *J. Infect. Chemother.* 16, 225-54.
(3) Nathan, C. (2012) Fresh approaches to anti-infective therapies. *Sci. Transl. Med.* 4, 140sr2.
(4) Somerville, G. A., and Proctor, R. A. (2009) At the crossroads of bacterial metabolism and virulence factor synthesis in Staphylococci. Microbiol. *Mol. Biol. Rev.* 73, 233-48.
(5) Skaar, E. P., Humayun, M., Bae, T., DeBord, K. L., and Schneewind, O. (2004) Iron-source preference of *Staphylococcus aureus* infections. *Science* 305, 1626-8.
(6) Mazmanian, S. K., Skaar, E. P., Gaspar, A. H., Humayun, M., Gornicki, P., Jelenska, J., Joachmiak, A., Missiakas, D. M., and Schneewind, O. (2003) Passage of heme-iron across the envelope of *Staphylococcus aureus*. *Science* 299, 906-9.
(7) Torres, V. J., Pishchany, G., Humayun, M., Schneewind, O., and Skaar, E. P. (2006) *Staphylococcus aureus* IsdB is a hemoglobin receptor required for heme iron utilization. *J. Bacteriol.* 188, 8421-9.
(8) Pishchany, G., Dickey, S. E., and Skaar, E. P. (2009) Subcellular localization of the *Staphylococcus aureus* heme iron transport components IsdA and IsdB. *Infect. Immun.* 77, 2624-34.
(9) Anzaldi, L. L., and Skaar, E. P. (2010) Overcoming the heme paradox: heme toxicity and tolerance in bacterial pathogens. *Infect. Immun.* 78, 4977-89.
(10) Friedman, D. B., Stauff, D. L., Pishchany, G., Whitwell, C. W., Torres, V. J., and Skaar, E. P. (2006) *Staphylococcus aureus* redirects central metabolism to increase iron availability. *PLoS Pathog.* 2, 0777-0789.
(11) Torres, V. J., Stauff, D. L., Pishchany, G., Bezbradica, J. S., Gordy, L. E., Iturregui, J., Anderson, K. L., Dunman, P. M., Joyce, S., and Skaar, E. P. (2007) A *Staphylococcus aureus* regulatory system that responds to host heme and modulates virulence. *Cell Host Microbe* 1, 109-19.
(12) Stauff, D. L., Tones, V. J., and Skaar, E. P. (2007) Signaling and DNA-binding activities of the *Staphylococcus aureus* HssR-HssS two-component system required for heme sensing. *J. Biol. Chem.* 282, 26111-21.
(13) Johansson, P., and Hederstedt, L. (1999) Organization of genes for tetrapyrrole biosynthesis in Gram-positive bacteria. *Microbiology* 145, 529-538.
(14) Mike, L. A., Dutter, B. F., Stauff, D. L., Moore, J. L., Vitko, N. P., Aranmolate, O., Kehl-Fie, T. E., Sullivan, S., Reid, P. R., DuBois, J. L., Richardson, A. R., Caprioli, R. M., Sulikowski, G. A., and Skaar, E. P. (2013) Activation of heme biosynthesis by a small molecule that is toxic to fermenting *Staphylococcus aureus*. *Proc. Natl. Acad. Sci. U.S.A* 110, 8206-11.
(15) Allison, K. R., Brynildsen, M. P., and Collins, J. J. (2011) Metabolite-enabled eradication of bacterial persisters by aminoglycosides. *Nature* 473, 216-220.
(16) Kohler, C., von Eiff, C., Liebeke, M., McNamara, P. J., Lalk, M., Proctor, R. A., Hecker, M., and Engelmann, S. (2008) A defect in menadione biosynthesis induces global changes in gene expression in *Staphylococcus aureus*. *J. Bacteriol.* 190, 6351-64.
(17) Proctor, R. A., von Eiff, C., Kahl, B. C., Becker, K., McNamara, P., Herrmann, M., and Peters, G. (2006) Small colony variants: a pathogenic form of bacteria that facilitates persistent and recurrent infections. *Nat. Rev. Microbiol.* 4, 295-305.
(18) Arrowsmith, C. H., Audia, J. E., Austin, C., Baell, J., Bennett, J., Blagg, J., Bountra, C., Brennan, P. E., Brown, P. J., Bunnage, M. E., Buser-Doepner, C., Campbell, R. M., Carter, A. J., Cohen, P., Copeland, R. A., Cravatt, B., Dahlin, J. L., Dhanak, D., Edwards, A. M., Frye, S. V, Gray, N., Grimshaw, C. E., Hepworth, D., Howe, T., Huber, K. V. M., Jin, J., Knapp, S., Kotz, J. D., Kruger, R. G., Lowe, D., Mader, M. M., Marsden, B., Mueller-Fahrnow, A., Müller, S., O'Hagan, R. C., Overington, J. P., Owen, D. R., Rosenberg, S. H., Roth, B., Ross, R., Schapira, M., Schreiber, S. L., Shoichet, B., Sundstrom, M., Superti-Furga, G., Taunton, J., Toledo-Sherman, L., Walpole, C., Walters, M. A., Willson, T. M., Workman, P., Young, R. N., and Zuercher, W. J. (2015) The promise and peril of chemical probes. *Nat. Chem. Biol.* 11, 536-541.
(19) Fustero, S., Sánchez-Roselló, M., Barrio, P., and Simón-Fuentes, A. (2011) From 2000 to mid-2010: a fruitful decade for the synthesis of pyrazoles. *Chem. Rev.* 111, 6984-7034.
(20) Richardson, D. R., and Bernhardt, P. V. (1999) Crystal and molecular structure of 2-hydroxy-1-naphthaldehyde isonicotinoyl hydrazone (NIH) and its iron(III) complex: an iron chelator with anti-tumour activity. *J. Biol. Inorg. Chem.* 4, 266-273.
(21) Schwyn, B., and Neilands, J. B. (1987) Universal chemical assay for the detection and determination of siderophores. *Anal. Biochem.* 160, 47-56.

(22) Fernadez, et al., (2010) "Two Coregulated Efflux Transporters Modulate Intracellular Heme and Protoporphyrin IX Availability in *Streptococcus agalactiae*," PLOS Pathogens, 6(4).

(23) Heinemann, et al., *Antimicrob. Agents Chemother.* (2010).

(24) Mike, et al., (2014) "Two-Component System Cross-Regulation Integrates *Bacillus anthracis* Response to Heme and Cell Envelope Stress," *PLOS Pathogens*, 10(3).

(25) Morimoto, et al, (2014), "Photodynamic Therapy Using Systemic Administration of 5-Aminolevulinic Acid and a 410-nm Wavelength Light-Emitting Diode for Methicillin-Resistant *Staphylococcus aureus*-Infected Ulcers in Mice," PLOS ONE, 9(8).

(26) Nakonieczna, et al., (2010) "Superoxide dismutase is upregulated in *Staphylococcus aureus* following protoporphyrin-mediated photodynamic inactivation and does not directly influence the response to photodynamic treatment," BMC Microbiology, 10:323.

(27) Qi, et al., *J. Struct. Biol.* (2010).

(28) Villarreal, et al., (2008) "Enhancement of Recombinant Hemoglobin Production in *Escherichia coli* BL21 (DE3) COntianing the *Plesiomonas shigelloides* Heme Transport System," *Applied and Environmental Microbiology*, 74(18): 5854-5856.

(29) Wakeman, et al., (2014) "Differential Activation of *Staphylococcus aureus* Heme Detoxification Machinery by Heme Analogues," *J. of Bacteriology*, 196(7): 1335-42.

(31) International Patent Application Publication No. WO 2014/018925 to Skaar, et al. for COMPOSITIONS AND METHODS FOR TREATING MICROBIAL INFECTIONS.

(32) Kallander, L. S., Lu, Q., Chen, W., Tomaszek, T., Yang, G., Tew, D., Meek, T. D., Hofmann, G. A., Schulz-Pritchard, C. K., Smith, W. W., Janson, C. A., Ryan, M. D., Zhang, G.-F., Johanson, K. O., Kirkpatrick, R. B., Ho, T. F., Fisher, P. W., Mattern, M. R., Johnson, R. K., Hansbury, M. J., Winkler, J. D., Ward, K. W., Veber, D. F., and Thompson, S. K. (2005) 4-Aryl-1,2,3-triazole: a novel template for a reversible methionine aminopeptidase 2 inhibitor, optimized to inhibit angiogenesis in vivo. *J. Med. Chem.* 48, 5644-7.

(33) Reed, C., Ibrahim, A., Edwards, J. E., Walot, I., and Spellberg, B. (2006) Deferasirox, an iron-chelating agent, as salvage therapy for rhinocerebral mucormycosis. *Antimicrob. Agents Chemother.* 50, 3968-9.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method for treating a gram-positive bacterial infection, comprising:
   activating protoporphyrinogen oxidase (PPO) in the gram-positive bacteria, thereby producing compounds via the heme biosynthetic pathway in the gram-positive bacteria, by administering an effective amount of a compound of the formula:

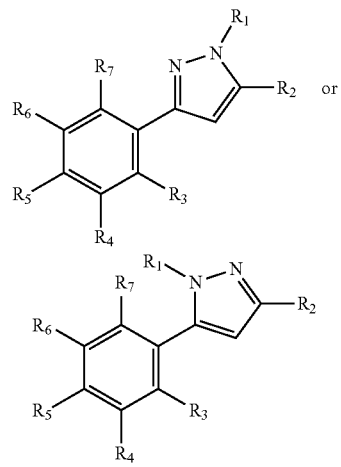

wherein,
$R_1$ is H, alkyl, aryl, heteroaryl;
$R_2$ is H, halogen, alkyl, aryl, heteroaryl;
$R_3$ is H, hydroxyl, alkoxy, alkyl, aryl, heteroaryl, amino, amino sulfonyl, acetamide;
$R_4$ is H, hydroxyl, alkoxy, alkyl, aryl, heteroaryl, amino, amino sulfonyl, acetamide;
$R_5$ is H, hydroxyl, alkoxy, alkyl, aryl, heteroaryl, amino, amino sulfonyl, acetamide;
$R_6$ is H, hydroxyl, alkoxy, alkyl, aryl, heteroaryl, amino, amino sulfonyl, acetamide;
$R_7$ is H, hydroxyl, alkoxy, alkyl, aryl, heteroaryl, amino, amino sulfonyl, acetamide;
$R_8$ is —$CR_3$, O, S;
wherein $R_5$ and $R_6$, $R_7$ and $R_6$, $R_5$ and $R_4$, $R_4$ and $R_3$ can cyclize forming a 3-10 member ring comprising C, O, S, and/or N optionally substituted with one or more $R_3$; and
administering light therapy.

2. The method of claim 1, wherein:
$R_1$ is H, alkyl, aryl;
$R_2$ is H, halogen, alkyl, aryl, heteroaryl;
$R_3$ is H, alkyl, hydroxyl, alkoxy, amino, amino sulfonyl, acetamide, aryl, heteroaryl;
$R_4$ is H, alkyl, hydroxyl, alkoxy, amino, amino sulfonyl, acetamide;
$R_5$ is H, alkyl, hydroxyl, alkoxy, amino, amino sulfonyl, acetamide;
$R_6$ is H, alkyl, aryl.

3. The method of claim 1, wherein
$R_1$ is H, $CH_3$, or

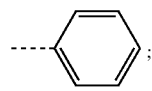

$R_2$ is H, $CH_3$, $CH_2CH_3$,

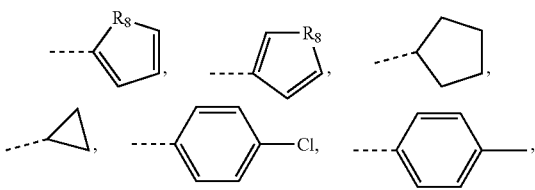

87

-continued

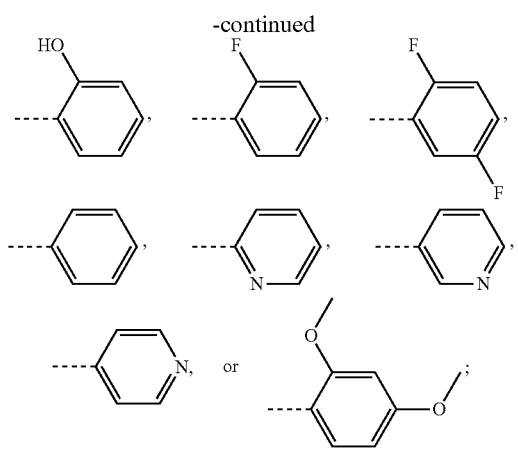

$R_3$ is H, OH,

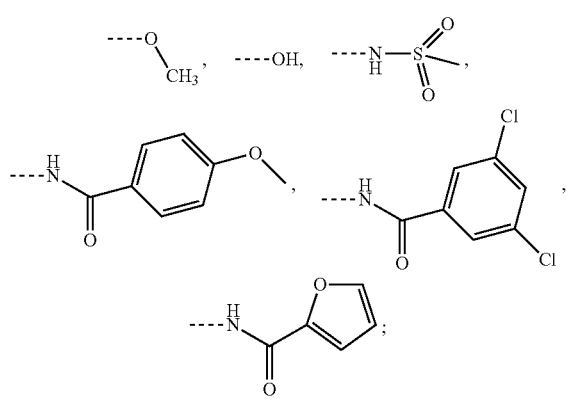

$R_4$ is H, OH,

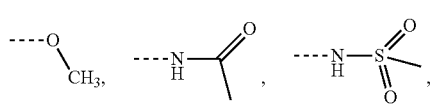

or $R_4$ and $R_5$, taken together with the carbon atoms to which they are bonded, can form an aromatic ring containing 6 carbon atoms;

$R_5$ is H, OH,

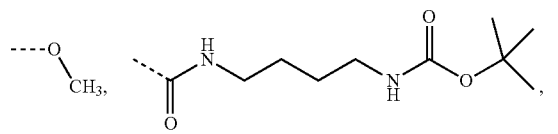

or $R_4$ and $R_5$, taken together with the carbon atoms to which they are bonded, can form an aromatic ring containing 6 carbon atoms, or $R_5$ and $R_6$, taken together with the carbon atoms to which they are bonded, can form an aromatic ring containing 6 carbon atoms;

$R_6$ is H, or $R_5$ and $R_6$, taken together with the carbon atoms to which they are bonded, can form an aromatic ring containing 6 carbon atoms;

88

$R_7$ is H or OH; and
$R_8$ is O or S.

4. The method of claim 1, wherein the compound is selected from the compounds set forth in Table 1.

5. The method of claim 1, wherein the compound is:

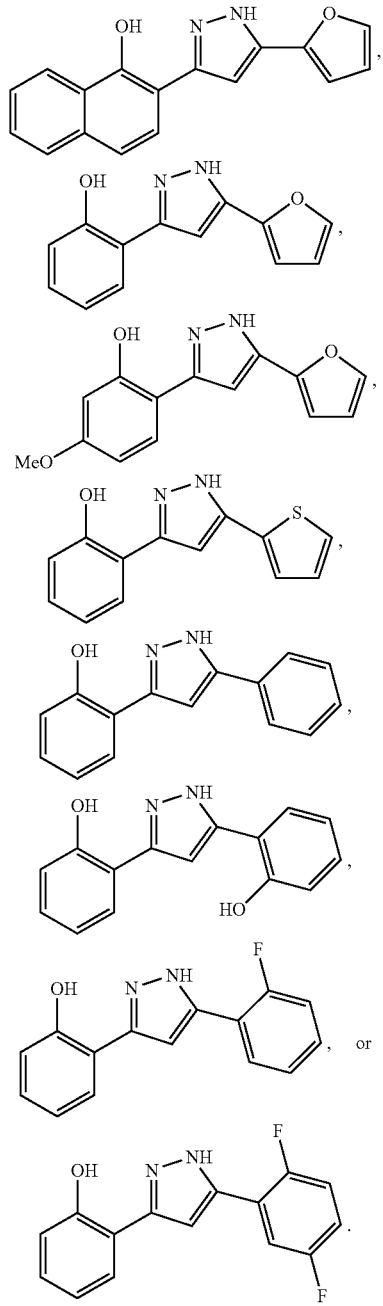

6. The method of claim 1, wherein the compound is provided in a pharmaceutical composition.

7. The method of claim 1, and further comprising administration of another compound or composition having microbial activity.

8. The method of claim 1, wherein the compound is administered topically.

9. The method of claim 1, wherein the light therapy uses light having a wavelength of about 380 nm.

* * * * *